United States Patent
Hathaway et al.

(10) Patent No.: US 11,905,537 B2
(45) Date of Patent: Feb. 20, 2024

(54) BIFUNCTION CHEMICAL EPIGENETIC MODIFIERS AND METHODS OF USE

(71) Applicant: The University of North Carolina at Chapel Hill, Chapel Hill, NC (US)

(72) Inventors: Nate Hathaway, Chapel Hill, NC (US); Jian Jin, New York, NY (US); Kyle Butler, Salt Lake City, UT (US); Anna Chiarella, Chapel Hill, NC (US)

(73) Assignee: THE UNIVERSITY OF NORTH CAROLINA AT CHAPEL HILL, Chapel Hill, NC (US)

( * ) Notice: Subject to any disclaimer, the term of this patent is extended or adjusted under 35 U.S.C. 154(b) by 721 days.

(21) Appl. No.: 16/636,464

(22) PCT Filed: Aug. 3, 2018

(86) PCT No.: PCT/US2018/045266
§ 371 (c)(1),
(2) Date: Feb. 4, 2020

(87) PCT Pub. No.: WO2019/028426
PCT Pub. Date: Feb. 7, 2019

(65) Prior Publication Data
US 2021/0355476 A1  Nov. 18, 2021

Related U.S. Application Data

(60) Provisional application No. 62/654,958, filed on Apr. 9, 2018, provisional application No. 62/541,343, filed on Aug. 4, 2017.

(51) Int. Cl.
| | | |
|---|---|---|
| C12N 9/90 | (2006.01) |
| A61K 47/55 | (2017.01) |
| A61K 31/167 | (2006.01) |
| A61K 31/436 | (2006.01) |
| A61K 38/15 | (2006.01) |
| C07K 14/47 | (2006.01) |
| C12N 9/22 | (2006.01) |
| C12N 15/11 | (2006.01) |

(52) U.S. Cl.
CPC .............. *C12N 9/90* (2013.01); *A61K 31/167* (2013.01); *A61K 31/436* (2013.01); *A61K 38/15* (2013.01); *A61K 47/55* (2017.08); *C07K 14/4702* (2013.01); *C12N 9/22* (2013.01); *C12N 15/111* (2013.01); *C12N 2310/20* (2017.05)

(58) Field of Classification Search
None
See application file for complete search history.

(56) References Cited

U.S. PATENT DOCUMENTS

2013/0018103 A1* 1/2013 Bradner ............... C07D 249/06
435/375

OTHER PUBLICATIONS

Højfeldt et al., "Bifunctional Ligands Allow Deliberate Extrinsic Reprogramming of the Glucocorticoid Receptor", Mol. Endocrinology, 2014, 28(2):249-259. doi: 10.1210/me.2013-1343.*
Antonarakis, E. S et al. "AR-V7 and Resistance to Enzalutamide and Abiraterone in Prostate Cancer." N. Engl. J. Med. 371, 1028-1038 (2014).
Bannister, A. J. & Kouzarides, T. "Regulation of chromatin by histone modifications." Cell Res. 21, 381-395 (2011).
Bantscheff, M. et al. "Chemoproteomics profiling of HDAC inhibitors reveals selective targeting of HDAC complexes." Nat. Biotechnol. 29, 255-65 (2011).
Becher, I. et al. "Chemoproteomics reveals time-dependent binding of histone deacetylase inhibitors to endogenous repressor complexes." ACS Chem. Biol. 9, 1736-1746 (2014).
Bintu, L. et al. "Dynamics of epigenetic regulation at the single-cell level." Science (80). 351, 720-724 (2016).
Burgess et al., "An Approach to Photolabile, Fluorescent Protecting Groups." J. Org. Chem. 62:5165-5168, 1997.
Chavez, A. et al. "Comparison of Cas9 activators in multiple species." Nat. Methods 13, 563-567 (2016).
Chen, B. et al. "Dynamic imaging of genomic loci in living human cells by an optimized CRISPR/Cas system." Cell 155, 1479-1491 (2013).
Chen, Y. et al. "A series of potent and selective, triazolylphenyl-based histone deacetylases inhibitors with activity against pancreatic cancer cells and Plasmodium falciparum." J. Med. Chem. 51, 3437-3448 (2008).
De Bono, J. S. et al. "Abiraterone and increased survival in metastatic prostate cancer." N. Engl. J. Med. 364, 1995-2005 (2011).
Delcuve, G. P., et al. "Roles of histone deacetylases in epigenetic regulation: emerging paradigms from studies with inhibitors." Clin. Epigenetics 4, 5 (2012).
Dokmanovic, M., et al. "Histone deacetylase inhibitors: overview and perspectives." Mol. Cancer Res. 5, 981-989 (2007).
Feinberg, A. P., et al. "Epigenetic modulators, modifiers and mediators in cancer aetiology and progression." Nat. Rev. Genet. 17, 284-99 (2016).
Gao, Y. et al. "Complex transcriptional modulation with orthogonal and inducible dCas9 regulators." Nat. Methods 1-9 (2016).
Gori, J. L. et al. "Delivery and Specificity of CRISPR-Cas9 Genome Editing Technologies for Human Gene Therapy." Hum. Gene Ther. 26, 443-451 (2015).
Guillier, F., et al. "Linkers and Cleavage Strategies in Solid-Phase Organic Synthesis and Combinatorial Chemistry." Chem. Rev. 100:2091-2157, 2000.
Guo, Z.- F., et al. "Facile functionalization of FK506 for biological studies by the thiol-ene 'click' reaction." RSC Adv. 4, 11400 (2014).
Hathaway, N. A. et al. "Dynamics and memory of heterochromatin in living cells." Cell 149, 1447-1460 (2012).

(Continued)

*Primary Examiner* — Suzanne M Noakes
(74) *Attorney, Agent, or Firm* — BALLARD SPAHR LLP

(57) ABSTRACT

The present disclosure relates to bifunctional chemical epigenetic modifiers, and methods of making, kits and using the bifunctional chemical epigenetic modifiers. The bifunctional chemical epigenetic modifiers can include a FK506 molecule or derivative thereof, a linker and a bifunctional ligand. The bifunctional ligand can be a histone deacetylase inhibitor.

8 Claims, 48 Drawing Sheets

Specification includes a Sequence Listing.

(56) References Cited

OTHER PUBLICATIONS

Harris, L. G. et al. "Evidence for a non-canonical role of HDAC5 in regulation of the cardiac Ncx1 and Bnp genes." Nucleic Acids Res. 44, 3610-3617 (2016).
Hilton, I. B. et al. "Epigenome editing by a CRISPR-Cas9-based acetyltransferase activates genes from promoters and enhancers." Nat. Biotechnol. 33, 510-7 (2015).
Højfeldt, J. W., et al. "Transforming ligands into transcriptional regulators: building blocks for bifunctional molecules." Chem. Soc. Rev. 40, 4286-94 (2011).
Højfeldt, et al. "Bifunctional Ligands Allow Deliberate Extrinsic Reprogramming of the Glucocorticoid Receptor," Molecular Endocrinology. 2014;28:249-259.
Hong, V., et al. "Analysis and optimization of copper-catalyzed azide-alkyne cycloaddition for bioconjugation." Angew. Chemie—Int. Ed. 48, (2009).
Hsu, P. D., et al. "Development and Applications of CRISPR-Cas9 for Genome Engineering." Cell 157, 1262-1278 (2014).
Jentzmik, F., et al. "Androgen receptor aberrations in the era of abiraterone and enzalutamide." World J. Urol. 34, 297-303 (2016).
Kalin, J. H. & Bergman, J. A. "Development and therapeutic implications of selective histone deacetylase 6 inhibitors." Journal of Medicinal Chemistry 56, 6297-6313 (2013).
Kasoji, S. K. et al. "Cavitation enhancing nanodroplets mediate efficient DNA fragmentation in a bench top ultrasonic water bath." PLoS One 10, (2015).
Kelly, R. D. W. & Cowley, S. M. "The physiological roles of histone deacetylase (HDAC) 1 and 2: complex co-stars with multiple leading parts." Biochem. Soc. Trans. 41, 741-9 (2013).
Kim, W. et al. "Targeted disruption of the EZH2-EED complex inhibits EZH2-dependent cancer." Nat. Chem. Biol. 9, 643-650 (2013).
Knudsen, K. E. & Penning, T. M. "Partners in crime: deregulation of AR activity and androgen synthesis in prostate cancer." Trends Endocrinol. Metab. 21, 315-324 (2010).
Komor, A. C., et al. "CRISPR-Based Technologies for the Manipulation of Eukaryotic Genomes." Cell 168, 20-36 (2017).
Kungulovski, G. & Jeltsch, A. "Epigenome Editing: State of the Art, Concepts, and Perspectives." Trends in Genetics 32, 101-113 (2016).
Lahm, A et al. "Unraveling the hidden catalytic activity of vertebrate class IIa histone deacetylases." Proc. Natl. Acad. Sci. U. S. A. 104, 17335-40 (2007).
Lanphier, E., et al. "Don't edit the human germ line." Nature 519, 410-411 (2015).
Lee et al., "Studies on a Dithiane—Protected Benzoin Photolabile Safety Catch Linker for Solid-Phase Synthesis." J. Org. Chem. 64:3454-3460, 1999.
Lewis, K. M. & Ke, A. "Building the Class 2 CRISPR-Cas Arsenal." Mol. Cell 65, 377-379 (2017).
Liszczak, G. P. et al. "Genomic targeting of epigenetic probes using a chemically tailored Cas9 system." PNAS 114, 681-686 (2017).
MacDonald, I. A. & Hathaway, N. A. "Epigenetic roots of immunologic disease and new methods for examining chromatin regulatory pathways." Immunol. Cell Biol. 93, 261-270 (2015).
Mali, P. et al. CAS9 transcriptional activators for target specificity screening and paired nickases for cooperative genome engineering. Nat. Biotechnol. 31, 833-838 (2013).
Marks, P. "Discovery and development of SAHA as an anticancer agent." Oncogene 26, 1351-1356 (2007).
Mills, I. G. "Maintaining and reprogramming genomic androgen receptor activity in prostate cancer." Nat. Publ. Gr. 14, 187-198 (2014).
Nelson, P. S. "Molecular states underlying androgen receptor activation: a framework for therapeutics targeting androgen signaling in prostate cancer." J. Clin. Oncol. 30, 644-646 (2012).
Oudard, S. Progress in emerging therapies for advanced prostate cancer. Cancer Treat. Rev. 39, 275-289 (2013).
Ousterout, D. G. et al. "Multiplex CRISPR/Cas9-based genome editing for correction of dystrophin mutations that cause Duchenne muscular dystrophy." Nat. Commun. 6, 6244 (2015).
Peart, M. J. et al. "Identification and functional significance of genes regulated by structurally different histone deacetylase inhibitors." Proc. Natl. Acad. Sci. U. S. A. 102, 3697-3702 (2005).
Qi, L. S. et al. "Repurposing CRISPR as an RNA-guided platform for sequence-specific control of gene expression." Cell 152, 1173-1183 (2013).
Rai, M. et al. "Two new pimelic diphenylamide HDAC inhibitors induce sustained frataxin upregulation in cells from Friedreich's ataxia patients and in a mouse model." PLoS One 5, (2010).
Robinson, D. et al. "Integrative clinical genomics of advanced prostate cancer." Cell 161, 1215-1228 (2015).
Ryan, C. J. et al. "Abiraterone in Metastatic Prostate Cancer without Previous Chemotherapy." N. Engl. J. Med. 368, 138-148 (2013).
Scher, H. I. et al. "Antitumour activity of MDV3100 in castration-resistant prostate cancer: a phase 1-2 study." Lancet (London, England) 375, 1437-1446 (2010).
Scher, H. I. et al. "Increased survival with enzalutamide in prostate cancer after chemotherapy." N. Engl. J. Med. 367, 1187-1197 (2012).
Seto, E. & Yoshida, M. "Erasers of histone acetylation: The histone deacetylase enzymes." Cold Spring Harb. Perspect. Biol. 6, (2014).
Siegel, R. L., et al. Cancer Statistics, 2017. CA. Cancer J. Clin. 67, 7-30 (2017).
Subramanian, S., et al. "Clinical toxicities of histone deacetylase inhibitors." Pharmaceuticals 3, 2751-2767 (2010).
Sun, Z. et al. "Deacetylase-Independent function of HDAC3 in transcription and metabolism requires nuclear receptor corepressor." Mol. Cell 52, 769-782 (2013).
Tanenbaum, M. E., et al. "A Protein-Tagging System for Signal Amplification in Gene Expression and Fluorescence Imaging." Cell 159, 635-646 (2014).
Lonergan, P. & Tindall, D., "Androgen receptor signaling in prostate cancer development and progression." J. Carcinog. 10, 20 (2011).
Urvalek, A. M. & Gudas, L. J. "Retinoic acid and histone deacetylases regulate epigenetic changes in embryonic stem cells." J. Biol. Chem. 289, 19519-19530 (2014).
Van Royen, M. E., et al. "Stepwise androgen receptor dimerization." J. Cell Sci. 125, 1970-1979 (2012).
Wagner, F. F. et al. "Kinetically Selective Inhibitors of Histone Deacetylase 2 (HDAC2) as Cognition Enhancers." Chem. Sci. 6, 804-815 (2015).
Wang, Q. et al. "Androgen Receptor Regulates a Distinct Transcription Program in Androgen- Independent Prostate Cancer." Cell 138, 245-256 (2009).
Watson, P. A., et al. "Emerging mechanisms of resistance to androgen receptor inhibitors in prostate cancer." Nat. Publ. Gr. 15, 701-711 (2015).
Xiao, X., et al. "A Cell-Permeable Synthetic Transcription Factor Mimic." Angew. Chemie Int. Ed. 46, 2865-2868 (2007).
You, S.-H. et al. "Nuclear receptor co-repressors are required for the histone-deacetylase activity of HDAC3 in vivo." Nat. Struct. Mol. Biol. 20, 182-187 (2013).
Zalatan, J. G. et al. "Engineering Complex Synthetic Transcriptional Programs with CRISPR RNA Scaffolds." Cell 160, 339-350 (2014).
Zhang, J., et al. "The N-CoR-HDAC3 nuclear receptor corepressor complex inhibits the JNK pathway through the integral subunit GPS2." Mol. Cell 9, 611-623 (2002).
Zhang, H., et al. "Uncoupling Transcription from Covalent Histone Modification." PLoS Genet. 10, (2014).
Zhou, et al. "Charting histone modifications and the functional organization of mammalian genomes." Nat. Rev. Genet. 12, 7-18 (2011).
Zwergel, C., et al. "Histone Deacetylase Inhibitors : Updated Studies in Various Epigenetic—Related Diseases." J. Clin. Epigenetics 2, 1-15 (2016).
International Search Report and Written Opinion dated Nov. 29, 2018 by the International Searching Authority for International Application No. PCT/US2018/045266, filed on Aug. 3, 2018 and published as WO/2019/028426 on Feb. 7, 2019 (Applicant-THE University of North Carolina At Chapel Hill) (13 Pages).

(56) References Cited

OTHER PUBLICATIONS

U.S. Appl. No. 62/541,343, filed Aug. 4, 2017, Nate Hathaway.
U.S. Appl. No. 62/654,958, filed Apr. 9, 2018, Nate Hathaway.
PCT/US2018/045266 (WO 2019/028426), filed Aug. 3, 2018 (Feb. 7, 2019), Nate Hathaway (University of North Caroline at Chapel Hill).

* cited by examiner

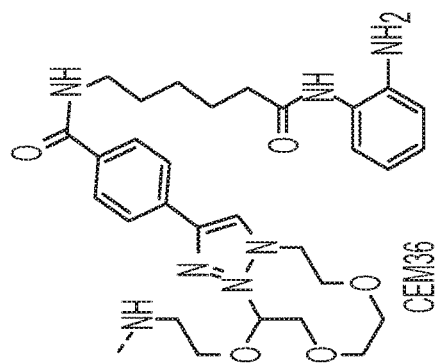
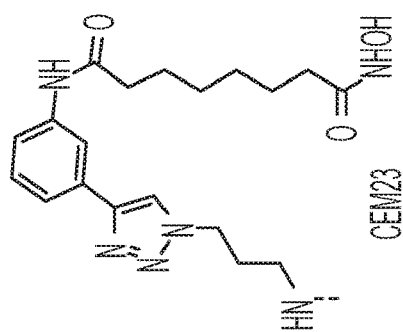
LINKER - HDAC INHIBITOR R GROUPS:
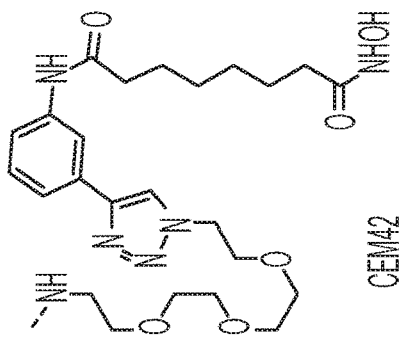
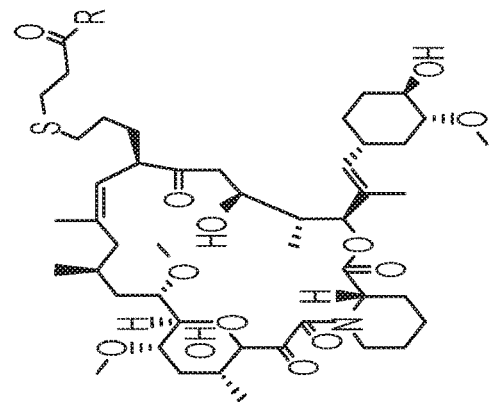
FIG. 1B

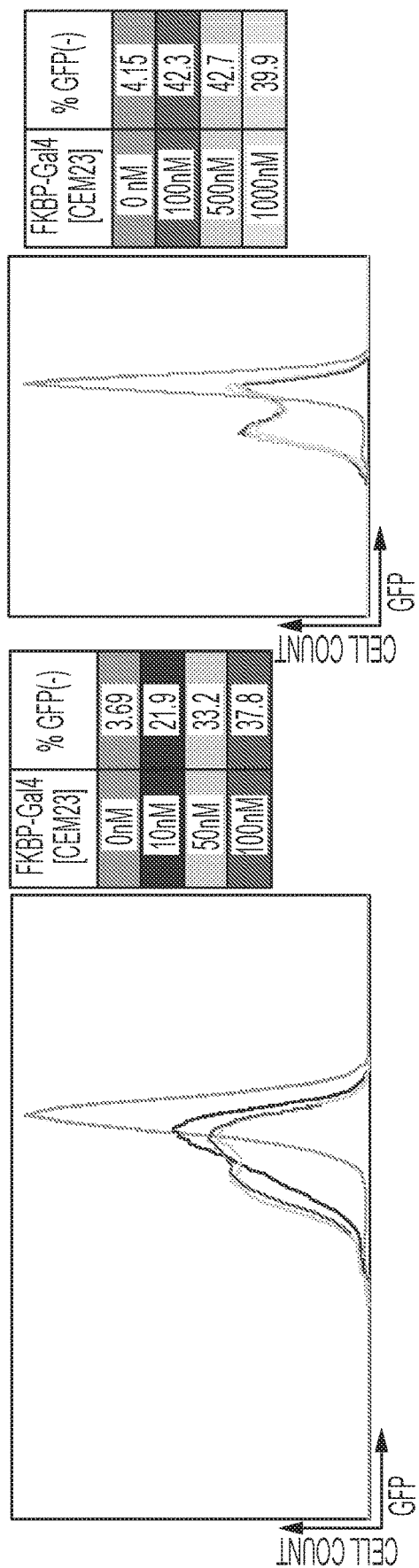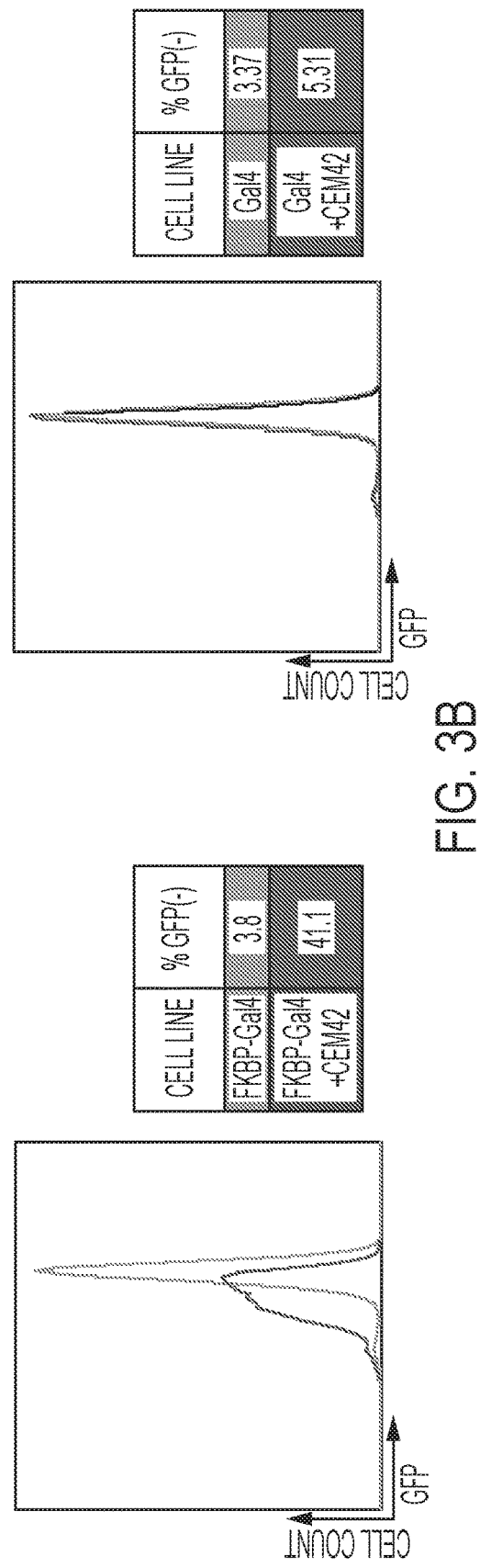
FIG. 3A
FIG. 3B

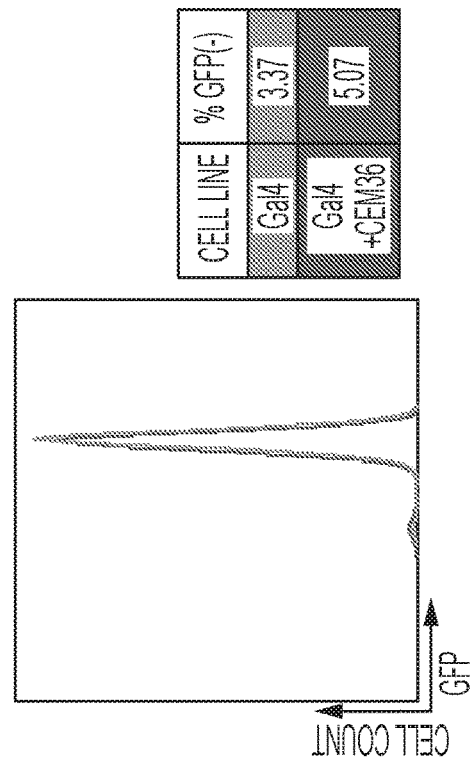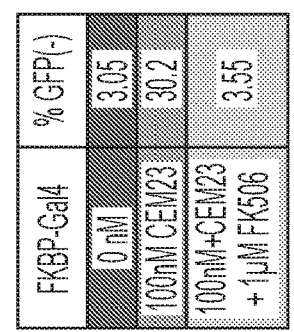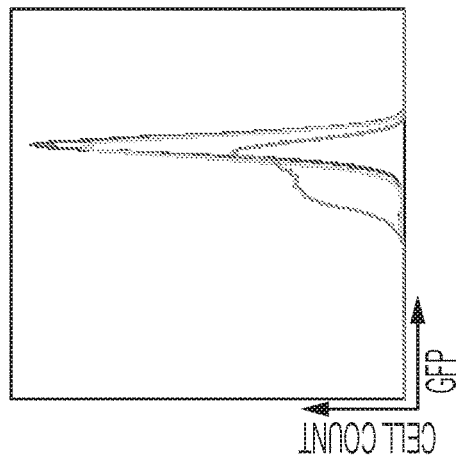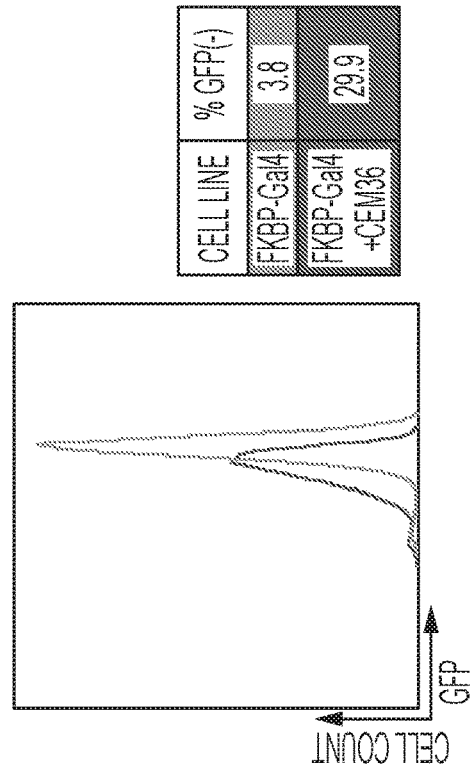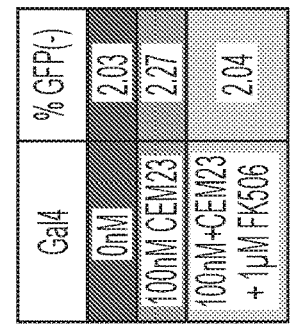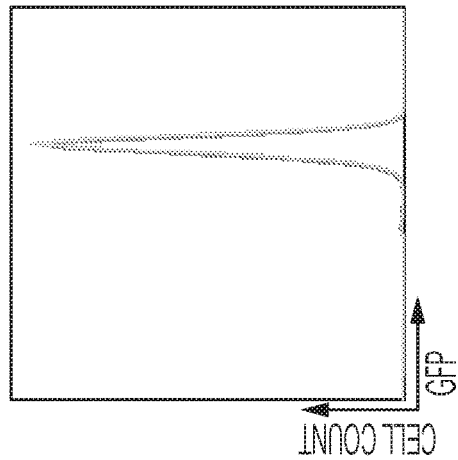
FIG. 3C
FIG. 3D

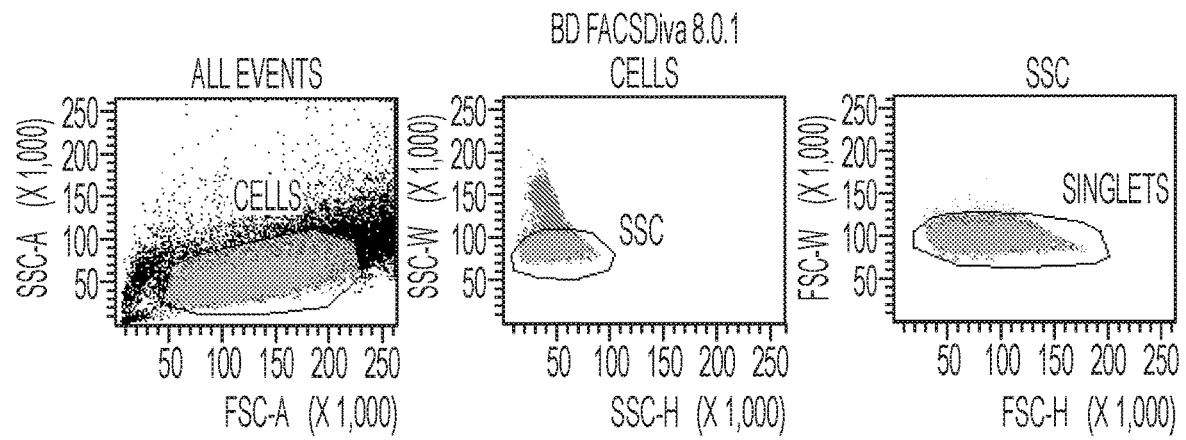
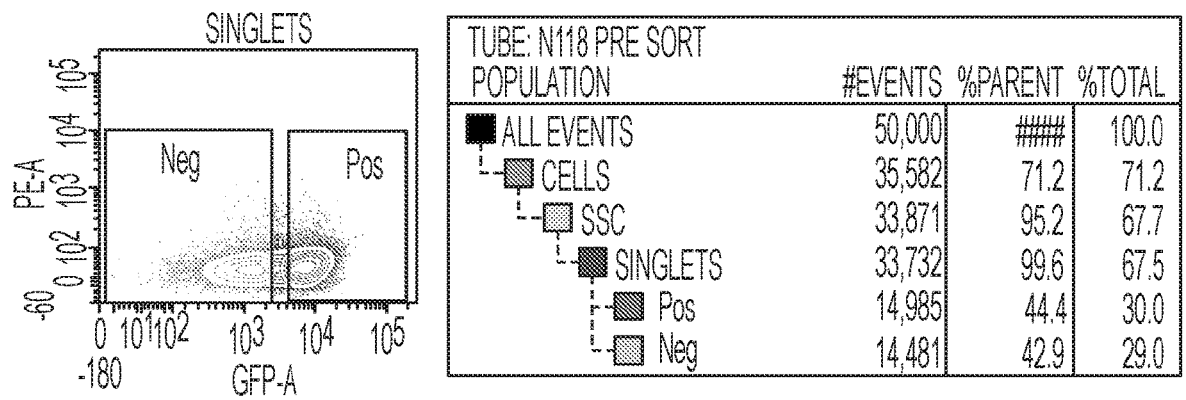
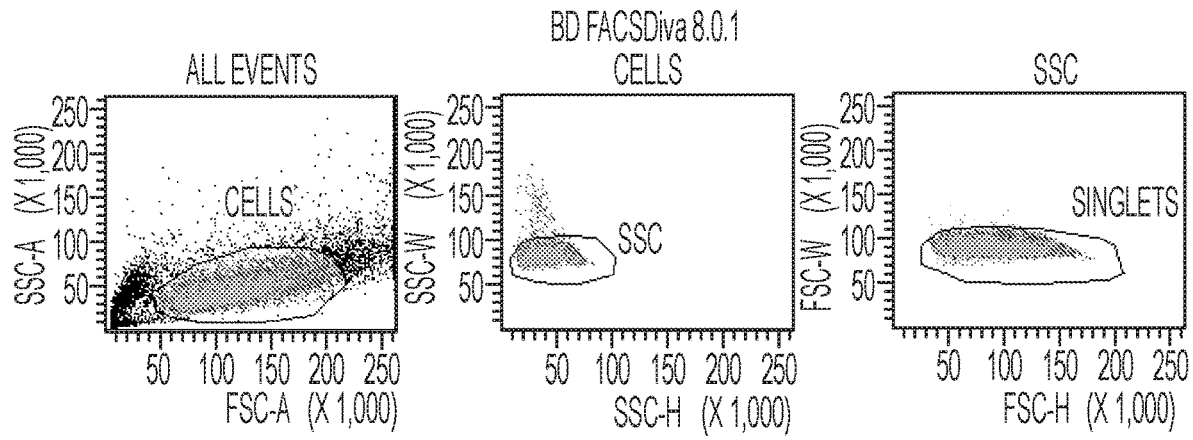
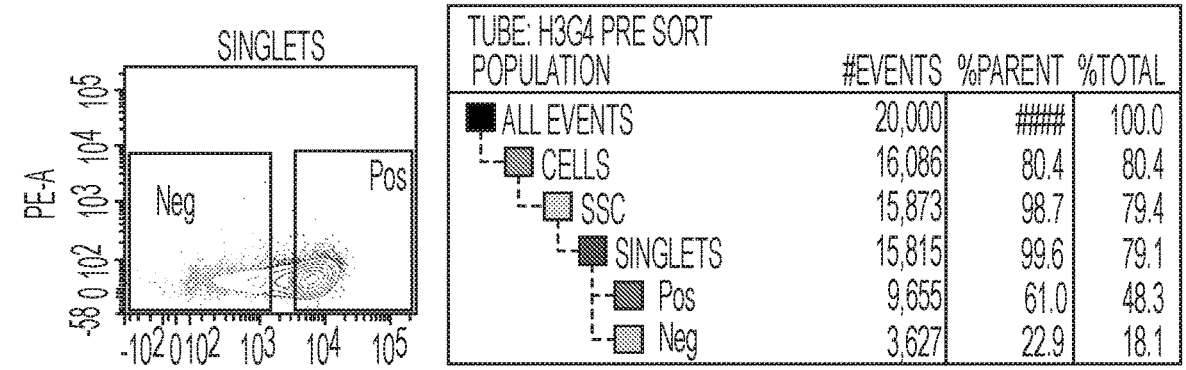
FIG. 4B

| 15-NOV | FKBP-Gal4 48hrs | | | | | | |
|---|---|---|---|---|---|---|---|
| | CONTROL-ON | CONTROL-OFF | CONTROL-VAR | cem23-ON | cem23-OFF | cem23-VAR | cem42-ON |
| TOTAL FOR EACH CATEGORY | 163 | 5 | 5 | 64 | 53 | 35 | 76 |
| TOTAL FOR THE CELL LINE | | | 173 | | | 152 | |
| % | 0.942 | 0.029 | 0.029 | 0.421 | 0.349 | 0.230 | 0.507 |
| %x100 | 94.22 | 2.89 | 2.89 | 42.11 | 34.87 | 23.03 | 50.67 |
| | Gal4 48hrs | | | | | | |
| | Fk506-ON | Fk506-OFF | Fk506-VAR | H3G4-ON | H3G4-OFF | H3G4-VAR | CONTROL-ON |
| TOTAL FOR EACH CATEGORY | 179 | 7 | 5 | 82 | 56 | 55 | 176 |
| TOTAL FOR THE CELL LINE | | | 191 | | | 193 | |
| % | 0.937 | 0.037 | 0.026 | 0.425 | 0.290 | 0.285 | 0.941 |
| %x100 | 93.72 | 3.66 | 2.62 | 42.49 | 29.02 | 28.50 | 94.12 |
| 15-NOV | Gal4 48hrs | | | | | | |
| | cem23-ON | cem23-OFF | cem23-VAR | Fk506-ON | Fk506-OFF | Fk506-VAR | CONTROL-ON |
| TOTAL FOR EACH CATEGORY | 168 | 7 | 7 | 170 | 5 | 7 | 138 |
| TOTAL FOR THE CELL LINE | | | 182 | | | 182 | |
| % | 0.923 | 0.038 | 0.038 | 0.934 | 0.027 | 0.038 | 0.926 |
| %x100 | 92.31 | 3.85 | 3.85 | 93.41 | 2.75 | 3.85 | 92.62 |

FIG. 6

| cem42-OFF | cem42-VAR | cem36-ON | cem36-OFF | cem36-VAR | Fk506-ON | Fk506-OFF | Fk506-VAR |
|---|---|---|---|---|---|---|---|
| 43 | 31 | 96 | 44 | 20 | 154 | 6 | 5 |
|  | 150 |  |  | 160 |  |  | 165 |
| 0.287 | 0.207 | 0.600 | 0.275 | 0.125 | 0.933 | 0.036 | 0.030 |
| 28.67 | 20.67 | 60.00 | 27.50 | 12.50 | 93.33 | 3.64 | 3.03 |

| CONTROL-OFF | CONTROL-VAR | cem42-ON | cem42-OFF | cem42-VAR | cem36-ON | cem36-OFF | cem36-VAR | cem23-ON | cem23-OFF | cem23-VAR |
|---|---|---|---|---|---|---|---|---|---|---|
| 2 | 9 | 200 | 5 | 8 | 182 | 5 | 8 | 171 | 4 | 8 |
|  | 187 |  |  | 213 |  |  | 195 |  |  | 183 |
| 0.011 | 0.048 | 0.939 | 0.023 | 0.038 | 0.933 | 0.026 | 0.041 | 0.934 | 0.022 | 0.044 |
| 1.07 | 4.81 | 93.90 | 2.35 | 3.76 | 93.33 | 2.56 | 4.10 | 93.44 | 2.19 | 4.37 |

| CONTROL-OFF | CONTROL-VAR | cem42-ON | cem42-OFF | cem42-VAR | H3G4-ON | H3G4-OFF | H3G4-VAR | cem36-ON | cem36-OFF | cem36-VAR |
|---|---|---|---|---|---|---|---|---|---|---|
| 5 | 6 | 189 | 4 | 10 | 90 | 46 | 73 | 175 | 4 | 9 |
|  | 149 |  |  | 203 |  |  | 209 |  |  | 189 |
| 0.034 | 0.040 | 0.931 | 0.020 | 0.049 | 0.431 | 0.220 | 0.349 | 0.931 | 0.021 | 0.048 |
| 3.36 | 4.03 | 93.10 | 1.97 | 4.93 | 43.06 | 22.01 | 34.93 | 93.12 | 2.12 | 4.76 |

FIG. 6 CONTINUED

| 19-NOV | FKBP-Gal4 48hrs | | | | | | |
|---|---|---|---|---|---|---|---|
| | Fk506-ON | Fk506-OFF | Fk506-VAR | cem23-ON | cem23-OFF | cem23-VAR | cem42-ON |
| TOTAL FOR EACH CATEGORY | 159 | | 2 | 77 | 53 | 47 | 88 |
| TOTAL FOR THE CELL LINE | | | 169 | | | 177 | |
| % | 0.941 | 0.012 | 0.047 | 0.435 | 0.289 | 0.266 | 0.506 |
| %x100 | 94.08 | 1.18 | 4.73 | 43.50 | 29.94 | 26.55 | 50.57 |

COMBINED DATA FOR AVERAGE AND STANDARD DEVIATION CALCULATION

| Gal4 CONSTRUCT | Gal4: CON | Gal4: FK506 | Gal4: CEM | Gal4: CEM | Gal4: CEM | HD AC3-Gal4 |
|---|---|---|---|---|---|---|
| GFP ON | 94.12 | 93.72 | 93.44 | 93.33 | 93.90 | 42.49 |
| GFP ON | 92.62 | 93.41 | 92.31 | 93.12 | 93.10 | 43.06 |
| AVERAGE | 93.37 | 93.57 | 92.88 | 93.23 | 93.50 | 42.78 |
| STD DEV | 1.06 | 0.22 | 0.80 | 0.15 | 0.57 | 0.40 |
| GFP OFF | 1.07 | 3.66 | 2.19 | 2.56 | 2.35 | 29.02 |
| GFP OFF | 3.36 | 2.75 | 3.85 | 2.12 | 1.97 | 22.01 |
| AVERAGE | 2.22 | 3.21 | 3.02 | 2.34 | 2.16 | 25.52 |
| STD DEV | 1.62 | 0.64 | 1.17 | 0.31 | 0.27 | 4.96 |
| VARIEGATED | 4.81 | 2.62 | 4.37 | 4.10 | 3.76 | 28.50 |
| VARIEGATED | 4.03 | 3.85 | 3.85 | 4.76 | 4.93 | 34.93 |
| AVERAGE | 4.42 | 3.24 | 4.11 | 4.43 | 4.35 | 31.72 |
| STD DEV | 0.55 | 0.87 | 0.37 | 0.47 | 0.83 | 4.55 |

FIG. 6 CONTINUED

| cem42-OFF | cem42-VAR | cem36-ON | cem36-OFF | cem36-VAR | CONTROL-ON | CONTROL-OFF | CONTROL-VAR |
|---|---|---|---|---|---|---|---|
| 52 | 34 | 90 | 28 | 35 | 138 | 3 | 6 |
|  | 174 |  |  | 153 |  |  | 147 |
| 0.299 | 0.195 | 0.588 | 0.183 | 0.229 | 0.939 | 0.020 | 0.041 |
| 29.89 | 19.54 | 58.82 | 18.30 | 22.88 | 93.88 | 2.04 | 4.08 |

| FKBP-Gal4 | F-G4:CONTROL | F-G4:Fk506 | F-G4:Cem23 | F-G4:Cem36 | F-G4:Cem42 |
|---|---|---|---|---|---|
| GFP ON | 93.88 | 94.08 | 43.50 | 58.82 | 50.57 |
| GFP ON | 94.22 | 93.33 | 42.11 | 60.00 | 50.67 |
| AVERAGE | 94.05 | 93.71 | 42.81 | 59.41 | 50.62 |
| STD DEV | 0.24 | 0.53 | 0.98 | 0.83 | 0.07 |
| GFP OFF | 2.04 | 1.16 | 29.94 | 18.30 | 29.89 |
| GFP OFF | 2.89 | 3.64 | 34.87 | 27.50 | 28.67 |
| AVERAGE | 2.47 | 2.41 | 32.41 | 22.90 | 29.28 |
| STD DEV | 0.60 | 1.74 | 3.48 | 6.50 | 0.86 |
| VARIEGATED | 4.08 | 4.73 | 26.55 | 22.88 | 19.54 |
| VARIEGATED | 2.89 | 3.03 | 23.03 | 12.50 | 20.67 |
| AVERAGE | 3.49 | 3.88 | 24.79 | 17.69 | 20.11 |
| STD DEV | 0.84 | 1.20 | 2.49 | 7.34 | 0.80 |

FIG. 6 CONTINUED

| CELL LINE: | MEDIAN FLUORESCENCE VALUE: | REFERENCING FROM FIGURE: |
|---|---|---|
| FKBP-Gal4 CONTROL | 47613 | FIGURE 2C AND FIGURE 3B AND 3C |
| FKBP-Gal4 + CEM23 24hrs | 23968 | FIGURE 2C |
| FKBP-Gal4 + CEM23 48hrs | 15024 | FIGURE 2C |
| FKBP-Gal4 + CEM23 72hrs | 14022 | FIGURE 2C |
| FKBP-Gal4 + CEM36 48hrs | 22098 | FIGURE 3C |
| FKBP-Gal4 + CEM42 48hrs | 17964 | FIGURE 3B |
| Gal4 CONTROL | 48590 | FIGURE 2B AND FIGURE 3B AND 3C |
| Gal4 + CEM23 72hrs | 44981 | FIGURE 2B |
| Gal4 + CEM36 72hrs | 46091 | FIGURE 3C |
| Gal4 + CEM42 72hrs | 44077 | FIGURE 3C |
| SORTED NEGATIVE POPULATION + CEM23 FOR 3 DAYS | 6973 | FIGURE 2D |
| SORTED NEGATIVE POPULATION - CEM23 FOR 3 DAYS | 51852 | FIGURE 2D |
| SORTED NEGATIVE POPULATION + CEM23 FOR 5 DAYS | 6377 | FIGURE 2D |
| SORTED NEGATIVE POPULATION - CEM23 FOR 5 DAYS | 44617 | FIGURE 2D |
| SORTED NEGATIVE POPULATION - CEM23 FOR 5 DAYS THEN + CEM23 FOR 2 DAYS | 8371 | FIGURE 2D |
| SORTED NEGATIVE POPULATION - CEM23 FOR 7 DAYS | 52916 | FIGURE 2D |
| Gal4 CONTROL (WITH HDAC3 EXPERIMENT) | 47807 | FIGURE 2A |
| HDAC3-Gal4 | 18861 | FIGURE 2A |
| FKBP-Gal4 CONTROL (FOR LOWER CONCENTRATIONS) | 46656 | FIGURE 3A |
| FKBP-Gal4 + 10nM CEM23 | 22460 | FIGURE 3A |
| FKBP-Gal4 + 50nM CEM23 | 15775 | FIGURE 3A |
| FKBP-Gal4 + 100nM CEM23 | 14194 | FIGURE 3A |
| FKBP-Gal4 CONTROL (FOR HIGHER CONCENTRATIONS) | 47036 | FIGURE 3A |
| FKBP-Gal4 + 100nM CEM23 | 12515 | FIGURE 3A |
| FKBP-Gal4 + 500nM CEM23 | 11871 | FIGURE 3A |
| FKBP-Gal4 + 1000nM CEM23 | 14194 | FIGURE 3A |
| Gal4 CONTROL | 52916 | FIGURE 3D |
| Gal4 + 100nM CEM23 | 47807 | FIGURE 3D |
| Gal4 + 100nM CEM23 + 1µM FK506 | 52701 | FIGURE 3D |
| FKBP-Gal4 CONTROL | 51642 | FIGURE 3D |
| FKBP-Gal4 + 100nM CEM23 | 19643 | FIGURE 3D |
| FKBP-Gal4 + 100nM CEM23 + 1µM FK506 | 45164 | FIGURE 3D |

FIG. 12

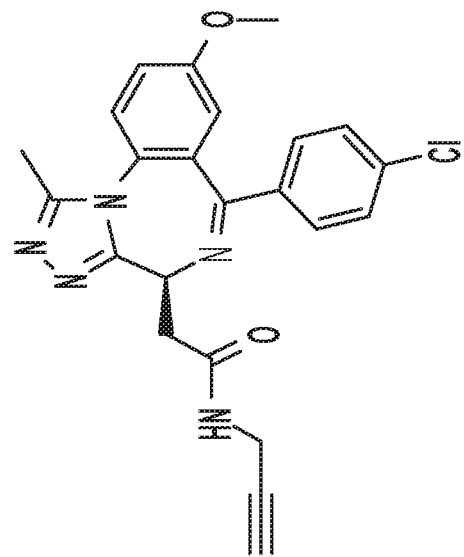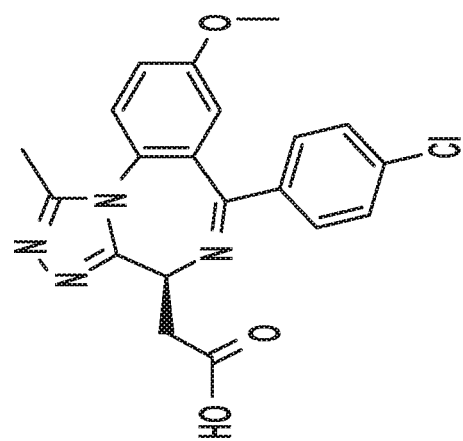
FIG. 20A

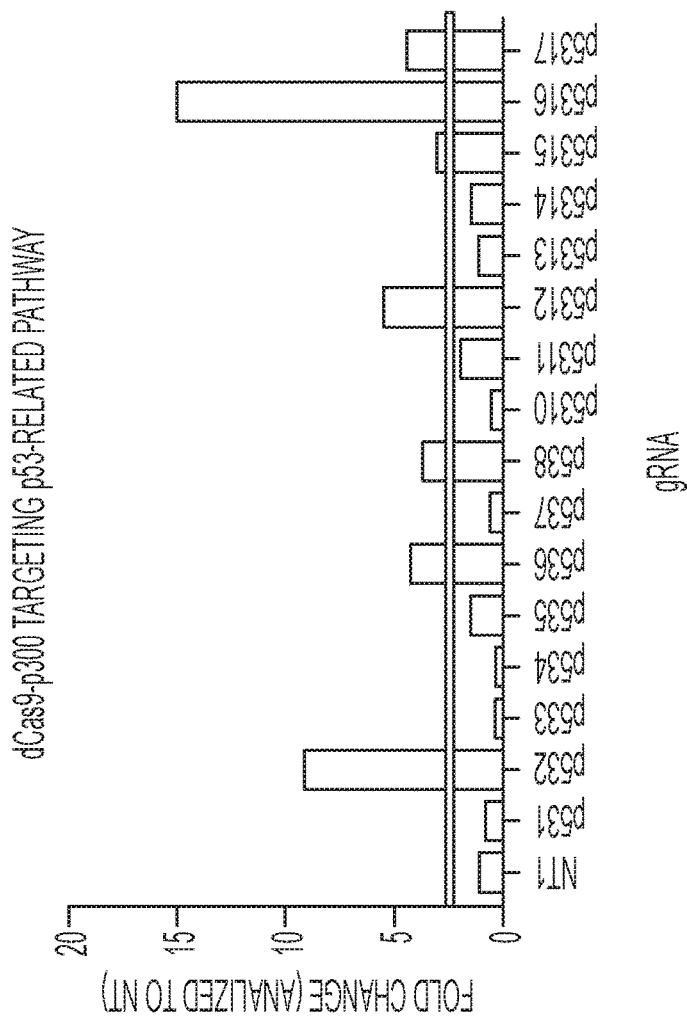
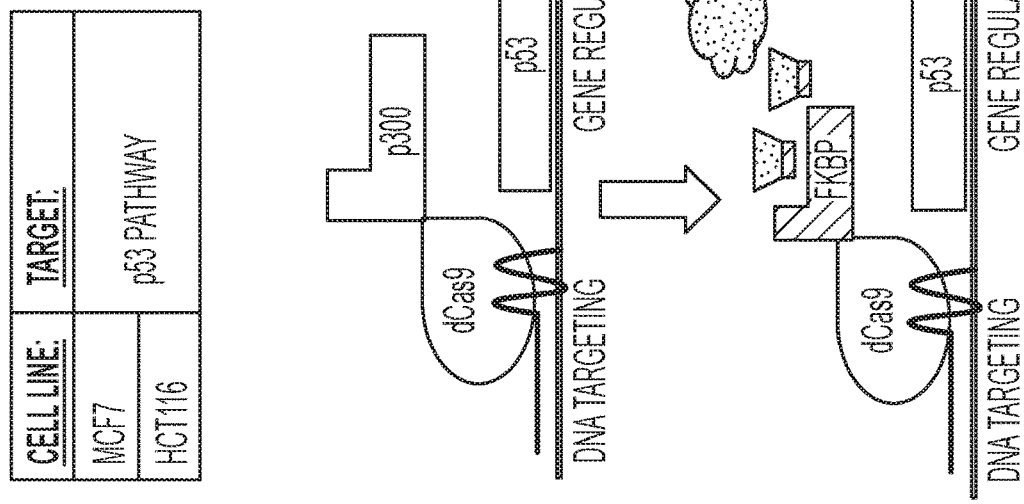
FIG. 31

SEQUENCE LISTING

<160> NUMBER OF SEQ ID NOS: 42

<210> SEQ ID NO 1
<211> LENGTH: 41
<212> TYPE: DNA
<213> ORGANISM: Artificial Sequence
<220> FEATURE:
<223> OTHER INFORMATION: Synthetic construct

<400> SEQUENCE: 1
tgaggatccg cggccgcgcc accatggcca agaccgtggc g                41

<210> SEQ ID NO 2
<211> LENGTH: 50
<212> TYPE: DNA
<213> ORGANISM: Artificial Sequence
<220> FEATURE:
<223> OTHER INFORMATION: Synthetic construct

<400> SEQUENCE: 2
cgacaaggaa agtgatgtgg agattatgaa gctactgtct tctatcgaac          50

<210> SEQ ID NO 3
<211> LENGTH: 50
<212> TYPE: DNA
<213> ORGANISM: Artificial Sequence
<220> FEATURE:
<223> OTHER INFORMATION: Synthetic construct

<400> SEQUENCE: 3
gttcgataga agacagtagc ttcataatct ccacatcact ttccttgtcg          50

<210> SEQ ID NO 4
<211> LENGTH: 44
<212> TYPE: DNA
<213> ORGANISM: Artificial Sequence
<220> FEATURE:
<223> OTHER INFORMATION: Synthetic construct

<400> SEQUENCE: 4
agagccggcg cggccgccta cgatacagtc aactgtcttt gacc                44

<210> SEQ ID NO 5
<211> LENGTH: 23
<212> TYPE: DNA
<213> ORGANISM: Artificial Sequence
<220> FEATURE:
<223> OTHER INFORMATION: Synthetic construct

<400> SEQUENCE: 5
ctagaggatc cgaggaccaa ttg                                       23

<210> SEQ ID NO 6
<211> LENGTH: 20
<212> TYPE: DNA
<213> ORGANISM: Artificial Sequence
<220> FEATURE:
<223> OTHER INFORMATION: Synthetic construct

<400> SEQUENCE: 6
accttcaagg tcctctcacc                                           20

<210> SEQ ID NO 7
<211> LENGTH: 20
<212> TYPE: DNA
<213> ORGANISM: Artificial Sequence -continued
<220> FEATURE:
<223> OTHER INFORMATION: Synthetic construct

<400> SEQUENCE: 7
cacatgaagc agcacgactt                                          20

<210> SEQ ID NO 8
<211> LENGTH: 20
<212> TYPE: DNA
<213> ORGANISM: Artificial Sequence
<220> FEATURE:
<223> OTHER INFORMATION: Synthetic construct

<400> SEQUENCE: 8
ccttgaagaa gatggtgcgc                                          20

<210> SEQ ID NO 9
<211> LENGTH: 20
<212> TYPE: DNA
<213> ORGANISM: Artificial Sequence
<220> FEATURE:
<223> OTHER INFORMATION: Synthetic construct

<400> SEQUENCE: 9
cacatggtcc tgctggagtt                                          20

<210> SEQ ID NO 10
<211> LENGTH: 18
<212> TYPE: DNA
<213> ORGANISM: Artificial Sequence
<220> FEATURE:
<223> OTHER INFORMATION: Synthetic construct

<400> SEQUENCE: 10
atctagagtc gcggccgg                                            18

<210> SEQ ID NO 11
<211> LENGTH: 19
<212> TYPE: DNA
<213> ORGANISM: Artificial Sequence
<220> FEATURE:
<223> OTHER INFORMATION: Synthetic construct

<400> SEQUENCE: 11
gtgatgggtc agcagggct                                           19

<210> SEQ ID NO 12
<211> LENGTH: 19
<212> TYPE: DNA
<213> ORGANISM: Artificial Sequence
<220> FEATURE:
<223> OTHER INFORMATION: Synthetic construct

<400> SEQUENCE: 12
tccgattcca ggcccacct                                           19

<210> SEQ ID NO 13
<211> LENGTH: 20
<212> TYPE: DNA
<213> ORGANISM: Artificial Sequence
<220> FEATURE:
<223> OTHER INFORMATION: Synthetic construct

<400> SEQUENCE: 13
ttacttcgtg tctgtcgggg                                          20

<210> SEQ ID NO 14
<211> LENGTH: 22
<212> TYPE: DNA
<213> ORGANISM: Artificial Sequence
<220> FEATURE:
<223> OTHER INFORMATION: Synthetic construct

<400> SEQUENCE: 14
gagagtaaag tcagagaggc ca                                          22

<210> SEQ ID NO 15
<211> LENGTH: 36
<212> TYPE: DNA
<213> ORGANISM: Artificial Sequence
<220> FEATURE:
<223> OTHER INFORMATION: Synthetic construct

<400> SEQUENCE: 15
ggcggccgct ggatccggcg tgcaggtgga gactat                           36

<210> SEQ ID NO 16
<211> LENGTH: 40
<212> TYPE: DNA
<213> ORGANISM: Artificial Sequence
<220> FEATURE:
<223> OTHER INFORMATION: Synthetic construct

<400> SEQUENCE: 16
ctccactgcc tgtacattcc agttttagaa gctccacatc                       40

<210> SEQ ID NO 17
<211> LENGTH: 40
<212> TYPE: DNA
<213> ORGANISM: Artificial Sequence
<220> FEATURE:
<223> OTHER INFORMATION: Synthetic construct

<400> SEQUENCE: 17
ctccactgcc tgtacattcc agttttagaa gctccacatc                       40

<210> SEQ ID NO 18
<211> LENGTH: 38
<212> TYPE: DNA
<213> ORGANISM: Artificial Sequence
<220> FEATURE:
<223> OTHER INFORMATION: Synthetic construct

<400> SEQUENCE: 18
ggcggccgct ggatccgggg tccaagttga aaccatta                         38

<210> SEQ ID NO 19
<211> LENGTH: 48
<212> TYPE: DNA
<213> ORGANISM: Artificial Sequence
<220> FEATURE:
<223> OTHER INFORMATION: Synthetic construct

<400> SEQUENCE: 19
ggtccgatgg atctacagcg gccgggtgga ggtccaaaaa agaaaagg              48

<210> SEQ ID NO 20
<211> LENGTH: 37
<212> TYPE: DNA
<213> ORGANISM: Artificial Sequence
<220> FEATURE:
<223> OTHER INFORMATION: Synthetic construct

```
<400> SEQUENCE: 20
cagtgatcga tccctgcagg gcggggaggc ggcccaa                              37

<210> SEQ ID NO 21
<211> LENGTH: 38
<212> TYPE: DNA
<213> ORGANISM: Artificial Sequence
<220> FEATURE:
<223> OTHER INFORMATION: Synthetic construct

<400> SEQUENCE: 21
ggccactagt ctctggagac gaaacgtctc tctagccc                             38

<210> SEQ ID NO 22
<211> LENGTH: 38
<212> TYPE: DNA
<213> ORGANISM: Artificial Sequence
<220> FEATURE:
<223> OTHER INFORMATION: Synthetic construct

<400> SEQUENCE: 22
tcgagggcta gagagacgtt tcgtctccag agactagt                             38

<210> SEQ ID NO 23
<211> LENGTH: 20
<212> TYPE: DNA
<213> ORGANISM: Artificial Sequence
<220> FEATURE:
<223> OTHER INFORMATION: Synthetic construct

<400> SEQUENCE: 23
ctctctgctc ctttgccaca                                                 20

<210> SEQ ID NO 24
<211> LENGTH: 20
<212> TYPE: DNA
<213> ORGANISM: Artificial Sequence
<220> FEATURE:
<223> OTHER INFORMATION: Synthetic construct

<400> SEQUENCE: 24
gtgctcttcg ggtttcagga                                                 20

<210> SEQ ID NO 25
<211> LENGTH: 21
<212> TYPE: DNA
<213> ORGANISM: Artificial Sequence
<220> FEATURE:
<223> OTHER INFORMATION: Synthetic construct

<400> SEQUENCE: 25
actacaccga ggaaatgggc t                                               21

<210> SEQ ID NO 26
<211> LENGTH: 22
<212> TYPE: DNA
<213> ORGANISM: Artificial Sequence
<220> FEATURE:
<223> OTHER INFORMATION: Synthetic construct

<400> SEQUENCE: 26
cccacaatgc cagttaagaa ga                                              22

<210> SEQ ID NO 27
```

```
<211> LENGTH: 19
<212> TYPE: DNA
<213> ORGANISM: Artificial Sequence
<220> FEATURE:
<223> OTHER INFORMATION: Synthetic construct

<400> SEQUENCE: 27
cgcggccaac aagaagatg                                                      19

<210> SEQ ID NO 28
<211> LENGTH: 20
<212> TYPE: DNA
<213> ORGANISM: Artificial Sequence
<220> FEATURE:
<223> OTHER INFORMATION: Synthetic construct

<400> SEQUENCE: 28
cgacgagtag gatgagaccg                                                     20

<210> SEQ ID NO 29
<211> LENGTH: 20
<212> TYPE: DNA
<213> ORGANISM: Artificial Sequence
<220> FEATURE:
<223> OTHER INFORMATION: Synthetic construct

<400> SEQUENCE: 29
caatgacccc ttcattgacc                                                     20

<210> SEQ ID NO 30
<211> LENGTH: 20
<212> TYPE: DNA
<213> ORGANISM: Artificial Sequence
<220> FEATURE:
<223> OTHER INFORMATION: Synthetic construct

<400> SEQUENCE: 30
ttgattttgg agggatctcg                                                     20

<210> SEQ ID NO 31
<211> LENGTH: 20
<212> TYPE: DNA
<213> ORGANISM: Artificial Sequence
<220> FEATURE:
<223> OTHER INFORMATION: Synthetic construct

<400> SEQUENCE: 31
tacgttctct atcactgata                                                     20

<210> SEQ ID NO 32
<211> LENGTH: 19
<212> TYPE: DNA
<213> ORGANISM: Artificial Sequence
<220> FEATURE:
<223> OTHER INFORMATION: Synthetic construct

<400> SEQUENCE: 32
tacaaacttg ggtcgaatt                                                      19

<210> SEQ ID NO 33
<211> LENGTH: 19
<212> TYPE: DNA
<213> ORGANISM: Artificial Sequence
<220> FEATURE:
<223> OTHER INFORMATION: Synthetic construct

<400> SEQUENCE: 33
```
cctgggctcc ggggcgttt                                                19

<210> SEQ ID NO 34
<211> LENGTH: 19
<212> TYPE: DNA
<213> ORGANISM: Artificial Sequence
<220> FEATURE:
<223> OTHER INFORMATION: Synthetic construct

<400> SEQUENCE: 34
ggcccctgcg gccacccccg                                               19

<210> SEQ ID NO 35
<211> LENGTH: 19
<212> TYPE: DNA
<213> ORGANISM: Artificial Sequence
<220> FEATURE:
<223> OTHER INFORMATION: Synthetic construct

<400> SEQUENCE: 35
ctccctccct gcccggtag                                                19

<210> SEQ ID NO 36
<211> LENGTH: 19
<212> TYPE: DNA
<213> ORGANISM: Artificial Sequence
<220> FEATURE:
<223> OTHER INFORMATION: Synthetic construct

<400> SEQUENCE: 36
aggtttggaa agggcgtgc                                                19

<210> SEQ ID NO 37
<211> LENGTH: 23
<212> TYPE: DNA
<213> ORGANISM: Artificial Sequence
<220> FEATURE:
<223> OTHER INFORMATION: Synthetic construct

<400> SEQUENCE: 37
gcagacgcga ggaaggaggg cgc                                           23

<210> SEQ ID NO 38
<211> LENGTH: 20
<212> TYPE: DNA
<213> ORGANISM: Artificial Sequence
<220> FEATURE:
<223> OTHER INFORMATION: Synthetic construct

<400> SEQUENCE: 38
ccgaccaccc gcaaacagca                                               20

<210> SEQ ID NO 39
<211> LENGTH: 25
<212> TYPE: DNA
<213> ORGANISM: Artificial Sequence
<220> FEATURE:
<223> OTHER INFORMATION: Synthetic construct

<400> SEQUENCE: 39
gcctctggga ggtcctgtcc ggctc                                         25

<210> SEQ ID NO 40
<211> LENGTH: 20
<212> TYPE: DNA

```
<213> ORGANISM: Artificial Sequence
<220> FEATURE:
<223> OTHER INFORMATION: Synthetic construct

<400> SEQUENCE: 40
cgggagaaag gaacgggagg                                          20

<210> SEQ ID NO 41
<211> LENGTH: 20
<212> TYPE: DNA
<213> ORGANISM: Artificial Sequence
<220> FEATURE:
<223> OTHER INFORMATION: Synthetic construct

<400> SEQUENCE: 41
tccaatttct agggtcaccg                                          20

<210> SEQ ID NO 42
<211> LENGTH: 20
<212> TYPE: DNA
<213> ORGANISM: Artificial Sequence
<220> FEATURE:
<223> OTHER INFORMATION: Synthetic construct

<400> SEQUENCE: 42
aagaacttga agcaaagcgc                                          20
```

BIFUNCTION CHEMICAL EPIGENETIC MODIFIERS AND METHODS OF USE

CROSS REFERENCE TO RELATED APPLICATIONS

This application claims the benefit of priority under 35 U.S.C. 371 of International Application No. PCT/US2018/045266, filed on Aug. 3, 2018, which claims priority to U.S. Provisional Application Nos. 62/541,343, filed on Aug. 4, 2017; and 62/654,958, filed on Apr. 9, 2018. The content of these earlier filed applications is hereby incorporated by reference herein in their entirety.

INCORPORATION OF THE SEQUENCE LISTING

The present application contains a sequence listing that was submitted in ASCII format via EFS-Web on concurrent with the filing of this application, containing the file name 37571_00010U3_SL which is 12,288 bytes in size, created on Jan. 29, 2020, and is herein incorporated by reference in its entirety pursuant to 37 C.F.R. § 1..52(e)(5).

BACKGROUND

Control of gene expression programs is important for proper mammalian development. Much of this control comes from regulation at the level of chromatin, where the presence or absence of chemical marks on DNA and histone tails regulate expression of the associated gene by directing the binding of transcription factors, corepressors, coactivators, and other biomolecules (Zhou, V. W., Goren, A. & Bernstein, B. E. *Nat. Rev. Genet.* 12, 7-18 (2011)); (Bannister, A. J. & Kouzarides, T. *Cell Res.* 21, 381-395 (2011)). These epigenetic pathways are disrupted in many human diseases including cancer (Feinberg, A. P., Koldobskiy, M. A. & Göndör, A. *Nat. Rev. Genet.* 17, 284-99 (2016)). A need exists for the development of new technologies capable of synthetically modulating epigenetic processes at individual genes or sets of genes.

SUMMARY

Disclosed herein are bifunctional chemical epigenetic modifiers (CEMs) comprising a molecule of FK506 or derivative thereof, a linker and a bifunctional ligand.

Disclosed herein are methods of recruiting effector proteins in a cell, the method comprising: a) contacting the cell with a fusion protein comprising a catalytically inactive Cas9 (dCas9) and FK506 binding protein (FKBP), wherein the catalytically inactive Cas9 (dCas9) is bound to a single guide RNA, and wherein the single guide RNA binds upstream of a target gene; b) contacting the cell with a bifunctional chemical epigenetic modifier (CEM) comprising FK506 or a derivative thereof, a linker and a bifunctional ligand; and c) binding the FKBP of the fusion protein to the FK506 or a derivative thereof of the bifunctional CEM; wherein one or more effector proteins are recruited in the cell.

Disclosed herein are methods of recruiting effector proteins in a cell, the method comprising: a) contacting the cell with a catalytically inactive Cas9 (dCas9) wherein the catalytically inactive Cas9 (dCas9) is bound to a single guide RNA, and wherein the single guide RNA binds upstream of a target gene; b) contacting the cell with FK506 binding protein (FKBP); c) contacting the cell with a bifunctional chemical epigenetic modifier (CEM) comprising FK506 or a derivative thereof, a linker and a bifunctional ligand; and d) binding the FKBP to the FK506 or a derivative thereof of the bifunctional CEM; wherein one or more effector proteins are recruited in the cell.

Disclosed herein are methods of reducing expression of a target gene in a cell, the method comprising: a) expressing a fusion protein in the cell, wherein the fusion protein comprises a catalytically inactive Cas9 (dCas9) and a FK506 binding protein (FKBP), wherein the catalytically inactive Cas9 (dCas9) is bound to a single guide RNA, wherein the single guide RNA binds upstream of a target gene; b) contacting the cell with a bifunctional chemical epigenetic modifier (CEM) comprising a FK506 or a derivative thereof, a linker and a bifunctional ligand, wherein the FK506 binds to the FKBP of the fusion protein; and c) mobilizing effector proteins to the target gene, wherein the effector genes are inhibited by the bifunctional ligand; wherein the expression of the target gene is reduced.

Disclosed herein are methods of reducing expression of a target gene in a cell, the method comprising: a) expressing a fusion protein in the cell, wherein the fusion protein comprises a catalytically inactive Cas9 (dCas9), wherein the catalytically inactive Cas9 (dCas9) is bound to a single guide RNA, wherein the single guide RNA binds a nucleic acid sequence upstream of a target gene; b) contacting the cell with FK506 binding protein (FKBP); c) contacting the cell with a bifunctional chemical epigenetic modifier (CEM) comprising a FK506 or a derivative thereof, a linker and a bifunctional ligand, wherein the FK506 binds to the FKBP of the fusion protein; and d) mobilizing effector proteins to the target gene, wherein the effector genes are inhibited by the bifunctional ligand; wherein the expression of the target gene is reduced.

Disclosed herein are methods of increasing expression of a target gene in a cell, the method comprising: a) expressing a fusion protein in the cell, wherein the fusion protein comprises a catalytically inactive Cas9 (dCas9) and a FK506 binding protein (FKBP), wherein the catalytically inactive Cas9 (dCas9) is bound to a one or more guide RNAs, wherein the one or more guide RNAs bind upstream or downstream of a target gene; b) contacting the cell with a bifunctional chemical epigenetic modifier (CEM) comprising a FK506 or a derivative thereof, a linker and a bifunctional ligand, wherein the FK506 binds to the FKBP of the fusion protein; and c) mobilizing effector proteins to the target gene, wherein the effector genes are activated by the bifunctional ligand; wherein the expression of the target gene is increased.

Disclosed herein are methods of increasing expression of a target gene in a cell, the method comprising: a) expressing a fusion protein in the cell, wherein the fusion protein comprises a catalytically inactive Cas9 (dCas9), wherein the catalytically inactive Cas9 (dCas9) is bound to one or more guide RNAs, wherein the one or more guide RNAs bind a nucleic acid sequence upstream or downstream of a target gene; b) contacting the cell with FK506 binding protein (FKBP); c) contacting the cell with a bifunctional chemical epigenetic modifier (CEM) comprising a FK506 or a derivative thereof, a linker and a bifunctional ligand, wherein the FK506 binds to the FKBP of the fusion protein; and d) mobilizing effector proteins to the target gene, wherein the effector genes are activated by the bifunctional ligand; wherein the expression of the target gene is increased.

Other features and advantages of the present compositions and methods are illustrated in the description below, the drawings, and the claims.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIGS. 1A-B show the design and structure of chemical epigenetic modifiers (CEMs).

FIG. 1A shows that a Gal4-FKBP fusion binds to a 5× Gal4 binding array at the promoter of the Cia:Oct4 locus. FIG. 1A also shows that a bivalent FK506-HDAC inhibitor binds to FKBP and recruits HDAC corepressor complexes. FIG. 1B shows the structures of exemplary CEM compounds.

FIG. 2A shows flow cytometry data for ES cells expressing either Gal4 or Gal4-HDAC3. FIG. 2B shows ES cells expressing Gal4 that were treated with either 0 or 100 nM CEM23 for 48 hours. FIG. 2C shows ES cells expressing Gal4-FKBP that were treated with CEM23 over 72 hours. FIG. 2D shows ES cells treated with 100 nM CEM23 that were sorted to keep GFP (–) cells. These cells were treated with either 0 or 100 nM CEM23 for 5 additional days, and analyzed on days 5 or 7. FIG. 2E shows CEM23 treated, GFP(–) sorted cells that were washed out for five days, treated with either 0 or 100 nM CEM23 for two days, and analyzed by flow cytometry.

FIGS. 3A-D. FIG. 3A shows overlays of histograms of dose response for CEM23 (0, 10, 50, 100, 500, 1000 nM) with legend showing colors for each dose. FIG. 3B shows overlays of histograms of CEM42+/–compound for Gal4 and Gal4-FKBP cell lines. FIG. 3C shows overlays of histograms of CEM36+/–compound for Gal4 and Gal4-FKBP cell lines. FIG. 3D shows overlays of histograms for the Gal4 cell line and FKBP-Gal4 cell line with 100 nM of CEM23, with and without 1 μM FK506.

FIGS. 4A-C shows the results of ChIP experiments. FIG. 4A shows the gating of FKBP-Gal4+100 nM CEM23 cells and gating of HDAC3-Gal4 cells for Fluorescence Activated Cell Sorting (FACS) for replicate 1 of ChIP experiments. FIG. 4B shows the gating of FKBP-Gal4+100 nM CEM23 cells and gating of HDAC3-Gal4 cells for FACS for replicate 2 of ChIP experiments. FIG. 4C shows the gating of FKBP-Gal4+100 nM CEM23 cells and gating of HDAC3-Gal4 cells for FACS for replicate 3 of ChIP experiments.

FIG. 5A shows the treatment and image schedule. Fluorescence images were taken of ES cells and colonies were characterized as being GFP On, GFP Off, or a variegated state (FIG. 5B). Representative images are shown (FIG. 5C).

FIG. 6 is a table showing the raw data of colony characterization into GFP-Off, GFP-On, GFP-Variegated of 10 experimental conditions for two replicates.

FIG. 7A shows qPCR sites and CEM treatment schedule. Quantitative RT-PCR compared Gal4 to HDAC3-Gal4 cell lines (FIG. 7B) and Gal4-FKBP cells to Gal4-FKBP with 100 nM CEM23 (FIG. 7C) using an H3K27ac antibody. Results at all four regions are summarized (FIG. 7D). Significance was calculated using Student's t test with n=4 for B and n=5 for C. * p>0.05; ** p>0.005.

FIG. 9A is a model system for testing CEMs on defined GFP gene targets. FIG. 9B shows the adaptation of the technique to the dCas9 strategy.

FIG. 10A shows the strategy of recruiting CEM to GFP reporter. FIG. 10B shows the experimental workflow. FIG. 10C shows that flow cytometry after CEM addition for 2-days demonstrates marked repression of GFP. FIG. 10D shows ChIP of H3K27ac demonstrates strong deacetylation at the target locus correlates with gene repression. Cell sorting of positive and negative cell populations demonstrates almost complete deacetylation in GFP negative cells.

FIG. 11A shows that abiraterone selectively inhibits intratumoral androgen biosynthesis by blocking CYP17A1-mediated androgen production, limiting available ligand for AR axis signaling; and enzalutamide binds to the AR ligand binding domain and antagonizes the AR, it inhibits dimerized AR translocation, and inhibits AR complex-mediated transcription by preventing DNA binding. FIG. 11B shows dCas9-FKBP and CEM-mediated regulation of the AR.

FIG. 12 shows the median fluorescence value for each cell line and experimental condition.

FIG. 19A shows the overall dCas9-CEMa strategy showing gRNAs that are designed to target a specific gene-of-interest using HEK 293T cells as a model system. A chemical linker combines this recruitment event with an interchangeable bifunctional ligand (also sometimes referred to as a "warhead"), specific activating chromatin-modifying machinery can be recruited included (FIG. 19B) BRD2, 3, 4 (FIG. 19C) BRF1 and (FIG. 19D) CBP/p300.

FIGS. 20A-D shows the chemical synthesis of a CEMa. FIG. 20A shows a procedure for a CEMa synthesis. FIG. 20B shows the chemical synthesis and NMR validation of CEM87. FIG. 20C shows the chemical synthesis and NMR validation of CEM88. FIG. 20D shows the chemical synthesis and NMR validation of CEM114.

FIG. 21A shows that as a positive control, dCas9-p300 was transfected, and showed a ~14-fold increase in BFP expression. FIG. 21B shows that dCas9-FKBPx1 was transfected and was combined with 3 different CEMa compounds that were formulated with different bifunctional ligands. (CEM87=binds Brd-2,-3,-4; CEM88=binds BRPF1 which recruits MOZ/MORF histone acetyltrransferases, CEM114=binds CBP/p300). The most effective compound was CEM87, which demonstrated ~7-fold increased expression. FIG. 21C shows dCas9 with tandem FKBP repeats and additional FKBP recruited to MS2 RNA-binding-sites introduced into the sgRNA, and added with the same CEMa set. Again, CEM87 was the most active with ~18-fold increased expression. FIG. 21D shows a dose response curve using the improved dCas0-CEMa system and the most effective CEMa, CEM87.

FIG. 27A shows that dCas9-CEMa causes ~13-fold activation of MYOD1.

FIG. 27B shows that dCas9-CEMa causes ~10-fold activation of CXCR4. FIG. 27C dCas9-CEMa causes ~22-fold activation of ASCL1.

FIG. 30A shows that as a positive control, dCas9-p300 was transfected, and showed a ~14-fold increase in BFP expression. FIG. 30B shows the mean fluorescent value when dCas9-FKBPx1 was transfected and was combined with 3 different CEMa compounds that were formulated with different bifunctional ligands.

FIG. 30C shows mean fluorescent value when comparing gRNAs. FIG. 30D shows the mean fluorescent value using the "Sun-tag" scFv-FKBP system. FIG. 30E shows dCas9 with tandem FKBP repeats and additional FKBP recruited to MS2 RNA-binding-sites introduced into the sgRNA, and added with the same CEMa set. FIG. 30F shows the dCas9-FKBP; ms2-FKBP dose curve.

FIG. 31 shows gRNA improvement in a disease model as proof of concept.

DETAILED DESCRIPTION

Figure 1A:
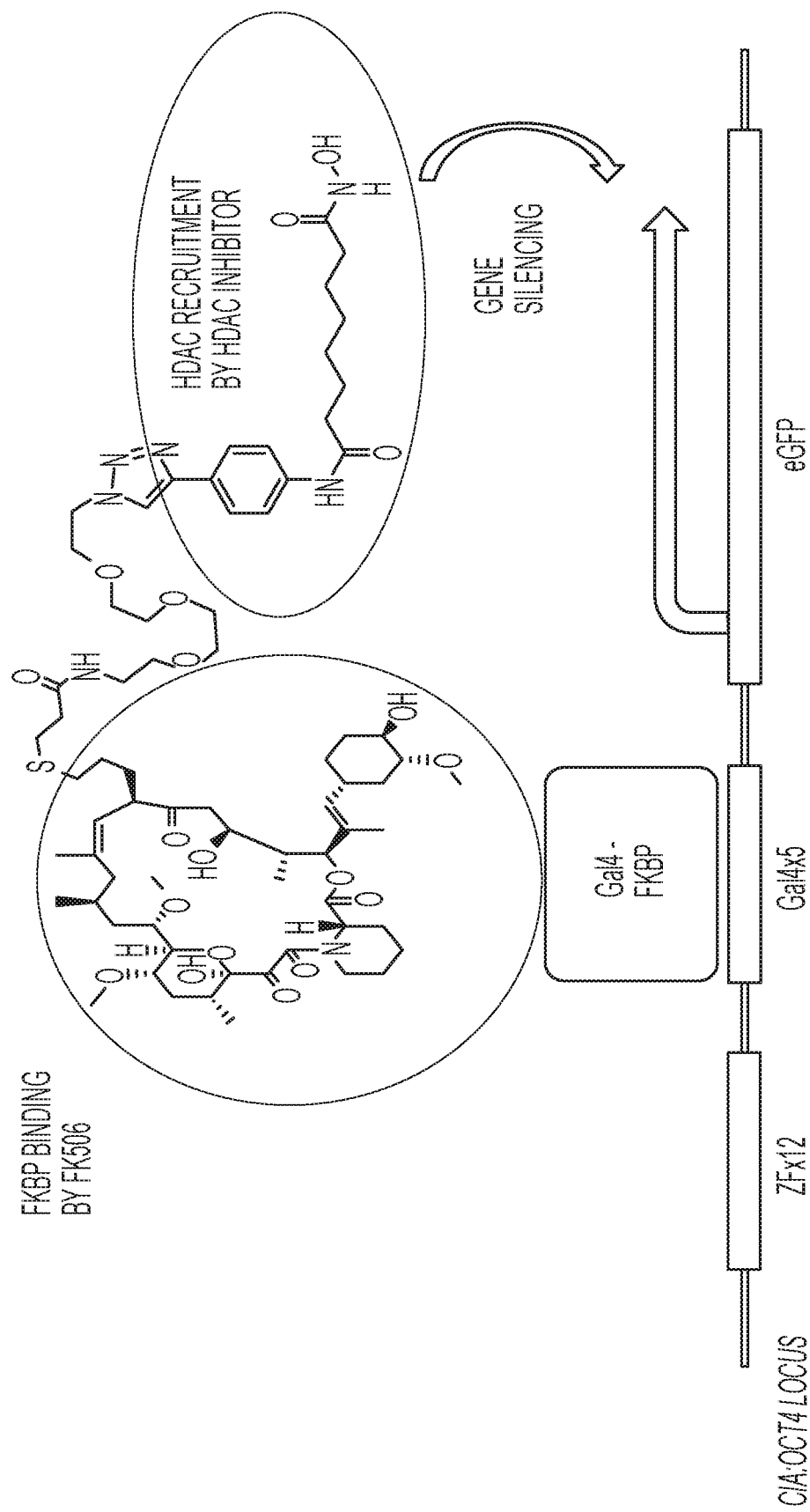

The present disclosure can be understood more readily by reference to the following detailed description of the invention, the figures and the examples included herein.

Before the present compositions and methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

Definitions

As used in the specification and the appended claims, the singular forms "a," "an" and "the" include plural referents unless the context clearly dictates otherwise.

The word "or" as used herein means any one member of a particular list and also includes any combination of members of that list.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

Ranges can be expressed herein as from "about" or "approximately" one particular value, and/or to "about" or "approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

As used herein, the terms "optional" or "optionally" mean that the subsequently described event or circumstance may or may not occur and that the description includes instances where said event or circumstance occurs and instances where it does not.

As used herein, the term "subject" refers to the target of administration, e.g., a human. Thus, the subject of the disclosed methods can be a vertebrate, such as a mammal, a fish, a bird, a reptile, or an amphibian. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In one aspect, a subject is a mammal. In another aspect, the subject is a human. The term does not denote a particular age or sex. Thus, adult, child, adolescent and newborn subjects, as well as fetuses, whether male or female, are intended to be covered.

As used herein, the term "patient" refers to a subject afflicted with a disease or disorder. The term "patient" includes human and veterinary subjects. In some aspects of the disclosed methods, the "patient" has been diagnosed with a need for treatment for cancer, such as, for example, prior to the administering step.

As used herein, the term "treating" refers to partially or completely alleviating, ameliorating, relieving, delaying onset of, inhibiting or slowing progression of, reducing severity of, and/or reducing incidence of one or more symptoms or features of a particular disease, disorder, and/or condition. Treatment can be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition. For example, the disease, disorder, and/or condition can be cancer.

As used herein, the terms "inhibit," "inhibiting," and "inhibition" mean to diminish or decrease an activity, response, condition, disease, or other biological parameter. This can include, but is not limited to, the complete ablation of the activity, response, condition, or disease. This may also include, for example, a 10% inhibition or reduction in the activity, response, condition, or disease as compared to the native or control level. Thus, in an aspect, the inhibition or reduction can be a 10, 20, 30, 40, 50, 60, 70, 80, 90, 100 percent, or any amount of reduction in between as compared to native or control levels. In an aspect, the inhibition or reduction is 10-20, 20-30, 30-40, 40-50, 50-60, 60-70, 70-80, 80-90, or 90-100 percent as compared to native or control levels. In an aspect, the inhibition or reduction is 0-25, 25-50, 50-75, or 75-100 percent as compared to native or control levels. Further, the terms, "inhibit" or "inhibiting" mean decreasing tumor cell growth rate from the rate that would occur without treatment and/or causing tumor mass (e.g., cancer) to decrease. Inhibiting also include causing a complete regression of the tumor (e.g., cancer).

As used herein, "modulate" is meant to mean to alter, by increasing or decreasing. As used herein, "prevent" is meant to mean minimize the chance that a subject who has an increased susceptibility for developing cancer (or an autoimmune disorder or disease) will develop cancer (or an autoimmune disorder or disease).

Compositions

Disclosed herein are bifunctional chemical epigenetic modifiers (CEMs). In an aspect, the bifunctional CEMs can comprise a molecule of FK506 or derivative thereof, a linker and a bifunctional ligand. In an aspect, the bifunctional CEM can comprise CEM23 or CEM46. In an aspect, the bifunctional CEM can be a CEM-activator (CEMa) or a CEM-repressor (CEMr). In an aspect, the bifunctional CEM or CEMa can comprise CEM87, CEM88 or CEM114.

FK506 (also known as tacrolimus or fujimycin, and by trade names Prograft, Advagraf, and Protopic) binds to an FK506-binding protein, FKBP, with a high affinity, forming an FK506-FKBP complex.

FKBPs (FK506 binding proteins) are the cytosolic receptors for macrolides such as FK506, FK520 and rapamycin and are conserved across species lines. For the purpose of this disclosure, FKBPs are proteins or protein domains which are capable of binding to a bifunctional CEM and further forming a complex (e.g., bifunctional ligand-FK506-Gal4-FKBP, bifunctional ligand-FK506-p300). In some aspects, the FK506 derivative can be a dimeric form of FK506, including, but not limited to FK1012.

In an aspect, the bifunctional CEMs can include a linker. The linker can couple the FK506 or derivative thereof to the bifunctional ligand. A given linker within the present compositions can provide a cleavable linkage (e.g., a thioester linkage) or a non-cleavable linkage (e.g., a maleimide linkage). The linker can be selected from the group consisting of monofluoro cyclooctyne (MFCO), bicyclo[6.1.0]nonyne (BCN), N-succinimidyl-Sacetylthioacetate (SATA), N-succinimidyl-S-acetylthiopropionate (SATP), maleimido and dibenzocyclooctyne ester (a DBCO ester). Useful cyclooctynes, within a given linker, include OCT, ALO, MOFO, DIFO, DIBO, BARAC, DIBAC, and DIMAC.

In an aspect, the linker can be a homofunctional linker or a heterofunctional linker. The linker can be a covalent bond. The homofunctional linker can be a homobifunctional, homotrifunctional, or homotetrafunctional linker comprising two, three, or four reactive groups, respectively, that react with a primary amine, a thiol group, a hydroxyl group, or a carbohydrate. The heterofunctional linker can be a heterobifunctional, heterotrifunctional, or heterotetrafunctional linker comprising at least one reactive group that reacts with a primary amine, a thiol group, a hydroxyl group, or a carbohydrate. In an aspect the linker can be a heterobifunctional, heterotrifunctional, or heterotetrafunctional linker comprising a group reactive with a primary amine and a group reactive with a thiol group. Among the commercially available homobifunctional cross-linkers are: BSOCOES (Bis(2-[Succinimidooxycarbonyloxy]ethyl) sulfone; DPDPB (1,4-Di-(3'42pyridyldithiol-propionamido) butane; DSS (disuccinimidyl suberate); DST (disuccinimidyl tartrate); Sulfo DST (sulfodisuccinimidyl tartrate); DSP (dithiobis(succinimidyl propionate); DTSSP (3,3'-Dithiobis (sulfosuccinimidyl propionate); EGS (ethylene glycol bis (succinimidyl succinate)); and BASED (Bis($\beta$[4-azidosalicylamido]-ethyl)disulfide iodinatable).

Examples of linkers include pyridinedisulfide, thiosulfonate, vinylsulfonate, isocyanate, imidoester, diazine, hydrazine, thiol, carboxylic acid, multi-peptide linkers, and acetylene. Alternatively, other linkers than can be used include BS3 [Bis(sulfosuccinimidyl)-suberate], NHS/EDC (N-hydroxysuccinimide and 1-ethyl-3-(3-dimethylaminopropyl)-carbodiimide, sulfo-EMCS ([N-$\epsilon$-maleimidocaproic acid]hydrazide, hydrazide. Another useful linker is SATA (N-succinimidyl-Sacetylthioacetate).

In some aspects, the linker can be a cleavable linker. Cleavable linkers are known in the art, and conventional chemistry can be applied to attach a linker to a molecule of FK506 or derivative thereof, and a bifunctional ligand. The linker can be cleaved by any suitable method, including exposure to acids, bases, nucleophiles, electrophiles, radicals, metals, reducing or oxidising agents, light, temperature, enzymes etc. Suitable linkers can be adapted from standard chemical blocking groups, as disclosed in Greene & Wuts, *Protective Groups in Organic Synthesis*, John Wiley & Sons. Further suitable cleavable linkers used in solid-phase synthesis are disclosed in Guillier et al. (*Chem. Rev.* 100:2092-2157, 2000).

The use of the term "cleavable linker" is not meant to imply that the whole linker is required to be removed from the FK506 or derivative thereof or the bifunctional ligand. The cleavage site can be located at a position on the linker that ensures that part of the linker remains attached to the FK506 or derivative thereof or the bifunctional ligand after cleavage. Suitable linkers include, hut are not limited to, disulfide linkers, acid labile linkers (including dialkoxybenzyl linkers, Sieber linkers, indole linkers, t-butyl Sieber linkers, electrophilically cleavable linkers, nucleophilically cleavable linkers, photocleavable linkers, cleavage under reductive conditions, oxidative conditions, cleavage via use of safety-catch linkers, and cleavage by elimination mechanisms.

Electrophilically cleaved linkers are typically cleaved by protons and include cleavages sensitive to acids. Suitable linkers include the modified benzylic systems such as trityl, p-alkoxybenzyl esters and p-alkoxybenzyl amides. Other suitable linkers include ten-butyloxycarbonyl (Boc) groups and the acetal system. The use of thiophilic metals, such as nickel, silver or mercury, in the cleavage of thioacetal or other sulphur-containing protecting groups can also be considered for the preparation of suitable linker molecules.

Nucleophilic cleavage is also a well-recognized method in the preparation of linker molecules. Groups such as esters that are labile in water (i.e., can be cleaved simply at basic pH) and groups that are labile to non-aqueous nucleophiles, can be used. Fluoride ions can be used to cleave silicon-oxygen bonds in groups such as triisopropyl silane (TIPS) or t-butyldimethyl silane (TBDMS).

Photocleavable linkers have been used widely in carbohydrate chemistry. It is preferable that the light required to activate cleavage does not affect the other components of the modified nucleotides. For example, if a fluorophore is used as the label, it is preferable if this absorbs light of a different wavelength to that required to cleave the linker molecule. Suitable linkers include those based on O-nitrobenyl compounds and nitroveratryl compounds, Linkers based on benzoin chemistry can also be used (Lee et al., *J. Org. Chem.* 64:3454-3460, 1999).

There are many linkers known that are susceptible to reductive cleavage. Catalytic hydrogenation using palladium-based catalysts has been used to cleave benzyl and benzyloxycarbonyl groups, Disulphide bond reduction is also known in the art.

Oxidation-based approaches are well known in the art. These include oxidation of p-alkoxybenzyl groups and the oxidation of sulphur and selenium linkers. The use of aqueous iodine to cleave disulphides and other sulphur or selenium-based linkers is also within the scope of the invention.

Safety-catch linkers are those that cleave in two steps. In a preferred system the first step is the generation of a reactive nucleophilic center followed by a second step involving an intra-molecular cyclization that results in cleavage. For example, levulinic ester linkages can be treated with hydrazine or photochemistry to release an active amine, which can then be cyclised to cleave an ester elsewhere in the molecule (Burgess et al., *J. Org. Chem,* 62:5165-5168, 1997).

Elimination reactions can also be used. For example, the base-catalysed elimination of groups such as Fmoc and cyanoethyl, and palladium-catalysed reductive elimination of allylic systems, can be used.

As well as the cleavage site, in some aspects the linker can comprise a spacer unit. The spacer distances the FK506 or derivative thereof or the bifunctional ligand from the cleavage site. Examples of protospacer sequences are in Table 4.

In an aspect, the linker can comprise a disulfide, acid labile Sieber, indole, t-butyl Sieber, electrophilically cleavable, or nucleophilicially cleavable moiety.

To form covalent bonds, one can use as a chemically reactive group a wide variety of active carboxyl groups (e.g., esters) where the hydroxyl moiety is physiologically acceptable at the levels required to modify the peptide. Particular agents include N-hydroxysuccinimide (NHS), N-hydroxysulfosuccinimide (sulfo-NHS), maleimide-benzoyl-succinimide (MBS), gamma-maleimido-butyryloxy succinimide ester (GMBS), maleimido propionic acid (MPA), maleimido hexanoic acid (MHA), and maleimido undecanoic acid (MUA).

Examples of amine-to-carboxyl linkers include carbodiimide compounds (e.g., DCC (N,Ndicyclohexylcarbodimide) and EDC (1-ethyl-3-[3-dimethylaminopropyl]carbodiimide)). Examples of sulfhydryl-to-nonselective linkers include pyridyldithiol/aryl azide compounds (e.g., APDP ((iV-[4-(/;-azidosalicylamido)butyl]-3-(2-pyridyldithio)propionamide)). Examples of sulfhydryl-to-carbohydrate linkers include maleimide/hydrazide compounds (e.g., BMPH (A-[β-maleimidopropionic acidjhydrazide), EMCH ([A-ε-malcimidocaproic acidjhydrazide), MPBH 4-(4-A-maleimidophenyl)butyric acid hydrazide), and KMUH (A-[κ-maleimidoundecanoic acidjhydrazide)) and pyridyldithiol/hydrazide compounds (e.g., PDPH (3-(2-pyridyldithio) propionyl hydrazide)). Exemplary carbohydrate-to-nonselective linkers include hydrazide/aryl azide compounds (e.g., ABH (p-azidobenzoyl hydrazide)). Examples of hydroxyl-to-sulfhydryl linkers include isocyanate/maleimide compounds (e.g., (N-[pmaleimidophenyljisocyanate)). Examples of amine-to-DNA linkers include NHS ester/psoralen compounds (e.g., SPB (succinimidyl-[4-(psoralen-8-yloxy)]-butyrate)).

In an aspect, the linker can be a chemical conjugate. In an aspect, the chemical conjugate can be polyethylene glycol (PEG). In an aspect, the number of PEG units can be 1, 2, 3, 4, 5, 6, 7, 8, 9, 10, 11, 12, 13, 14, 15, 16, 17, 18, 19, 20 or more. In an aspect, the number of PEG units can be of sufficient length to separate the FK506 or derivative thereof from the bifunctional ligand to prevent any steric interference between the FK506 or derivative thereof and the bifunctional ligand. In an aspect, the linker can include 3 PEG units. In an aspect, the linker can include a propyl linker.

Conjugation techniques can include the application of click chemistry. Generally, click chemistry is a modular reaction that is widely applicable and capable of producing high yields of products under physiological conditions. Click chemistry encompasses four classes of chemical transformations. The first are non-aldol type carbonyl chemical reactions, such as those that form ureas, thioureas, oxime ethers, hydrazone, amides, and aromatic heterocycles. The second transformations are nucleophilic substitution reactions in which a ring within a strained heterocyclic electrophile (e.g., epoxides, aziridines and aziridinium ions) is opened. In the third, addition reactions to C—C multiples bonds, such as Michael addition, epoxidation, aziridation, and dihydroxylation occurs, and in the fourth, are cycloaddition reactions, such as 1,3-dipolar cycloaddition and Diels-Alder reactions. 1,3-dipolar cycloaddition (1,3-Huisgen reaction) of an alkyne and an azide to form five membered triazole is a particular example of a click reaction.

In an aspect, the bifunctional ligand can be an activator or an inhibitor. Examples of inhibitors include but are not limited to bromodomain inhibitors, heterochromatin protein 1 (CBX) domain inhibitors, methyl-CpG-binding domain (MBD) inhibitors, and DNA methylation inhibitors. In an aspect, the bifunctional ligand can be an epigenetic inhibitor. In an aspect, the epigenetic inhibitor can be a histone deacetylase (HDAC) inhibitor. Examples of HDAC inhibitors include but are not limited to vorinostat (e.g., suberanilohydroxamic acid (SAHA), depsipeptide (e.g., romidepsin, FK228), and derivatives thereof.

Targeted Gene Repression Using Bifunctional Ligands

Epigenome editing is a method used in life science research that can be used to develop new therapies for diseases initiated or maintained by epigenetic dysregulation, including several types of cancers and autoimmune disorders. In addition, much is still unknown about the mechanisms by which, for example, histone-modifying proteins work in concert to properly regulate gene expression. Complex epigenetic interactions in live cells were investigated and manipulated. Described herein is a small-molecule platform for inducing gene repression and histone deacetylation at a reporter gene. Also, described herein are bifunctional chemical epigenetic modifiers (CEMs) that can be synthesized to comprise at least two functional groups: FK506 or a derivative thereof, capable of binding to a Gal4-FKBP fusion transcription factor, and, for example, a histone deacetylase (HDAC) inhibitor that recruits HDAC-containing corepressor complexes. Further disclosed herein are reporter cell lines, which contains a GFP reporter allele upstream of a Gal4 DNA binding array in the murine Oct4 locus, showing that a lead CEM repressed GFP expression by 50%. The results also described herein show that CEM recruitment of deacetylation activity causes marked deacetylation along a target loci. This system allowed the detailing of the direct results of HDAC recruitment to chromatin to be evaluated and to measure the resulting gene expression in a chemically-dependent and reversible manner. The CEMs system disclosed herein provides new insights into epigenetic gene regulation and provides proof-of-concept for a new therapeutic strategy to control gene regulation in human disease. The bifunctional CEMs disclosed herein can be derived from FDA-approved epigenetic modulator drugs avoiding the toxicities and off-target effects caused by whole-cell application of these drugs.

Using a purely genetic editing technology as a therapeutic or an in vivo tool is off target or continuous recruitment, which can cause permanent genetic mutation at undesirable loci (Lanphier, E., Urnov, F., Haecker, S. E., Werner, M. & Smolenski, *J. Nature* 519, 410-411 (2015)). As an alternative, a small molecule platform for epigenome editing is described herein. Small molecules have some advantages over genetic methods as a therapeutic and a research tool: treating cells with small molecules is technically easy and requires little optimization, they are typically easy to synthesize, they can be active in vivo, effects are often dose sensitive, and most importantly, effects are reversible. Disadvantages also exist for small molecules: their functions are typically more difficult to engineer, their cellular effects may be less profound, and they may have more off-target effects than genetic methods.

Using bivalent small molecules to direct proteins to DNA has been investigated (Hojfeldt, J. W., Van Dyke, A. R. & Mapp, *Chem. Soc. Rev.* 40, 4286-94 (2011)). "Small molecule transcription factors" featuring hairpin polyamide DNA binding motifs linked to histone deacetylase inhibitors were used to activate transcription of DNA (Xiao, X., Yu, P., Lim, H.-S., Sikder, D. & Kodadek, *Angew. Chemie* Int. Ed. 46, 2865-2868 (2007)). Because polyamides are difficult to synthesize and the effects likely result from a combination of on-target and off-target effects, this approach is not ideal. Similar examples have been reported that use polyamides or transcription factor ligands as the DNA binding ligand and coactivator-binding molecules as a transcriptional activation domain (Hojfeldt, J. W., Van Dyke, A. R. & Mapp, *Chem. Soc. Rev.* 40, 4286-94 (2011)). In another example, glucocorticoid receptor (GR) ligands tethered to FK506 were used to recruit a histone deacetylase (HDAC) 1-FKBP fusion protein to DNA, causing down-regulation of GR-controlled genes (Hojfeldt, J. W. et al. *Mol. Endocrinol.* 28, 249-59 (2014)). Recently, Liszczak et al. used native chemical ligation to attach small molecules to dCas9, allowing CRISPR guided targeting of the molecules to DNA (Liszczak, G. P. et al. *PNAS* 114, 681-686 (2017)). This system did not cause any changes in gene expression unless the cells were co-transfected with a VP64-Brd4 fusion protein. Thus far, none of these methods have been shown to specifically change both the epigenetic state and the expression of a target gene.

Controlling chemically induced proximity between corepressor complexes and DNA-bound transcription factors requires a bivalent ligand capable of strong interactions with both the transcription factor and a corepressor complex. Components of corepressor complexes with high-affinity ligands include the histone deacetylase (HDAC) enzymes and EZH2 (Kim, W. et al. *Nat. Chem. Biol.* 9, 643-650 (2013); (Dokmanovic, M., Clarke, C. & Marks, P. A. *Mol. Cancer Res.* 5, 981-989 (2007)). HDAC inhibitors can be selected as the bifunctional ligands because they are potent, easy to synthesize, and tolerate the attachment of long linker groups while still being cell-permeable (Becher, I. et al. *ACS Chem. Biol.* 9, 1736-1746 (2014)). Also, the isoform selectivity and residence time can be tuned by modifying the ligand (Wagner, F. F. et al. *Chem. Sci.* 6, 804-815 (2015); Kalin, J. H. & Bergman, J. A. *Journal of Medicinal Chemistry* 56, 6297-6313 (2013)). HDAC enzymes reverse the histone acetyl marks associated with open chromatin and active transcription (Zhang, H., Gao, L., Anandhakumar, J. & Gross, *PLoS Genet.* 10, (2014); (Delcuve, G. P., Khan, D. H. & Davie, J. R. *Clin. Epigenetics* 4, 5 (2012)). It may seem counterintuitive to use enzyme inhibitors to recruit a complex that enzymatically modifies histones, but HDACs exist in complexes that contain proteins capable of silencing genes through many different mechanisms, and some HDACs are catalytically inactive psuedoenzymes that still bind inhibitors (Lahm, A. et al. *Proc. Natl. Acad. Sci. U.S.A.* 104, 17335-40 (2007); (Harris, L. G. et al. *Nucleic Acids Res.* 44, 3610-3617 (2016)). Furthermore, HDAC enzymes can exist in complexes with other HDAC isoforms that would not be inhibited by the small molecule (Kelly, R. D. W. & Cowley, S. M. *Biochem. Soc. Trans.* 41, 741-9 (2013)). HDAC inhibitors bind to corepressor complexes such as CoREST, NuRD, and Sin3 with certain selectivity profiles, depending on the chemical structure and HDAC isoform bound (Becher, I. et al., *ACS Chem. Biol.* 9, 1736-1746 (2014); (Bantscheff, M. et al. *Nat. Biotechnol.* 29, 255-65 (2011)). By tuning the inhibitor structure, it may be possible to recruit specific corepressor complexes to the target gene.

Additionally, these bifunctional molecules or ligands described herein can be derived from FDA-approved HDAC inhibitors that have been well studied and characterized. Suberanilohydroxamic acid (SAHA) and several other epigenetic inhibitors are widely used in the clinic (Marks, P. Oncogene 26, 1351-1356 (2007); (Zwergel, C., Stazi, G., Valente, S. & Mai, A. J. Clin. Epigenetics 2, 1-15 (2016)). Though these drugs are effective modulators of certain cellular pathways, their cell-wide effects cause high toxicity and modulate the expression of many genes (Peart, M. J. et al. Proc. Natl. Acad. Sci. U.S.A. 102, 3697-3702 (2005)). Described herein are targeted, gene-specific application of these ligands. This technology disclosed herein can control gene expression in a dose sensitive and reversible manner, allowing control over gene expression through modulation of acetylation levels at the target gene promoter.

Drugs that target the addition, removal, or recognition of histone modifications, such as HDAC inhibitors, do this across the genome. The HDAC inhibitors suberanilohydroxamic acid and depsipeptide have been shown to change the expression of up to 22% of genes (Peart, M. J. et al. Proc. Natl. Acad. Sci. U.S.A. 102, 3697-3702 (2005)). HDAC inhibitors also modulate acetylation of many non-histone proteins (Seto, E. & Yoshida, M. Cold Spring Harb. Perspect. Biol. 6, (2014)). This lack of selectivity causes side effects, and thus, most of these drugs are reserved for use in cancers for which there aren't many other therapeutic options (Subramanian, S., Bates, S. E., Wright, J. J., Espinoza-Delgado, I. & Piekarz, R. L. Pharmaceuticals 3, 2751-2767 (2010)). By tethering epigenetic modulator drugs to a DNA-targeting group, the pharmacology of these drugs is constrained to the target locus, providing a robust effect at the target gene with minimal off-target effects.

The success of the studies described herein, and other results (Hojfeldt, J. W. et al. Mol. Endocrinot 28, 249-59 (2014)) shows that small molecule epigenome editing is possible. As described herein, an HDAC inhibitor can be tethered to, for example, a glucocorticoid or androgen receptor (AR) ligand, and be used to repress genes bound by these receptors. An AR receptor ligand—HDAC inhibitor conjugate could be a therapy for androgen-independent prostate cancer, where the AR inappropriately activates target genes with changes to the epigenome (Wang, Q. et al. Cell 138, 245-256 (2009)). Because of the difficulties in delivering proteins or genes in vivo, bivalent small molecules may be a simple way to achieve targeted in vivo epigenome editing.

Targeted Gene Activation Using Bifunctional Ligands

The emerging field of epigenetic bioengineering has been fueled by advances in protein engineering and chemistry. Described herein are methods and compositions comprising deactivated Cas9 (dCas9) to achieve allele specific targeting combined with bifunctional small molecules capable of capturing endogenous chromatin activating machinery and tethering it to specific genetic loci. The result is increased transcriptional activity wherein gene expression can be intricately governed by small molecule dosage. This approach provides advances over current epigenetic editing technologies. For example, the payload needed to package in viral vectors can be reduced since the protein tag used to recruit the small molecule is an order of magnitude smaller than the large acetyltransferases usually coupled to dCas9. Additionally or alternatively, since the small molecule itself is capturing the epigenetic machinery there are no exogenous transcriptional activators and physiologically proteins are used. The compositions and methods disclosed herein are adaptable for discovery research and has therapeutic application for diseases driven by gene mis-regulation.

The eukaryotic genome is organized and packaged into chromatin with varying degrees of compaction, which contributes to the regulation of gene expression. A complex network of protein-protein and DNA-protein interactions ensures the proper levels of gene expression, disruptions to this regulatory network drives many human diseases including cancer (Dawson, M. A., Science. 355, 1147-1152 (2017); MacDonald, I. A. & Hathaway, N. A., Immunol. Cell Biol. 93, 261-70 (2015)). An important contributing factor that sculpts the chromatin landscape is post-translational histone tail modifications. Lysine acetylation is one such modification that has both biophysical and indirect protein-recruitment effects. Protein families of writers (histone acetyl transferases, HATs), erasers (histone deacetylases, HDACs), and reader proteins control the deposition, removal, and down-stream gene expression changes associated with this mark (Zeng, L. & Zhou, M. M. FEBS Lett 513, 124-8 (2002); (de Ruijter, A. J. M. et al. Biochem. 1 370, 737-49 (2003)). The power of recruiting exogenous chromatin modifying machinery as a way to control expression levels in a gene-specific manner has been previously (Gao, Y. et al. Nat. Methods 13, 1043-1049 (2016); (Chen, T. et al. J. Am. Chem. Soc. 139, 11337-11340 (2017); (Braun, S. M. G. et al. Nat. Commun. 8, (2017); (Ma, D. et al. Nat. Commun. 7, 13056 (2016); (Shrimp, J. H. et al. ACS Chem. Biol. 13, 455-460 (2018); (Hilton, I. B. et al. Nat. Biotechnol. 33, 510-517 (2015)). With major advances in the Cas9 (CRISPR associated protein 9) and dCas9 (deactivated Cas9) technology, the ability to precisely induce changes in expression has rapidly evolved. As described herein, in an aspect the compositions and methods can be used to redirect endogenous chromatin modifying machinery in a dose-dependent and chemically-dependent manner.

Targeted Gene Repression or Activation Using Dcas9-Chemical Epigenetic Modifiers Described herein are compositions and methods involving molecular protein design of dCas9 systems, chemical-mediated epigenetic manipulation, and oncology therapeutics. Further described herein are changes to dCas9 gene regulation technology using novel chemical based approaches that can be applied toward the development of a prostate cancer therapeutic test platform. As described herein, this technology can be applied toward the treatment of a diverse assortment of cancers and other human diseases. The application of this platform can have the ability to control individual gene programs with precision, based on a patient's genetic and epigenetic profile.

A bacterial defense against bacteriophages, termed Clustered Regularly Interspaced Short Palindromic Repeats (CRISPR) and CRISPR-associated protein-9 nuclease (Cas9) has revolutionized basic and translational research. This system uses short guide RNAs (sgRNA or gRNA) to target Cas9 nuclease to cleave out invading phage DNA elements from the bacterial genome. Recently, it was adapted to function in mammalian systems to target and cut any desired DNA sequence. These cuts introduce areas sensitive to homologous recombination whereby DNA bases can be added, deleted, or modified. Almost any genomic sequence can undergo targeted editing using technical adaptations to the CRISPR-Cas9 system, allowing for manipulation of the mammalian genome (Hsu, P. D., Lander, E. S. & Zhang, F. Cell 157, 1262-1278 (2014)). This has transformed genetic research and inspired new gene therapy approaches for a wide array of human diseases (e.g., muscular dystrophy to cancer) and dozens of genes have been targeted using this approach with some approaching clinical trials (Ousterout, D. G. et al. Nat. Commun. 6, 6244 (2015); (Komor, A. C., Badran, A. H. & Liu, D. R. Cell 168, 20-36 (2017); (Gori, J. L. et al., Hum. Gene Ther. 26, 443-451 (2015)).

Most CRISPR-Cas9 therapeutics currently in development utilize the active nuclease component of Cas9 to edit genomic DNA to fix genetic defects. One advantage of this approach is that these are permanent solutions to address previously untreatable diseases. A key downside is that off-target effects of Cas9-based gene editing are permanent, which is a concerning reality with clinical and regulatory implications (Lanphier, E., Urnov, F. D., Ehlen, S. H., Werner, M. & Smolenski, J. Nature 519, 410-411 (2015)). Described herein are compositions and epigenetic methods to control gene expression without altering the genomic DNA sequence. These methods use a catalytically inactive Cas9 (dCas9), where the nuclease activity has been mutated so that the dCas9 binds to, but does not cleave, target DNA. Then, chemical techniques to recruit chromatin modifying enzymes to the dCas9, will be used. Enzyme recruitment to the target gene will result in marked gene repression. Also described herein is the development of the molecular targeting method, and the application the said methods in model systems of metastatic prostate cancer (mPC).

Metastatic prostate cancer (mPC) will serve as a model disease to test the compositions and methods described herein for several reasons. First, PC is a common solid malignancy. In the U.S., PC is the most commonly diagnosed malignancy, and is the second leading cause of cancer-related death among men. It is estimated that in 2017, 161,360 new cases will be diagnosed and 26,730 deaths caused by PC will occur (Siegel, R. L., Miller, K. D. & Jemal, A. CA. Cancer J. Clin. 67, 7-30 (2017)). Second, preclinical and clinical data have elucidated that both mPC and castrate-resistant mPC (mCRPC) remain highly dependent on the androgen receptor (AR) signaling axis (Nelson, P. S. J. Clin. Oncol. 30, 644-646 (2012); (Knudsen, K. E. & Penning, T. M. Trends Endocrinol. Metab. 21, 315-324 (2010)). Third, mPC is currently incurable, and thus there is an unmet need to develop better therapeutics. For over seven decades, androgen deprivation therapy (ADT) has been the cornerstone treatment for mPC; however, reactivated AR signaling drives mPC/mCRPC, making the effects of ADT temporary (~18-30 months) (Oudard, S. Cancer Treat. Rev. 39, 275-289 (2013)). Although newer drugs that target the AR signaling axis (e.g., abiraterone and enzalutamide) represent a major conceptual and clinical advancement in mPC treatment, ⅓ of patients present with primary resistance (i.e., no PSA response), and almost all of the remaining patients will develop secondary resistance to the drugs (Scher, H. I. et al. Lancet (London, England) 375, 1437-1446 (2010); (Scher, H. I. et al. N Engl. J. Med. 367, 1187-1197 (2012); (Antonarakis, E. S. et al. N. Engl. J. Med. 371, 1028-1038 (2014); (Ryan, C. J. et al. N Engl. J. Med. 368, 138-148 (2013); (de Bono, J. S. et al. N Engl. J. Med. 364, 1995-2005 (2011)). Fourth, there are well-defined in vitro and in vivo model systems that exist, which adequately mimic mPC/mCRPC.

Figure 9A:
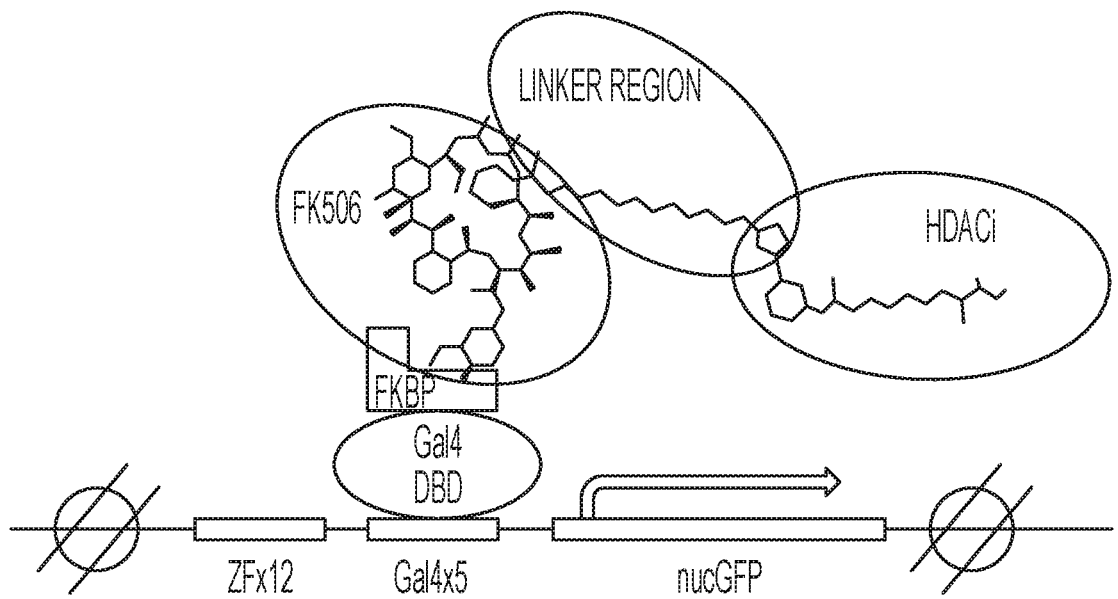
FIGS. 9A-B shows a gene regulation model with dCas9 and CEMs.
Figure 10A:
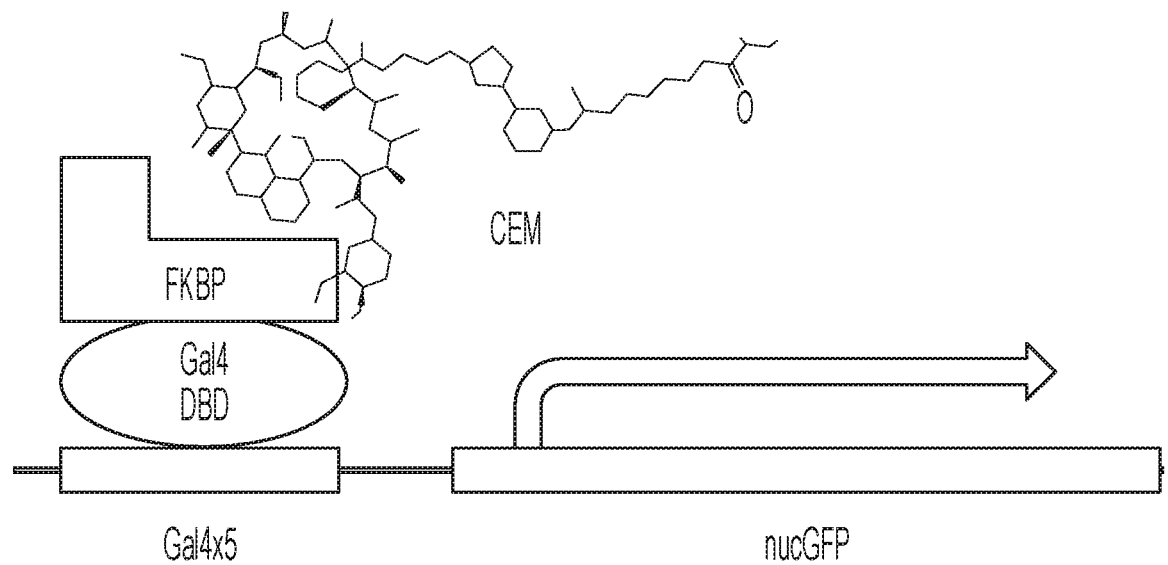
FIGS. 10A-D shows the experimental validation of the CEM approach.
Figure 10B:
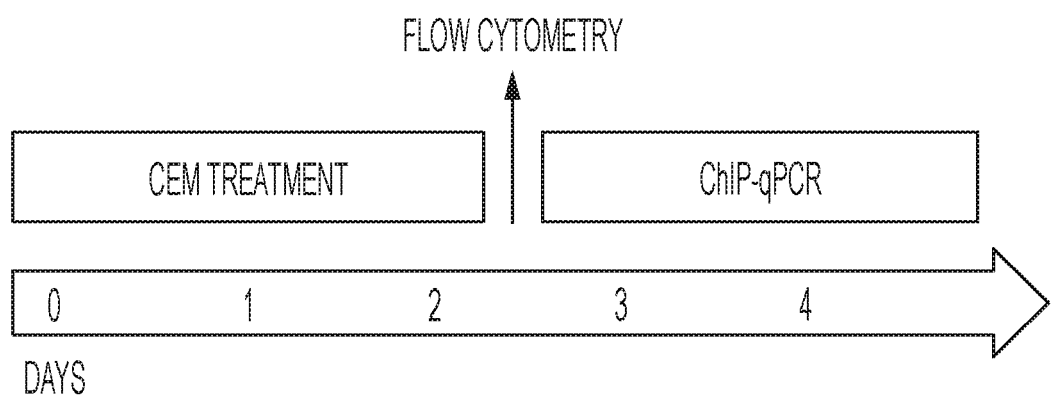
Figure 10C:
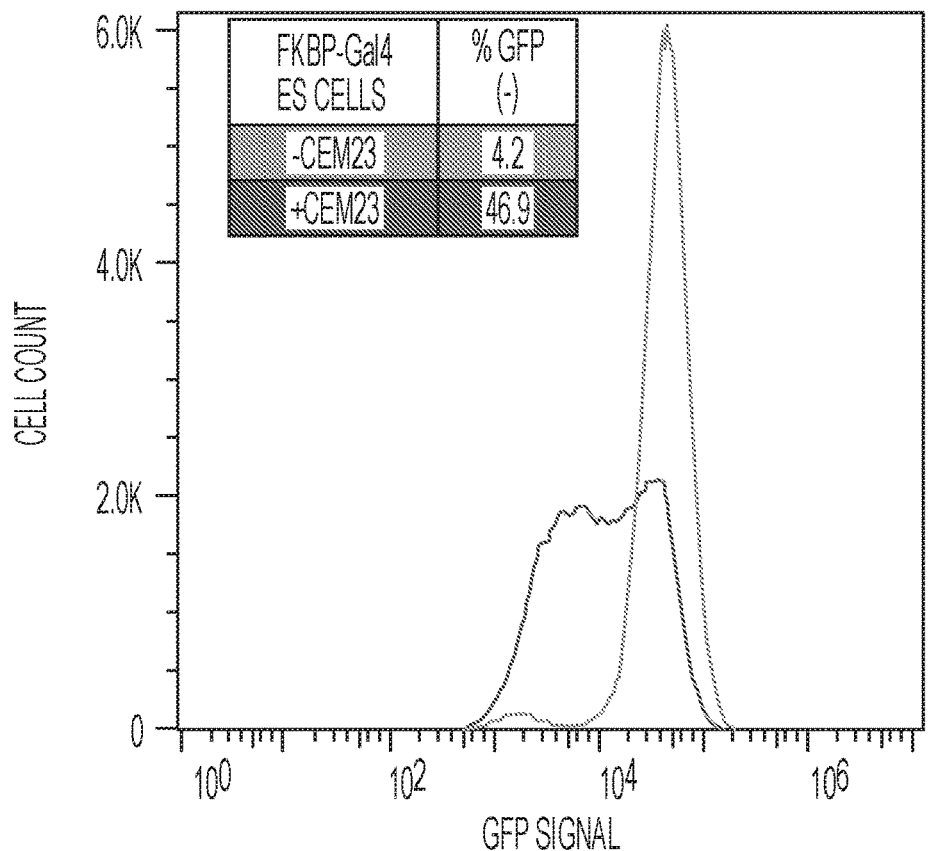
Figure 10D:
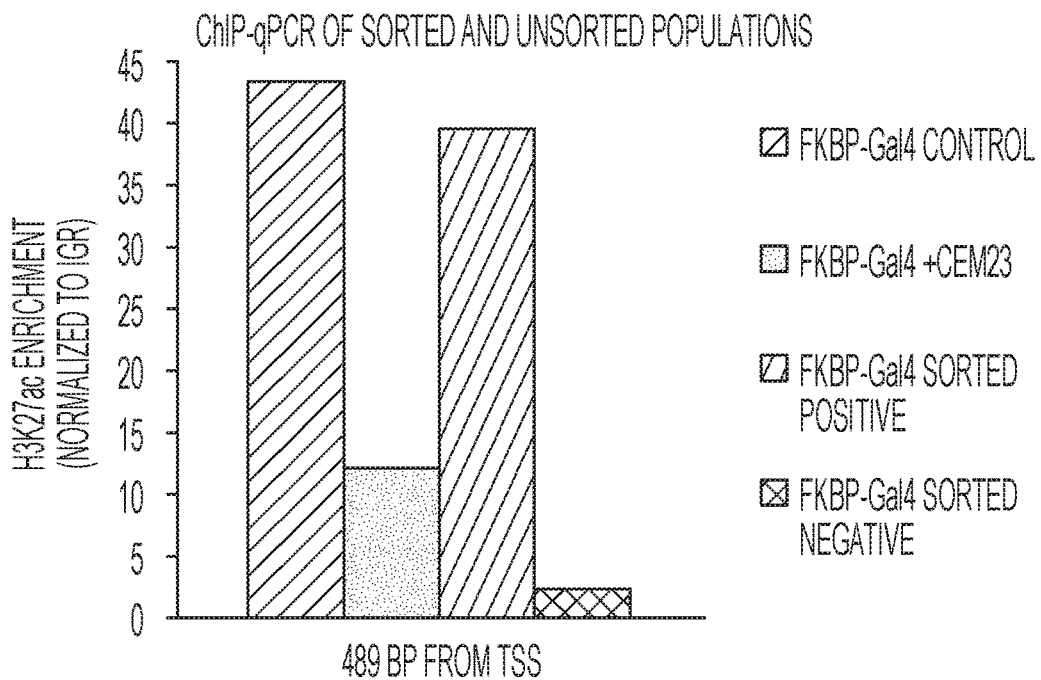
Figure 28:
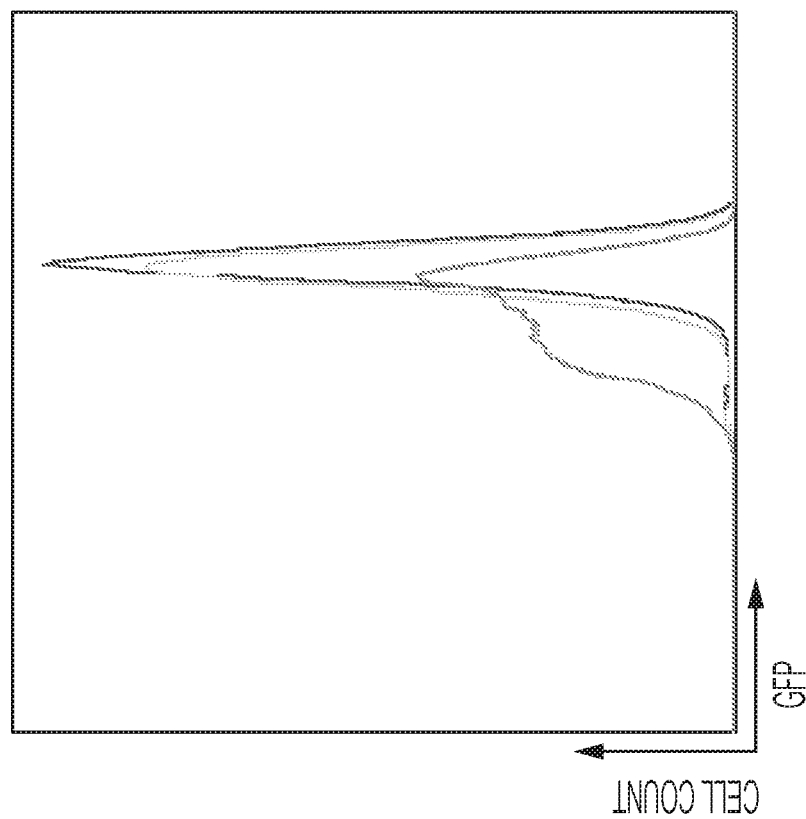
FIG. 28 shows that excess FK506 is able to outcompete CEM23 for the FKBP binding site.
Figure 29:
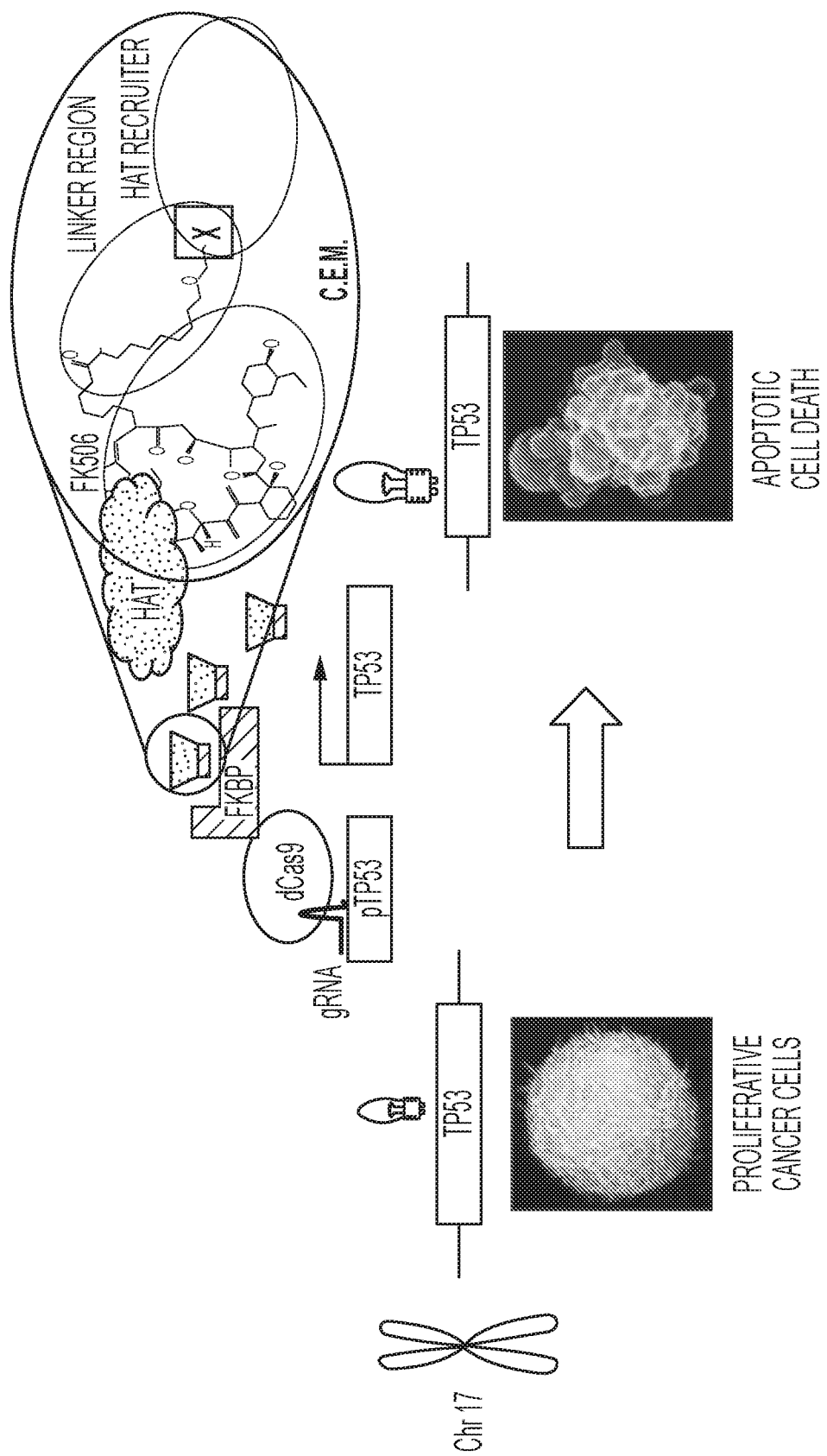
FIG. 29 shows that CEMs target and activate endogenous p53 in colon cancer cells which leads to apoptosis of the targeted cancer cells.
Figure 30A:
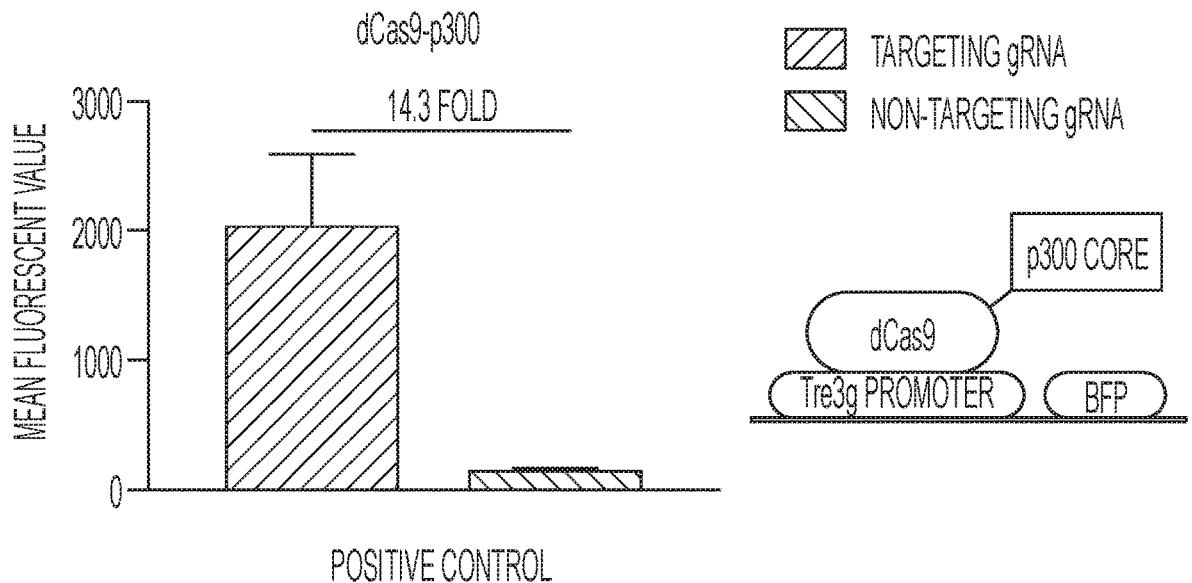
FIGS. 30A-F show protein engineering and synthetic chemistry used to improve the dCas9-CEMa system. HEK 293T cells were transfected with a reporter plasmid that carried a BFP gene (driven by a Tre3G promoter that has low expression) along with a sgRNA targeting the Tre3G promoter and the dCas9.
Figure 30B:
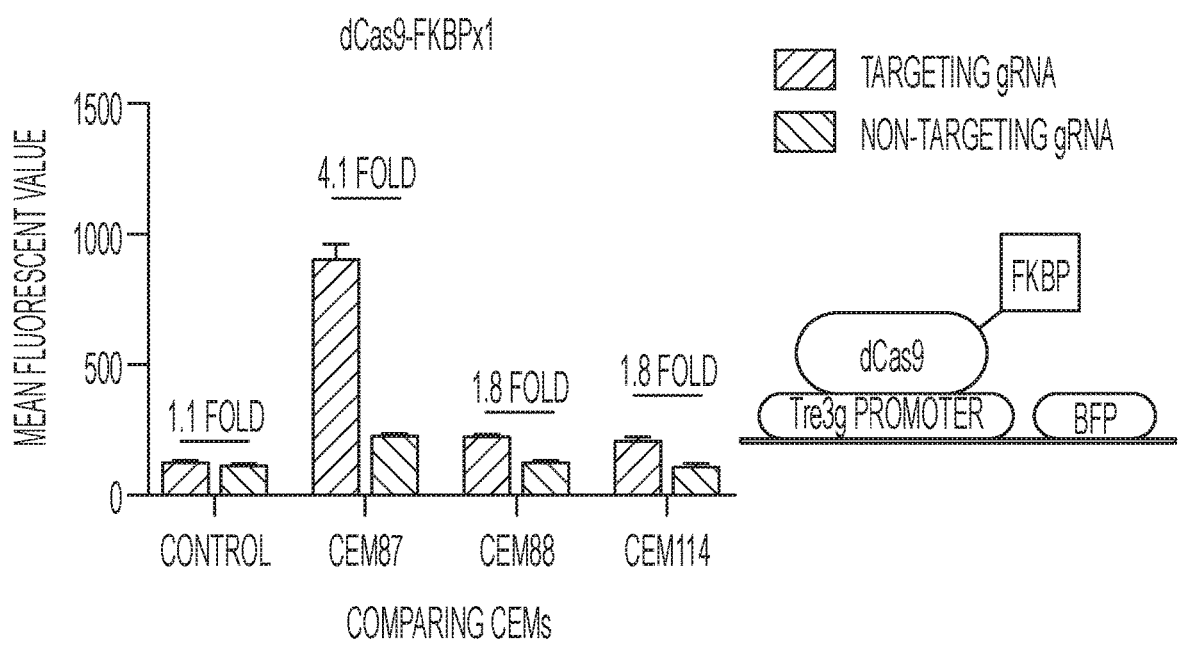
Figure 30C:
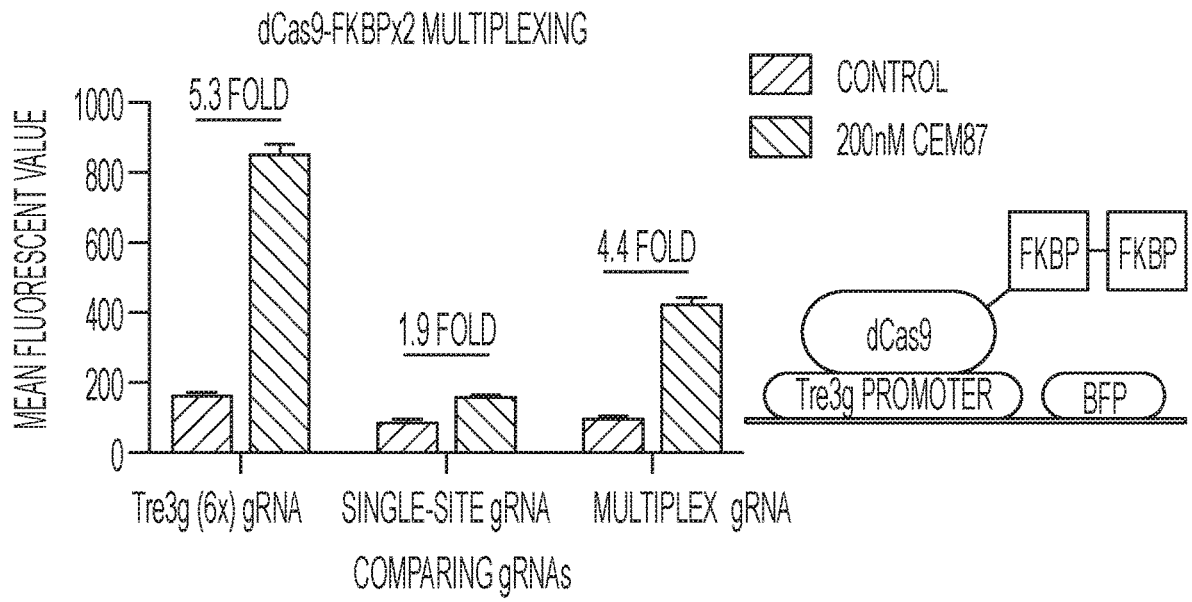
Figure 30D:
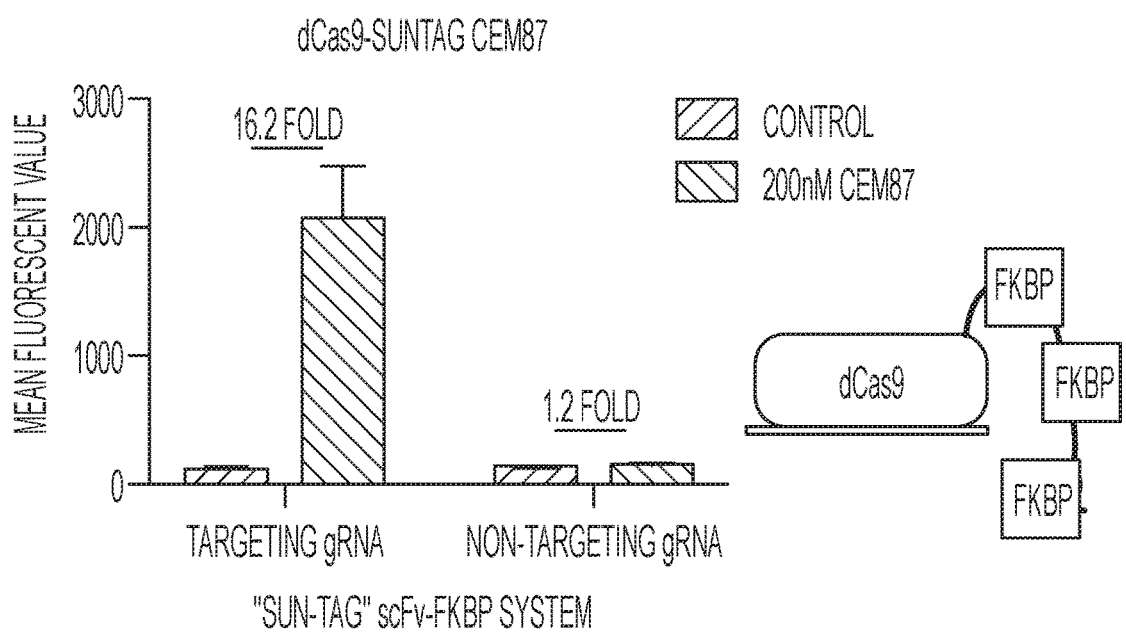
Figure 30E:
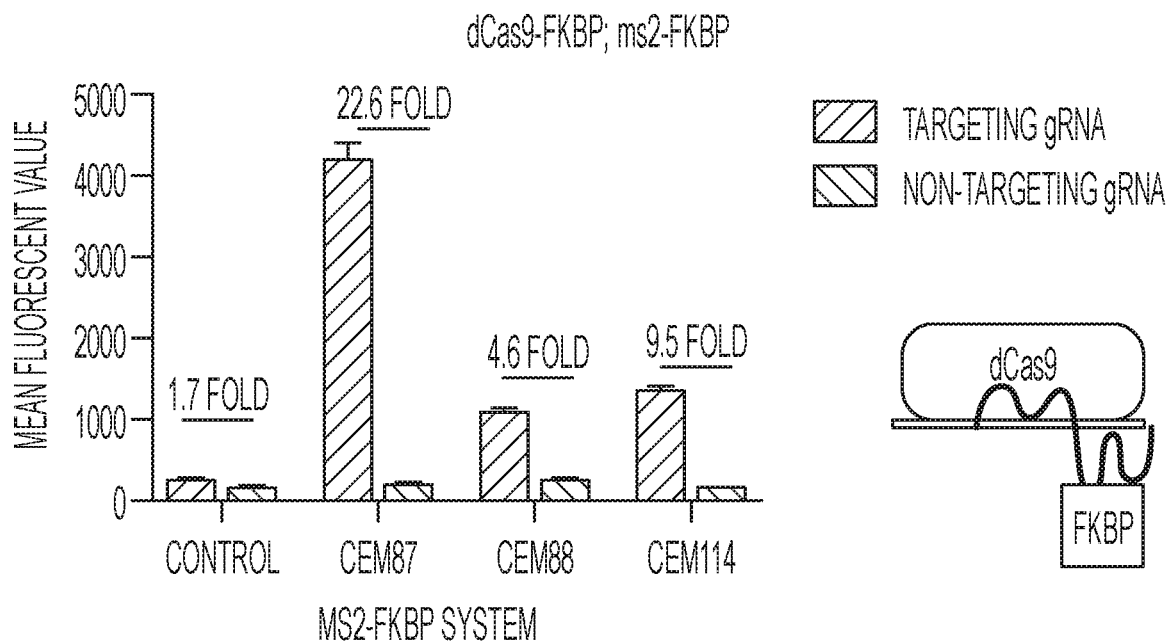
Figure 30F:
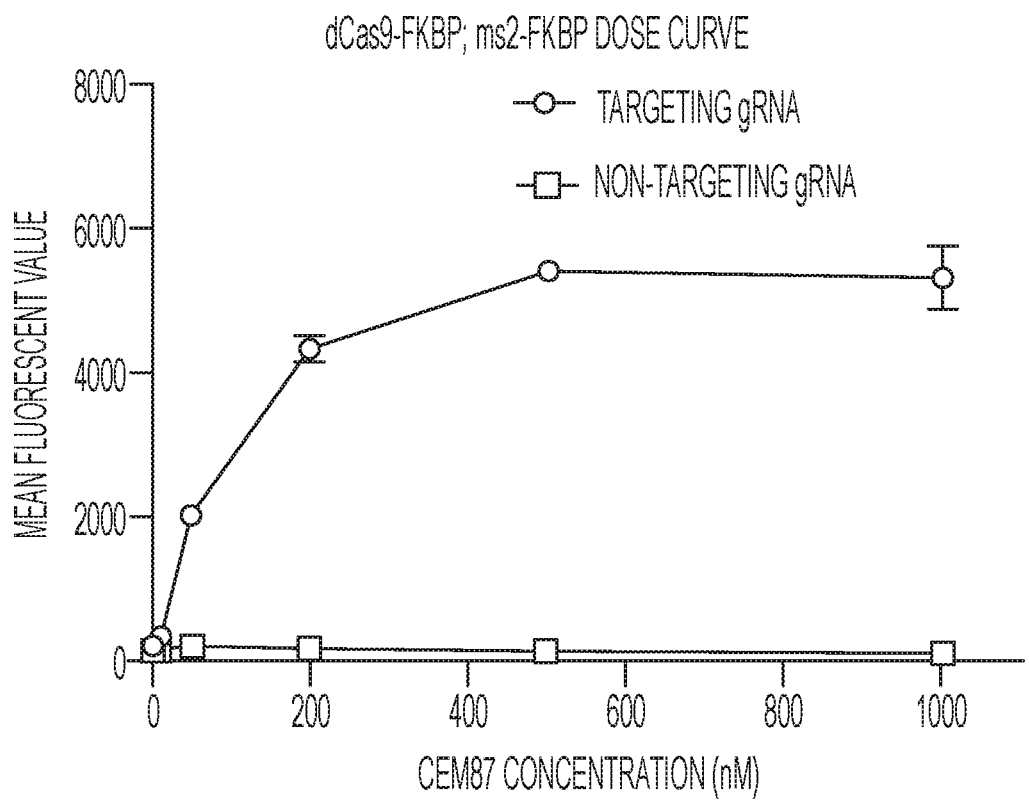

The development of chemical induced proximity (CIP)-reliant tools can depend on a pair of fusion proteins: 1) one that binds to the target genomic sequence; and 2) one that binds to a chromatin modifying protein. Activity is achieved when a CIP is added that rapidly brings the chromatin modifying protein to the specific genomic region of (Hathaway, N. A. et al. Cell 149, 1447-1460 (2012); (MacDonald, I. A. & Hathaway, N. A. Immunol. Cell Biol. 93, 261-270 (2015)). Described herein are two advances in this technology. First, an anchor protein can be adapted to function with a dCas9 system (Gao, Y. et al. Nat. Methods 12, 1-9 (2016)). Thus, chromatin-modifying proteins can be recruited to any locus, with genome-wide specificity, by selecting an appropriate sgRNA to target the anchor protein. Second, chemical tools have been developed that grab endogenous chromatin-modifying enzymes and directly recruit them to the dCas9 targeted locus (FIG. 9A, B). With this approach any gene can be specifically targeted with desired sgRNA, then, bifunctional CEM addition will recruit HDAC (or HAT) activity which de-acetylates (or acetylates in the case of a HAT) the promoter of the target gene and leads to gene repression (or activation). As described herein, novel bi-functional chemical epigenetic modifiers (CEMs), which have a FK-506 end that tightly binds to the FK-506 Binding Protein (FKBP) conjugated to a linker, and attached to an epigenetic inhibitor can be used. HDAC inhibitors can be used to recruit HDAC activity causing target gene repression. In some aspects, bromodomain inhibitors can be used to recruit HAT activity, causing target gene activation. For example, bromodomains (BRDs) can act as "readers" of acetyl marks in histone tails, targeting chromatin-modifying enzymes and other protein machinery to specific sites in the chromatin, thus regulating gene transcription. The advantage of the methods disclosed herein is that bifunctional CEMs can repress or activate gene transcription in a dose-dependent manner so gene expression levels can be exquisitely controlled. And, because epigenetics are selectively effected, and not gene cleavage, the methods can be reversible. Further, FIG. 28 shows that excess FK506 outcompetes CEM23 for the FKBP binding site. This is useful to tightly regulate changes to gene expression allowing for rapid reversal of the biological action. The methods disclosed herein can effectively silence GFP in a chromatin in vivo assay (CiA) mouse ES cells (FIGS. 10A-C). A marked decrease in acetylation levels at the promoter was observed when the repressed cell population was evaluated, demonstrating that the gene repression was caused by active removal of acetylation from HDAC recruitment (FIG. 10D).

Figure 11A:
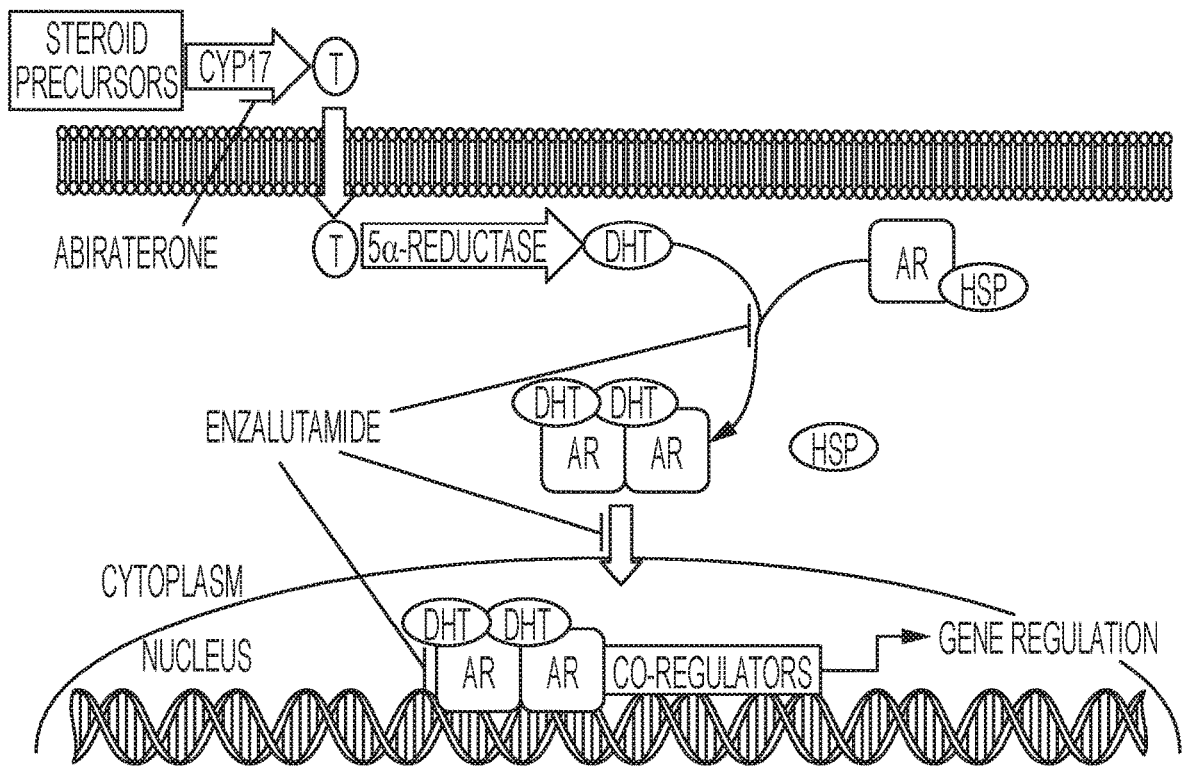
FIGS. 11A-B is a schematic of the androgen receptor (AR).
Figure 11B:
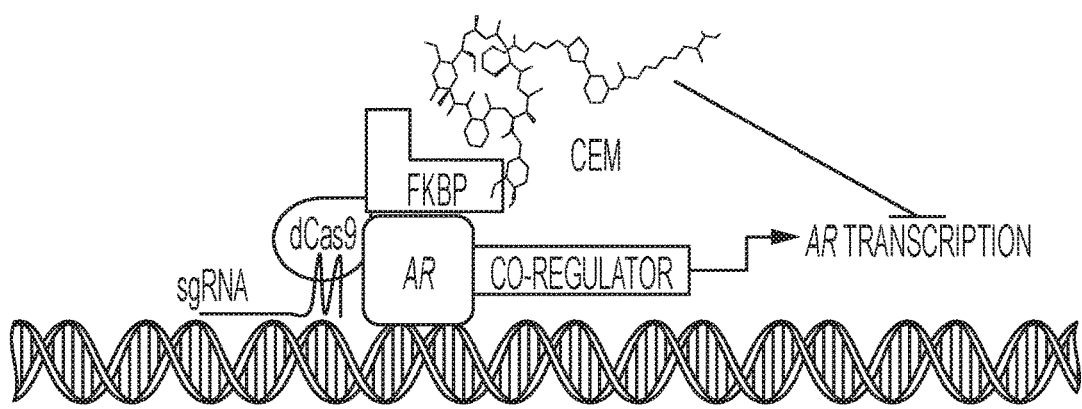

The AR signaling axis is central to both normal prostate development and PC development. Preclinical and clinical models have associated AR expression and the development of mPC, as well as the progression to mCRPC (Delcuve, G. P., Khan, D. H. & Davie, J. R. Clin. Epigenetics 4, 5 (2012); (Tindall, D. & Lonergan, P. A J. Carcinog. 10, 20 (2011)). In PC, the AR translocates into the nucleus and binds to androgen response elements in cis-regulatory regions to regulate transcription of androgen-dependent target genes important to prostate carcinogenesis (see FIG. 11A) (van Royen, M. E., van Cappellen, W. A., de Vos, C., Houtsmuller, J. Cell Sci. 125, 1970-1979 (2012); (Jentzmik, F., Azoitei, A., Zengerling, F., Damjanoski, I. & Cronauer, M. V. World J. Urol. 34, 297-303 (2016)). Transcriptional regulation of target genes through AR signaling contributes to mPC proliferation and survival, which makes AR the representative gene to target with the dCas9-FKBP and CEM technology (see, FIG. 11B). Using CRISPR-Cas9 gene editing technologies for its functional genomics translational research, genetic markers of drug response for patients treated with the multikinase inhibitor sorafenib have been validated. Four candidate genes (RDX, FDXJ, ARHGAP20, and SCMH1) were discovered through mouse genome-wide association study (GWAS) of multiple cell health phenotypes (i.e., cell death, cell membrane permeability, mitochondrial health, etc.). Using CRISPR/Cas9 and CRISPR/Cas9-VPR for gene knockout and gene overexpression, respectively, the influence of each candidate gene on sorafenib cytotoxicity was compared in human and mouse cell lines. After confirming that guide oligonucleotides integrated correctly, Western blotting (WB) confirmed that the gene of interest was knocked down or overexpressed. Dose response curves were created for the phenotypes, and CRISPR/Cas9 effects on sorafenib cytotoxicity were evaluated.

Methods of Treatment

Disclosed herein, are methods of treating cancer in a subject, the method comprising: (a) identifying a subject in need of treatment; and (b) administering to the subject a therapeutically effective amount of a bifunctional CEM.

Also, disclosed herein, are methods of treating an autoimmune disorder in a subject, the method comprising: (a) identifying a subject in need of treatment; and (b) administering to the subject a therapeutically effective amount of a bifunctional CEM.

Disclosed herein are methods recruiting effector proteins in a cell. The method can comprise: a) contacting the cell with a fusion protein comprising a catalytically inactive Cas9 (dCas9) and FK506 binding protein (FKBP), wherein the catalytically inactive Cas9 (dCas9) is bound to a single guide RNA, and wherein the single guide RNA binds upstream of a target gene; b) contacting the cell with a bifunctional chemical epigenetic modifier (CEM) comprising FK506 or a derivative thereof, a linker and a bifunctional ligand; and c) binding the FKBP of the fusion protein to the FK506 or a derivative thereof of the bifunctional CEM; wherein one or more effector proteins are recruited in the cell.

Disclosed herein are methods of recruiting effector proteins in a cell, the method can comprise: a) contacting the cell with a catalytically inactive Cas9 (dCas9) wherein the catalytically inactive Cas9 (dCas9) is bound to a single guide RNA, and wherein the single guide RNA binds upstream of a target gene; b) contacting the cell with FK506 binding protein (FKBP); c) contacting the cell with a bifunctional chemical epigenetic modifier (CEM) comprising FK506 or a derivative thereof, a linker and a bifunctional ligand; and d) binding the FKBP to the FK506 or a derivative thereof of the bifunctional CEM; wherein one or more effector proteins are recruited in the cell. In an aspect, the cell in step b) can be contacted with endogenous or exogenous FKBP.

Disclosed herein are methods of reducing expression of a target gene in a cell. The method can comprise: a) expressing a fusion protein in the cell, wherein the fusion protein comprises a catalytically inactive Cas9 (dCas9), wherein the catalytically inactive Cas9 (dCas9) is bound to a single guide RNA, wherein the single guide RNA binds a nucleic acid sequence upstream of a target gene; b) contacting the cell with FK506 binding protein (FKBP); c) contacting the cell with a bifunctional chemical epigenetic modifier (CEM) comprising a FK506 or a derivative thereof, a linker and a bifunctional ligand, wherein the FK506 binds to the FKBP of the fusion protein; and d) mobilizing effector proteins to the target gene, wherein the effector genes are inhibited by the bifunctional ligand; wherein the expression of the target gene is reduced. In an aspect, the cell in step b) can be contacted with endogenous or exogenous FKBP.

Disclosed herein are methods of increasing expression of a target gene in a cell. The method can comprise: a) expressing a fusion protein in the cell, wherein the fusion protein comprises a catalytically inactive Cas9 (dCas9), wherein the catalytically inactive Cas9 (dCas9) is bound to a single guide RNA, wherein the single guide RNA binds a nucleic acid sequence upstream of a target gene; b) contacting the cell with FK506 binding protein (FKBP); c) contacting the cell with a bifunctional chemical epigenetic modifier (CEM) comprising a FK506 or a derivative thereof, a linker and a bifunctional ligand, wherein the FK506 binds to the FKBP of the fusion protein; and d) mobilizing effector proteins to the target gene, wherein the effector genes are activated by the bifunctional ligand; wherein the expression of the target gene is increased. In an aspect, the cell in step b) can be contacted with endogenous or exogenous FKBP.

In an aspect, the linker can couple the FK506 or derivative thereof to the bifunctional ligand. In an aspect, the linker can be a homofunctional linker or a heterofunctional linker. In an aspect, the homofunctional linker can be a homobifunctional, homotrifunctional, or homotetrafunctional linker comprising two, three, or four reactive groups, respectively, that react with a primary amine, a thiol group, a hydroxyl group, or a carbohydrate, and the heterofunctional linker can be a heterobifunctional, heterotrifunctional, or heterotetrafunctional linker comprising at least one reactive group that reacts with a primary amine, a thiol group, a hydroxyl group, or a carbohydrate. In an aspect the linker can a heterobifunctional, heterotrifunctional, or heterotetrafunctional linker comprising a group reactive with a primary amine and a group reactive with a thiol group. In an aspect, the linker can be a polyethylene glycol. In an aspect, the linker can be cleavable.

In an aspect, the target gene can be the AR gene. In an aspect, the target gene can be the p53 gene. In some aspects, the target gene can be RAS oncogene, NRC31, BRCA2, PARP1, TOP2β, FOXA1, GATA2 and BRD4. In some aspects, the target gene can be BRD3, BRD3, BRPFL. MYODL. CXCR4 or CBP. In some aspects, the target can be transcription factor. In an aspect, the target is tre3g. In some aspects, the target gene can be any tumor suppressor gene. In some aspects, the tumor suppressor gene can be p53, pRb, pVHL, APC, CD95, STS, YPEL3, ST7 or ST14. In some aspects, the target gene can be any oncogene. In some aspects, the oncogene can be one of several categories commonly used for classifying oncogenes including but not limited to: a growth factor or mitogen, receptor tyrosine kinases, cytoplasmic tyrosine kinases, cytoplasmic serine/threonine kinases, regulatory GTPases or transcription factors. In some aspects the oncogene can be c-Sis, epidermal growth factor receptor, platelet-derived growth factor receptor, vascular endothelial growth factor receptor, HER2/neu, Src-family, Syk-ZAP-70 family, and BTK family of tyrosine kinases, the Ab gene in CML—Philadelphia chromosome, Raf kinase, and cyclin-dependent kinases, Ras protein, or the myc gene. In some aspects, the target gene can be any proto-oncogene. In some aspects, the proto-oncogene can be RAS, WNT, MYC, ERK or TRK. In some aspects, the tumor suppressor gene or oncogene (or proto-oncogene) can be related to or associated with one or more neurological disorders or rare disease. In an aspect, the (expression of) target gene can be suppressed (or reduced) or activated (or increased). In an aspect, the bifunctional ligand can be an inhibitor and the target gene can be suppressed (or reduced). In an aspect, the bifunctional ligand can be an activator and the target gene can be activated or its expression can be increased.

Determining the expression level of one or more genes disclosed herein can include determining whether the gene is upregulated or increased or activated as compared to a control or reference sample, downregulated or decreased or suppressed or inhibited or reduced compared to a control or reference sample, or unchanged compared to a control or reference sample. As used herein, the terms, "upregulated" and "increased expression level" or "increased level of expression" refers to a sequence corresponding to one or more genes disclosed herein that is expressed wherein the measure of the quantity of the sequence exhibits an increased level of expression when compared to a reference sample or "normal" control. For example, the terms, "upregulated" and "increased expression level" or "increased level of expression" refers to a sequence corresponding to one or more genes disclosed herein that is expressed wherein the measure of the quantity of the sequence exhibits an increased level of expression of, for example, the AR gene, AR protein and/or mRNA when compared to the expression of the same gene, protein, mRNA(s) from a reference sample or "normal" control. An "increased expression level" refers to an increase in expression of at least 1%, 2%, 3%, 4%, 5%, 6%, 7%, 8%, 9%, 10% or more, for example, 20%, 30%, 40%, or 50%, 60%, 70%, 80%, 90% or more, or greater than 1-fold, up to 2-fold, 3-fold, 4-fold, 5-fold, 10-fold, 50-fold, 100-fold or more. As used herein, the terms "downregulated," "decreased level of expression," or "decreased expression level" refers to a sequence corresponding to one or more genes disclosed herein that is expressed wherein the measure of the quantity of the sequence exhibits a decreased level of expression when compared to a reference sample or "normal" control For example, the terms "downregulated," "decreased level of expression," or "decreased expression level" refers to a sequence corresponding to one or more genes disclosed herein that is expressed wherein the measure of the quantity of the sequence exhibits a decreased level of expression of, for example, AR gene, protein and/or mRNA when compared to the expression of the same gene, protein or mRNA(s) from a reference sample or "normal" control. A "decreased level of expression" refers to a decrease in expression of at least 1%, 2%, 3%, 4%, 5%, 6%, 7%, 8%, 9%, 10% or more, for example, 20%, 30%, 40%, or 50%, 60%, 70%, 80%, 90% or more, or greater than 1-fold, up to 2-fold, 3-fold, 4-fold, 5-fold, 10-fold, 50-fold, 100-fold or more.

In an aspect, the bifunctional ligand can be an activator or an inhibitor. Examples of inhibitors include but are not limited to bromodomain inhibitors, chromobox family (CBX) domain inhibitors, methyl-CpG-binding domain (MBD) inhibitors, inhibitors that bind to any transcriptional machinery, and DNA methylation inhibitors. In an aspect, the bifunctional ligand can be an epigenetic inhibitor. In an aspect, the bifunctional ligand can be an epigenetic activator. In an aspect, the epigenetic inhibitor can be a histone deacetylase inhibitor. Examples of HDAC inhibitors include but are not limited to vorinostat (e.g., suberanilohydroxamic acid (SAHA), depsipeptide (e.g., romidepsin, FK228), and derivatives thereof.

In an aspect, the one or more effector proteins can be enzymes. In an aspect, the enzyme can be histone deacetylase. In an aspect, the enzyme can be HDAC1 and/or HDAC3. In an aspect, the enzyme can be histone acetyl transferase (HAT) or a lysine reader protein. In an aspect, enzyme can be p300/CBP. In an aspect, enzyme can be histone methyltransferase (HMT). In an aspect, enzyme can be a DNA methylase.

Disclosed herein are methods that utilize a nuclease-dead version of Cas9 (dCas9). In an aspect, the dCas9 can be derived from *Streptococcus pyogenes, Streptococcus* thermophiles or Neisseeria *meningitides*. dCas9 is the protein that interacts with gRNAs to place the desired editing proteins to specific sites. In an aspect, dCas9 can be used to repress or activate expression of one or more target genes. dCas9 can be used to silence (downregulate or turn off one or more genes). Instead of inducing cleavage, dCas9 remains bound tightly to the DNA sequence, and when targeted inside an actively transcribed gene, inhibition of, for example, pol II progression through a steric hindrance mechanism can lead to efficient transcriptional repression.

In some aspects, the methods utilize a nuclease-dead version of Cas9 (dCas9) that can be optimized. For example, disclosed herein are methods of increasing expression of a target gene in a cell, the method comprising: a) expressing a fusion protein in the cell, wherein the fusion protein comprises a catalytically inactive Cas9 (dCas9), wherein the catalytically inactive Cas9 (dCas9) is bound to one or more guide RNA(s), wherein the more one or more guide RNA(s) bind a nucleic acid sequence upstream or downstream of a target gene; b) contacting the cell with FK506 binding protein (FKBP); c) contacting the cell with a bifunctional chemical epigenetic modifier (CEM) comprising a FK506 or a derivative thereof, a linker and a bifunctional ligand, wherein the FK506 binds to the FKBP of the fusion protein; and d) mobilizing effector proteins to the target gene, wherein the effector genes are activated by the bifunctional ligand; wherein the expression of the target gene is increased.

In some aspects, the methods described herein can utilize a multiplexing gRNA plasmid whereby the cells can express multiple (e.g., two or more) gRNA sequences.

In some aspects, the methods described herein can utilize a dCas9 "SunTag" system that is compatible with the CEM compositions and methods described herein. For example, a dCas9-SunTagx10 plasmid can be used that expresses an array of 10 yeast-specific GCN4 (gene control protein 4) peptides from the C-terminus of the dCas9. In some aspects, the methods can further comprise co-transfecting the cells with a single chain variable fragment (scFv), (e.g. made to be GCN4-specific) fused to FKBP.

In some aspects, the methods described herein can incorporate ms2-compatible gRNAs. In some aspects, the ms2-compatible gRNAs have a modified stem-loop, capable of recruiting both a dCas9-fusion as well as a bacteriophage MS2 coat protein (MCP)-fusion. Such methods can increase the number of FKBPs by 2-fold (as two MCP fusions can bind one stem loop) and can physically increase the proximity of recruited CEMa to the chromatin.

Other methods of genome engineering (e.g., expressing a fusion protein in a cell) can be used in the methods disclosed herein. In some aspects, gene editing can be carried out by inducing a double-stranded break (DSB) in a defined position in the genome near the desired alteration. DSBs can be induced using any DSB-inducing agent available, including, but not limited to, zinc-finger nucleases (ZFNs), transcription activator-like effector nucleases (TALENs), meganucleases, Cas9-gRNA systems (based on bacterial CRISPR-Cas9 systems), and the like. Genome editing techniques using DSB-inducing agents, such as Cas9-gRNA complexes, are known in the art. Guide polynucleotide/Cas endonuclease systems are also known in the art. Additional uses for guide RNA/Cas endonuclease systems include, but are not limited to, modifying or replacing nucleotide sequences of interest (e.g., regulatory elements), insertion of polynucleotides of interest, gene knock-out, gene-knock in, modification of splicing sites and/or introducing alternate splicing sites, modifications of nucleotide sequences encoding a protein of interest, amino acid and/or protein fusions, and gene silencing by expressing an inverted repeat into a gene of interest. The design and select of sgRNAs and gRNAs are within the ability of one of ordinary skill in the art.

The compositions described herein can be formulated to include a therapeutically effective amount of a bifunctional CEM described herein. In an aspect, the compositions described herein can be formulated to include a therapeutically effective amount of a bifunctional ligand described herein. Therapeutic administration encompasses prophylactic applications. Based on genetic testing and other prognostic methods, a physician in consultation with their patient can choose a prophylactic administration where the patient has a clinically determined predisposition or increased susceptibility (in some cases, a greatly increased susceptibility) to a type of cancer or autoimmune disorder.

The compositions described herein can be administered to the subject (e.g., a human patient) in an amount sufficient to delay, reduce, or preferably prevent the onset of clinical disease. Accordingly, in some aspects, the patient can be a human patient. In therapeutic applications, compositions can be administered to a subject (e.g., a human patient) already with or diagnosed with cancer (or autoimmune disorder) in an amount sufficient to at least partially improve a sign or symptom or to inhibit the progression of (and preferably arrest) the symptoms of the condition, its complications, and consequences. An amount adequate to accomplish this is defined as a "therapeutically effective amount." A therapeutically effective amount of a composition (e.g., a pharmaceutical composition) can be an amount that achieves a cure, but that outcome is only one among several that can be achieved. As noted, a therapeutically effective amount includes amounts that provide a treatment in which the onset or progression of the cancer (or autoimmune disorder) is delayed, hindered, or prevented, or the cancer (or autoimmune disorder) or a symptom of the cancer (or autoimmune disorder) is ameliorated. One or more of the symptoms can be less severe. Recovery can be accelerated in an individual who has been treated.

In some aspects, the cancer can be a primary or secondary tumor. In an aspect, the cancer can be a metastatic tumor. In other aspects, the primary or secondary tumor can be within the patient's breast, prostate, or colon. In an aspect, the primary or secondary tumor can be in any cell type or organ. For example, methods disclosed herein can be useful to treat any primary or secondary tumor that is associated with or driven by any mis-regulated gene.

Disclosed herein, are methods of treating a patient with cancer. The cancer can be any cancer. In some aspects, the cancer can be breast cancer, prostate cancer, or colon cancer. In an aspect, the subject has been diagnosed with cancer prior to the administering step. In an aspect, the cancer can be associated with expression of androgen receptor. In some aspects, the cancer can prostate cancer, castrate-resistant prostate cancer, triple negative breast cancer or urothelial carcinoma.

Disclosed herein, are methods of treating a patient with an autoimmune disorder or disorder. In some aspects, the autoimmune disorder or disease can be non-Hodgkin's lymphoma, rheumatoid arthritis, chronic lymphocytic leukemia, multiple sclerosis, systemic lupus erythematosus, autoimmune hemolytic anemia, pure red cell aplasia, idiopathic thrombocytopenic purpura, Evans syndrome, vasculitis, bullous skin disorders, type 1 diabetes mellitus, Sjögren's syndrome, Devic's disease, or Graves' disease ophthalmopathy. In other aspects, the autoimmune disease can be Type I diabetes mellitus, multiple sclerosis, or rheumatoid arthritis.

The therapeutically effective amount or dosage of the bifunctional CEM or any component of the bifunctional CEM used in any of the methods as disclosed herein applied to mammals (e.g., humans) can be determined by one of ordinary skill in the art with consideration of individual differences in age, weight, sex, other drugs administered and the judgment of the attending clinician. Variations in the needed dosage may be expected. Variations in dosage levels can be adjusted using standard empirical routes for optimization. The particular dosage of a pharmaceutical composition to be administered to the patient will depend on a variety of considerations (e.g., the severity of the cancer or autoimmune disorder symptoms), the age and physical characteristics of the subject and other considerations known to those of ordinary skill in the art Dosages can be established using clinical approaches known to one of ordinary skill in the art. In an aspect, the pharmaceutical formulation can be a unit dosage formulation.

The duration of treatment with any composition provided herein can be any length of time from as short as one day to as long as the life span of the host (e.g., many years). For example, the compositions can be administered once a week (for, for example, 4 weeks to many months or years); once a month (for, for example, three to twelve months or for many years); or once a year for a period of 5 years, ten years, or longer. It is also noted that the frequency of treatment can be variable. For example, the present compositions can be administered once (or twice, three times, etc.) daily, weekly, monthly, or yearly.

The total effective amount of the compositions as disclosed herein can be administered to a subject as a single dose, either as a bolus or by infusion over a relatively short period of time, or can be administered using a fractionated treatment protocol in which multiple doses are administered over a more prolonged period of time. Alternatively, continuous intravenous infusions sufficient to maintain therapeutically effective concentrations in the blood are also within the scope of the present disclosure.

The compositions described herein can be formulated in a variety of combinations. The compositions described herein can be administered in a variety of combinations. The particular combination of any of the bifunctional CEMs with one or more therapeutic agent can vary according to many factors, for example, the particular type and severity of the cancer (or autoimmune disease).

Any of the compositions described herein can be administered as a term "combination." It is to be understood that, for example, a bifunctional CEM can be provided to the subject in need, either prior to administration of one or more therapeutic agents, concomitant with administration of said one or more therapeutic agents (co-administration) or shortly thereafter or prior to.

In some instances, the disclosed methods of treating cancer or an autoimmune disorder further comprise administering a therapeutic agent. In some instances, the therapeutic agent can be, but is not limited to, conventional chemotherapy, vaccines, monoclonal antibodies, T cell immunotherapies, and other immunomodulatory agents.

Any of the bifunctional CEMs described herein may be used in combination with other known agents and therapies. Administered "in combination", as used herein, means that two (or more) different treatments are delivered to the subject during the course of the subject's affliction with the disorder, e.g., the two or more treatments can be delivered after the subject has been diagnosed with the disorder and before the disorder has been cured or eliminated or treatment has ceased for other reasons. In some embodiments, the delivery of one treatment is still occurring when the delivery of the second begins, so that there can be overlap in terms of administration. This is sometimes referred to herein as "simultaneous" or "concurrent delivery". In other embodiments, the delivery of one treatment ends before the delivery of the other treatment begins. In some embodiments of either case, the treatment can be more effective because of combined administration. For example, the second treatment can be more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

Any of the bifunctional CEMs described herein and the at least one additional therapeutic agent can be administered simultaneously, in the same or in separate compositions, or sequentially. For sequential administration, the bifunctional CEM described herein can be administered first, and the additional agent can be administered second, or the order of administration can be reversed.

In one embodiment, a bifunctional CEM described herein can be used in combination with a chemotherapeutic agent. Exemplary chemotherapeutic agents include an anthracycline (e.g., doxorubicin (e.g., liposomal doxorubicin)), a *vinca* alkaloid (e.g., vinblastine, vincristine, vindesine, vinorelbine), an alkylating agent (e.g., cyclophosphamide, decarbazine, melphalan, ifosfamide, temozolomide), an immune cell antibody (e.g., alemtuzamab, gemtuzumab, rituximab, tositumomab), an antimetabolite (including, e.g., folic acid antagonists, pyrimidine analogs, purine analogs and adenosine deaminase inhibitors (e.g., fludarabine)), an mTOR inhibitor, a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide).

General chemotherapeutic agents considered for use in combination therapies include anastrozole (Arimidex®), bicalutamide (Casodex®), bleomycin sulfate (Blenoxane), busulfan (Myleran®), busulfan injection (Busulfex®), capecitabine (Xeloda), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegen), daunorubicin hydrochloride (Cerubidine®), daunorubicin citrate liposome injection (DaunoXome®), dexamethasone, docetaxel (Taxotere), doxorubicin hydrochloride (Adriamycin®, Rubex®), etoposide (Vepesid®), fludarabine phosphate (Fludara), 5-fluorouracil (Adrucil®, Efudex®), flutamide (Eulexin®), tezacitibine, Gemcitabine (difluorodeoxycitidine), hydroxyurea (Hydrea), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Anti-cancer agents of particular interest for combinations with the bifunctional CEMs of the present invention include: anthracyclines; alkylating agents; antimetabolites; drugs that inhibit either the calcium dependent phosphatase calcineurin or the p70S6 kinase FK506) or inhibit the p70S6 kinase; mTOR inhibitors; immunomodulators; anthracyclines; *vinca* alkaloids; proteosome inhibitors; GITR agonists; protein tyrosine phosphatase inhibitors; a CDK4 kinase inhibitor; a BTK inhibitor; a MKN kinase inhibitor; a DGK kinase inhibitor; or an oncolytic virus.

Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Ibioplex®); Cyclophosphamide (Endoxan®, Cytoxan®, Neosar®, Procytox®, Revimmune®); and Bendamustine HCl (Treanda®).

Exemplary mTOR inhibitors include, e.g., temsirolimus; ridaforolimus (formally known as deferolimus, (1R,2R,4S)-4-[(2R)-2 [(1R,9S,12S,15R,16E,18R,19R,21R, 23S,24E, 26E,28Z,30S,32S,35R)-1,18-dihydroxy-19,30-dimethoxy-15,17,21,23,29,35-hexamethyl-2,3,10,14,20-pentaoxo-11, 36-dioxa-4-azatricyclo[30.3.1.04,9]hexatriaconta-16,24,26, 28-tetraen-12-yl]propyl]-2-methoxycyclohexyl dimethylphosphinate, also known as AP23573 and MK8669, and described in PCT Publication No. WO 03/064383); everolimus (Afinitor® or RAD001); rapamycin (AY22989, Sirolimus®); simapimod (CAS 164301-51-3); emsirolimus, (5-{2,4-Bis[(3S)-3-methylmorpholin-4-yl] pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d] pyrimidin-7(8H)-one (PF04691502, CAS 1013101-36-4); and N2-[1,4-dioxo-[[4-(4-oxo-8-phenyl-4H-1-benzopyran-2-yl)morpholinium-4-yl]methoxy]butyl]-L-arginylglycyl-L-α-aspartylL-serine, inner salt (SF1126, CAS 936487-67-1), and XL765.

Exemplary immunomodulators include, e.g., afutuzumab (available from Roche); pegfilgrastim (Neulasta®); lenalidomide (CC-5013, Revlimid®); thalidomide (Thalomid®), actimid (CC4047); and IRX-2 (mixture of human cytokines including interleukin 1, interleukin 2, and interferon γ, CAS 951209-71-5, available from IRX Iherapeutics).

Exemplary anthracyclines include, e.g., doxorubicin (Adriamycin® and Rubex®); bleomycin (Lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone); epirubicin (Ellence™); idarubicin (Idamycin®, Idamycin PFS®); mitomycin C (Mutamycin®); geldanamycin; herbimycin; ravidomycin; and desacetylravidomycin.

Exemplary *vinca* alkaloids include, e.g., vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®).

Exemplary proteosome inhibitors include bortezomib (Velcade(g); carfilzomib (PX-171-007, (S)-4-Methyl-N-((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)-pentanamide); marizomib (NPI-0052); ixazomib citrate (MLN-9708); delanzomib (CEP-18770); and O-Methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-L-serinamide (ONX-0912).

In embodiments, a bifunctional CEM described herein is administered to a subject in combination with an anti-androgen. In embodiments, a bifunctional CEM described herein is administered to a subject in combination with abiraterone (Zytiga®) and/or enzalutamide (Xtandi®). In embodiments, the subject has prostate cancer. In some embodiments, the combination therapy further includes prednisone.

Pharmaceutical Compositions

As disclosed herein, are pharmaceutical compositions, comprising a bifunctional CEM and a pharmaceutical acceptable carrier described herein. In some aspects, the bifunctional CEMs can be formulated for oral or parental administration. In an aspect, the parental administration is intravenous, subcutaneous, intramuscular or direct injection. The compositions can be formulated for administration by any of a variety of routes of administration, and can include one or more physiologically acceptable excipients, which can vary depending on the route of administration. As used herein, the term "excipient" means any compound or substance, including those that can also be referred to as "carriers" or "diluents." Preparing pharmaceutical and physiologically acceptable compositions is considered routine in the art, and thus, one of ordinary skill in the art can consult numerous authorities for guidance if needed.

The compositions can be administered directly to a subject. Generally, the compositions can be suspended in a pharmaceutically acceptable carrier (e.g., physiological saline or a buffered saline solution) to facilitate their delivery. Encapsulation of the compositions in a suitable delivery vehicle (e.g., polymeric microparticles or implantable devices) may increase the efficiency of delivery.

The compositions can be formulated in various ways for parenteral or nonparenteral administration. Where suitable, oral formulations can take the form of tablets, pills, capsules, or powders, which may be enterically coated or otherwise protected. Sustained release formulations, suspensions, elixirs, aerosols, and the like can also be used.

Pharmaceutically acceptable carriers and excipients can be incorporated (e.g., water, saline, aqueous dextrose, and glycols, oils (including those of petroleum, animal, vegetable or synthetic origin), starch, cellulose, talc, glucose, lactose, sucrose, gelatin, malt, rice, flour, chalk, silica gel, magnesium stearate, sodium stearate, glycerol monosterate, sodium chloride, dried skim milk, glycerol, propylene glycol, ethanol, and the like). The compositions may be subjected to conventional pharmaceutical expedients such as sterilization and may contain conventional pharmaceutical additives such as preservatives, stabilizing agents, wetting or emulsifying agents, salts for adjusting osmotic pressure, buffers, and the like. Suitable pharmaceutical carriers and their formulations are described in "Remington's Pharmaceutical Sciences" by E.W. Martin, which is herein incorporated by reference. Such compositions will, in any event, contain an effective amount of the compositions together with a suitable amount of carrier so as to prepare the proper dosage form for proper administration to the patient.

The pharmaceutical compositions as disclosed herein can be prepared for oral or parenteral administration. Pharmaceutical compositions prepared for parenteral administration include those prepared for intravenous (or intra-arterial), intramuscular, subcutaneous, intraperitoneal, transmucosal (e.g., intranasal, intravaginal, or rectal), or transdermal (e.g., topical) administration. Aerosol inhalation can also be used. Thus, compositions can be prepared for parenteral administration that includes a molecule of FK506 or derivative thereof, a linker and a bifunctional ligand dissolved or suspended in an acceptable carrier, including but not limited to an aqueous carrier, such as water, buffered water, saline, buffered saline (e.g., PBS), and the like. One or more of the excipients included can help approximate physiological conditions, such as pH adjusting and buffering agents, tonicity adjusting agents, wetting agents, detergents, and the like. Where the compositions include a solid component (as they may for oral administration), one or more of the excipients can act as a binder or filler (e.g., for the formulation of a tablet, a capsule, and the like).

The pharmaceutical compositions can be sterile and sterilized by conventional sterilization techniques or sterile filtered. Aqueous solutions can be packaged for use as is, or lyophilized, the lyophilized preparation, which is encompassed by the present disclosure, can be combined with a sterile aqueous carrier prior to administration. The pH of the pharmaceutical compositions typically will be between 3 and 11 (e.g., between about 5 and 9) or between 6 and 8 (e.g., between about 7 and 8). The resulting compositions in solid form can be packaged in multiple single dose units, each containing a fixed amount of the above-mentioned agent or agents, such as in a sealed package of tablets or capsules.

Articles of Manufacture

The composition described herein can be packaged in a suitable container labeled, for example, for use as a therapy to treat cancer or an autoimmune disorder or any of the methods disclosed herein. Accordingly, packaged products (e.g., sterile containers containing the composition described herein and packaged for storage, shipment, or sale at concentrated or ready-to-use concentrations) and kits, including at least a bifunctional CEM as described herein and instructions for use, are also within the scope of the disclosure. A product can include a container (e.g., a vial, jar, bottle, bag, or the like) containing the composition described herein. In addition, an article of manufacture further may include, for example, packaging materials, instructions for use, syringes, buffers or other control reagents for treating or monitoring the condition for which prophylaxis or treatment is required. The product may also include a legend (e.g., a printed label or insert or other medium describing the product's use (e.g., an audio- or videotape)). The legend can be associated with the container (e.g., affixed to the container) and can describe the manner in which the compound therein should be administered (e.g., the frequency and route of administration), indications therefor, and other uses. The compounds can be ready for administration (e.g., present in dose-appropriate units), and may include a pharmaceutically acceptable adjuvant, carrier or other diluent. Alternatively, the compounds can be provided in a concentrated form with a diluent and instructions for dilution.

EXAMPLES

Example 1: Design of Chemical Epigenetic Modifiers

The Chromatin in vivo assay (CiA) cell line was used to develop bivalent ligands capable of epigenome editing, referred herein as bifunctional chemical epigenetic modifiers (CEMs) (Hathaway, N. a. et al. *Cell* 149, 1447-1460 (2012)). This cell line is derived from mouse embryonic stem cells (mESC). One copy of the Pou5F locus is modified to include a Gal4 DNA-binding array upstream of the transcriptional start site, and the downstream Oct4 gene is replaced with enhanced GFP (eGFP). Because the eGFP gene is highly expressed, this system is sensitive to the recruitment of gene silencing complexes, and the change in gene expression can be monitored by flow cytometry.

The mESCs were lentivirally infected with a plasmid expressing an FKBP-Gal4 fusion protein, which serves as our DNA-anchor to recruit the CEMs (FIG. 1A). This was important for development of the CEM system because FK506 forms a high affinity interaction with FKBP and can serve as the transcription factor ligand. Guo, Z.-F., Zhang, R. & Liang, F.-S. *RSC Adv.* 4, 11400 (2014). The control cell line expresses the unmodified Gal4 protein, removing the ability to bind and recruit FK506.

The bifunctional CEMs were constructed by attaching FK506 to an HDAC inhibitor through a short linker using click chemistry, so as not to disturb the stereocenters of FK506 (FIG. 1B) (Guo, Z.-F., Zhang, R. & Liang, F.-S. *RSC Adv.* 4, 11400 (2014); Hong, V., Presolski, S. I., Ma, C. & Finn, M. G. *Angew. Chemie-Int. Ed.* 48, (2009)). HDAC inhibitors can be attached to linkers or solid supports through the solvent-exposed aryl region with little impact on potency. Kozikowski et al. reported click-chemistry compatible triazole HDAC inhibitors with low-nM potency at HDACs 1, 2, 3, 6, and 10 (Chen, Y. et al. *J. Med. Chem.* 51, 3437-3448 (2008)). This template was used to create CEM42 and CEM23, which contain either a 3×PEG or a propyl linker, respectively (FIG. 1B).

Cell lines and infection. The CiA mouse embryonic stem cells, previously described in Hathaway et al., 2012, were grown on 0.1% gelatin coated tissue culture dishes in high-glucose DMEM (Corning, 10-013-CV) supplemented with FBS serum (Gibo, 26140-079), 10 mM HEPES (Corning, 25-060-Cl), NEAA (Gibco, 11140-050), Pen/Strep, 55 µM 2-Mercaptoethanol, and 1:500 LIF conditioned media produced from LIF-1Cα (COS) cells. Low passage (22-30) mESC were used. Cells were typically passaged at a density of 3-4×10$^6$ cells per 10 cm plate, fed every day, and split every 2-3 days.

Lenti virus production of mESC infection was done using 293T LentiX cells (Clontech). Low passage cells were plated onto 15 cm cells such that they were 80% confluent 24 hours later. Each plate was transfected with 18 µg of the plasmid of interest, 13.5 µg of the Gag-Pol expressing plasmid, and 4.5 µg of the VSV-G envelope expressing plasmid. PEI transfection was done and 60 hours after transfection, virus was spun down at 20,000 RPM for 2½ hours and then added to the mESCs in combination with 5 µg/mL Polybrene (Santa Cruz, sc-134220). Selection of lentiviral constructs was done with either puromycin (1.5 µg/mL) or blasticidin (7.5 µg/mL).

CEM (e.g., linker and bifunctional ligand) and FK506 were diluted in DMSO (Sigma D2650) and kept at −20° C. added to the cells during cell passaging and the cells were given fresh media and compound daily.

Figure 2A:
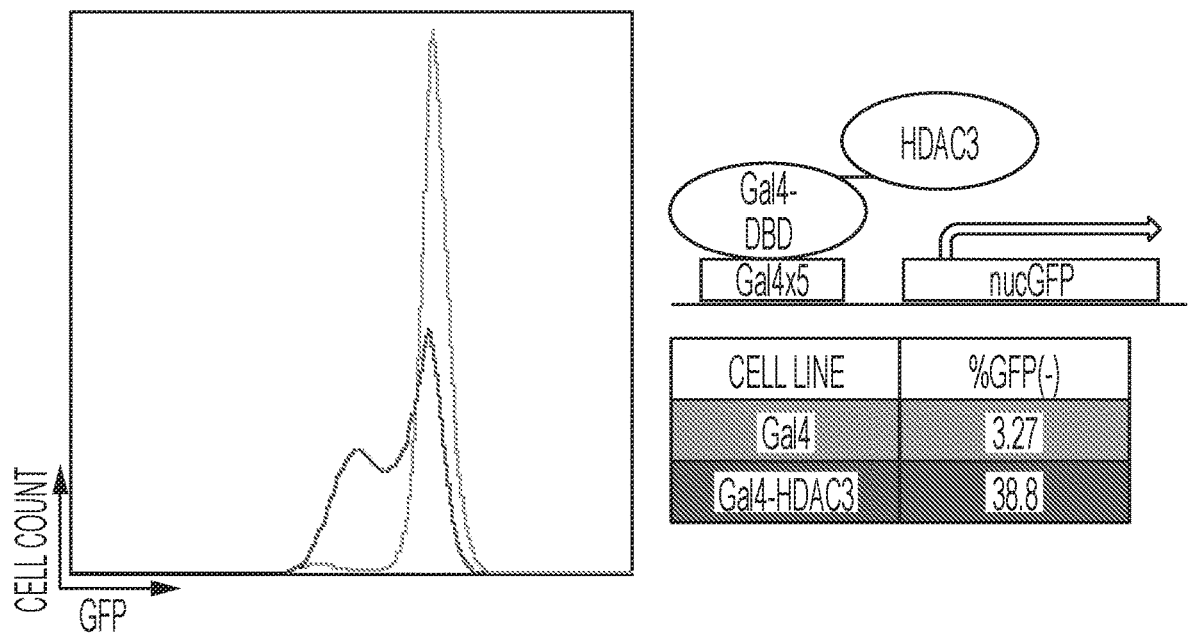
FIGS. 2A-2E show that CEM23 reversibly and specifically represses GFP expression.

Example 2: Recruitment of HDAC Activity can Efficiently Repress the CL4:Oct4 Locus To serve as a positive control for HDAC-mediated repression, fusion proteins between Gal4 and 8 different HDAC isozymes were developed. HDAC3-Gal4 caused repression in 38.8% of the cells (FIG. 2A), while the other fusions did not have any repressive effects.

Figure 2B:
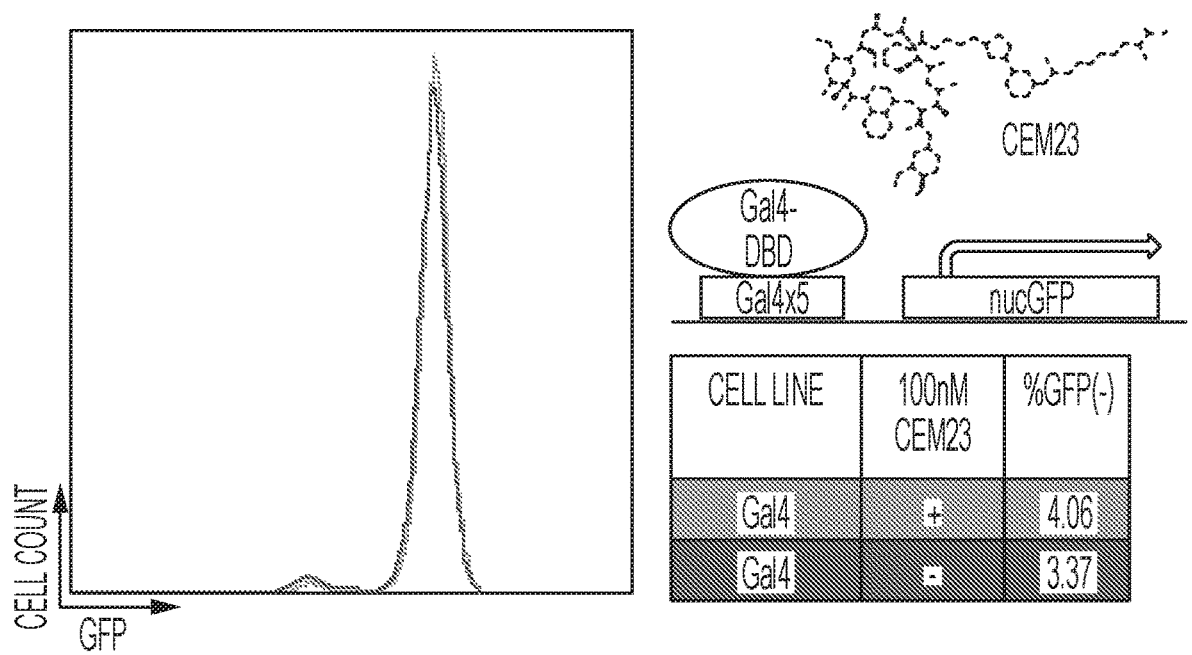
Figure 2C:
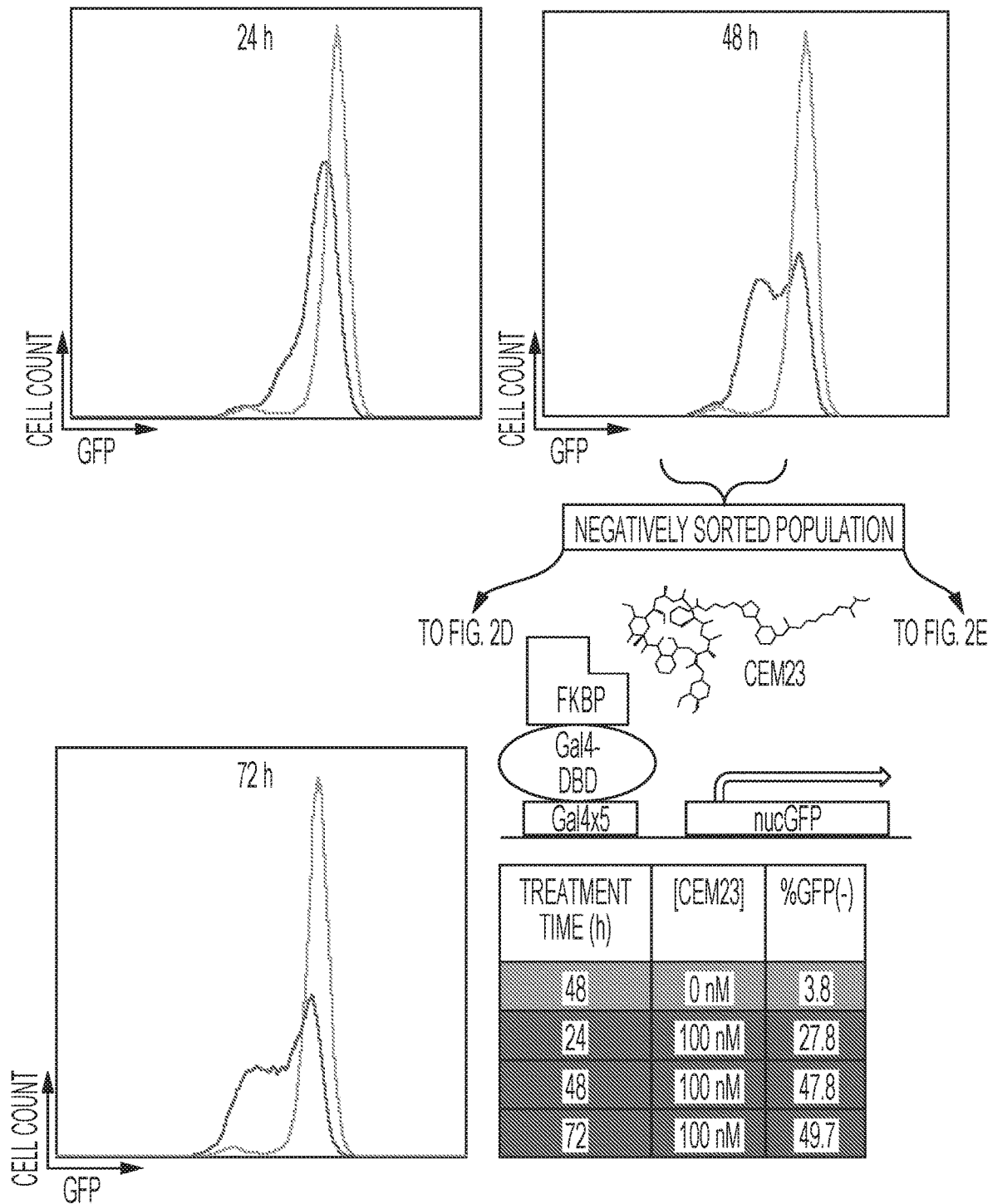
Figure 2D:
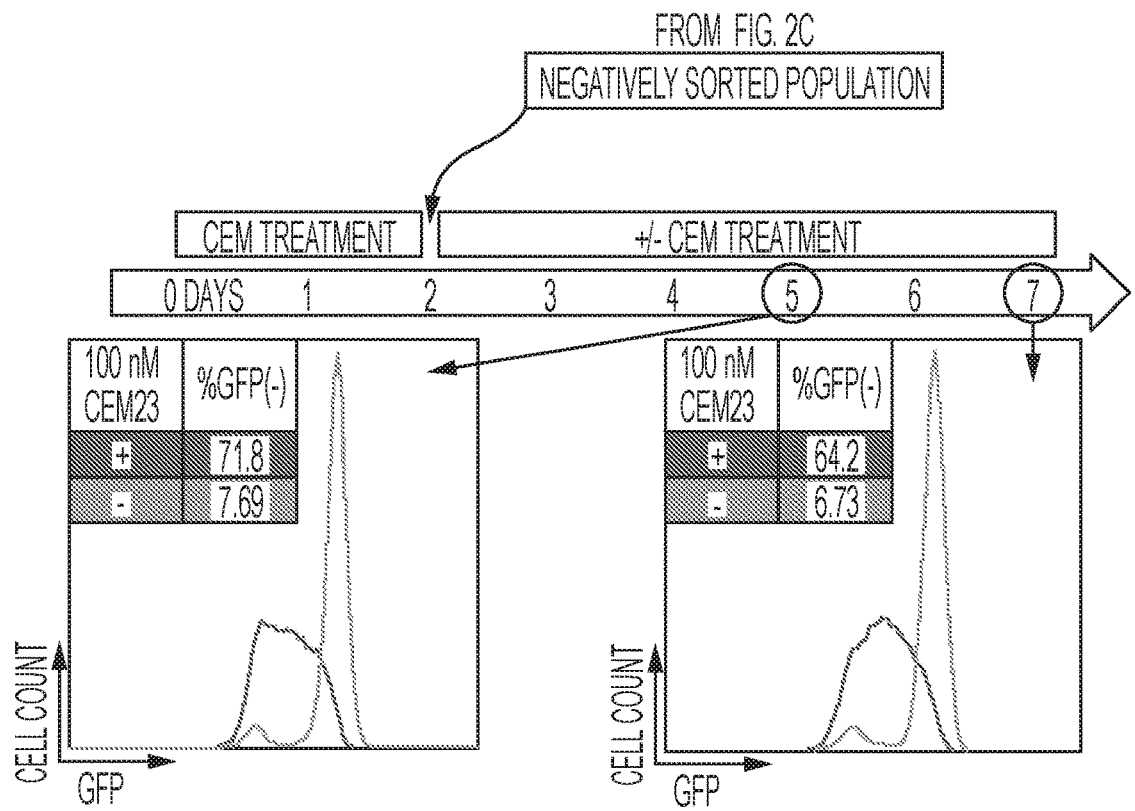

Dose response experiments identified the optimal concentration of CEM23. Cellular response started at 10 nM and reached a maximum at 100 nM (FIG. 3A). FKBP-Gal4 cells treated with 100 nM CEM23 were followed for 72 hours. The cell population reached a maximum of 48% GFP(−) after 48 hours, and sustained this level through 72 hours (FIG. 2C). In cells transfected with Gal4, which cannot recruit the bifunctional CEMs, 100 nM of CEM23 did not cause a significant increase in the GFP(−) population (FIG. 2B). The Gal4 control experiment proves that any changes in gene expression are not due to the general gene-silencing effect of the HDAC inhibitors, but are a result of the inhibitor being localized at the target gene. It also shows that the gene silencing is not caused by Gal4 blocking progression of RNA polymerase. Next, the cells were exposed to CEM23 with and without an excess of FK506 (e.g., the component of CEM23 that binds to FKBP). The results show that with a 10λ excess of FK506, the repressive effects of CEM23 are removed, so FK506 is competing with CEM23 for the same FKBP binding site (FIG. 3D).

Figure 2E:
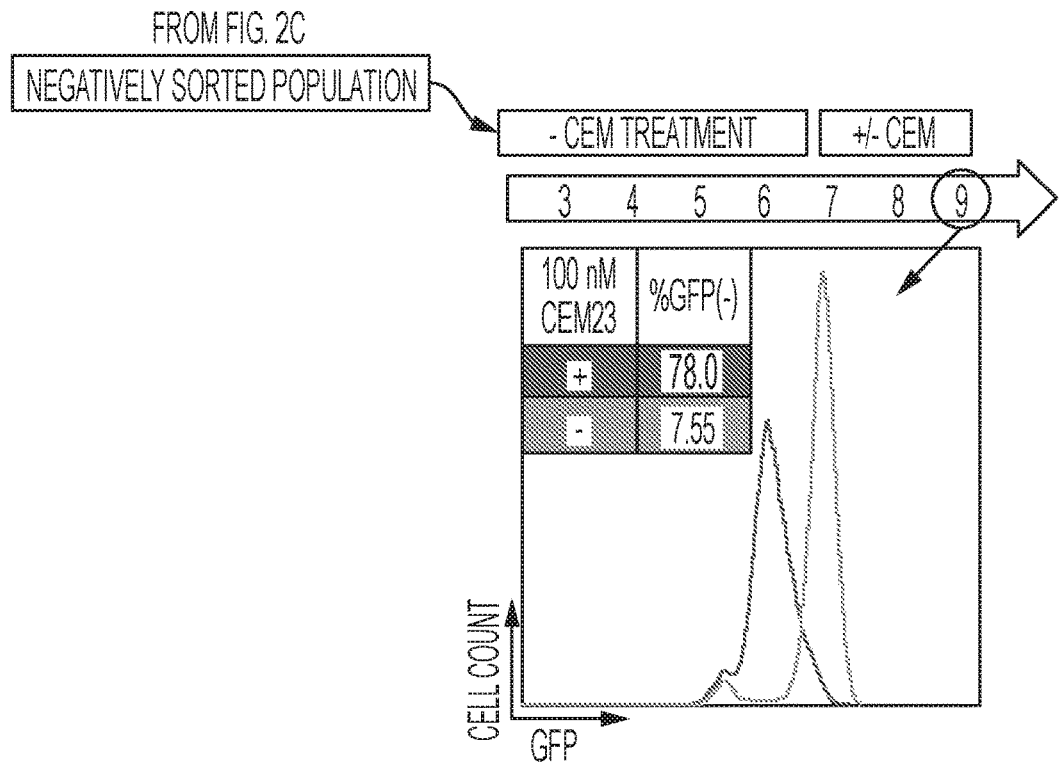
Figure 4A:
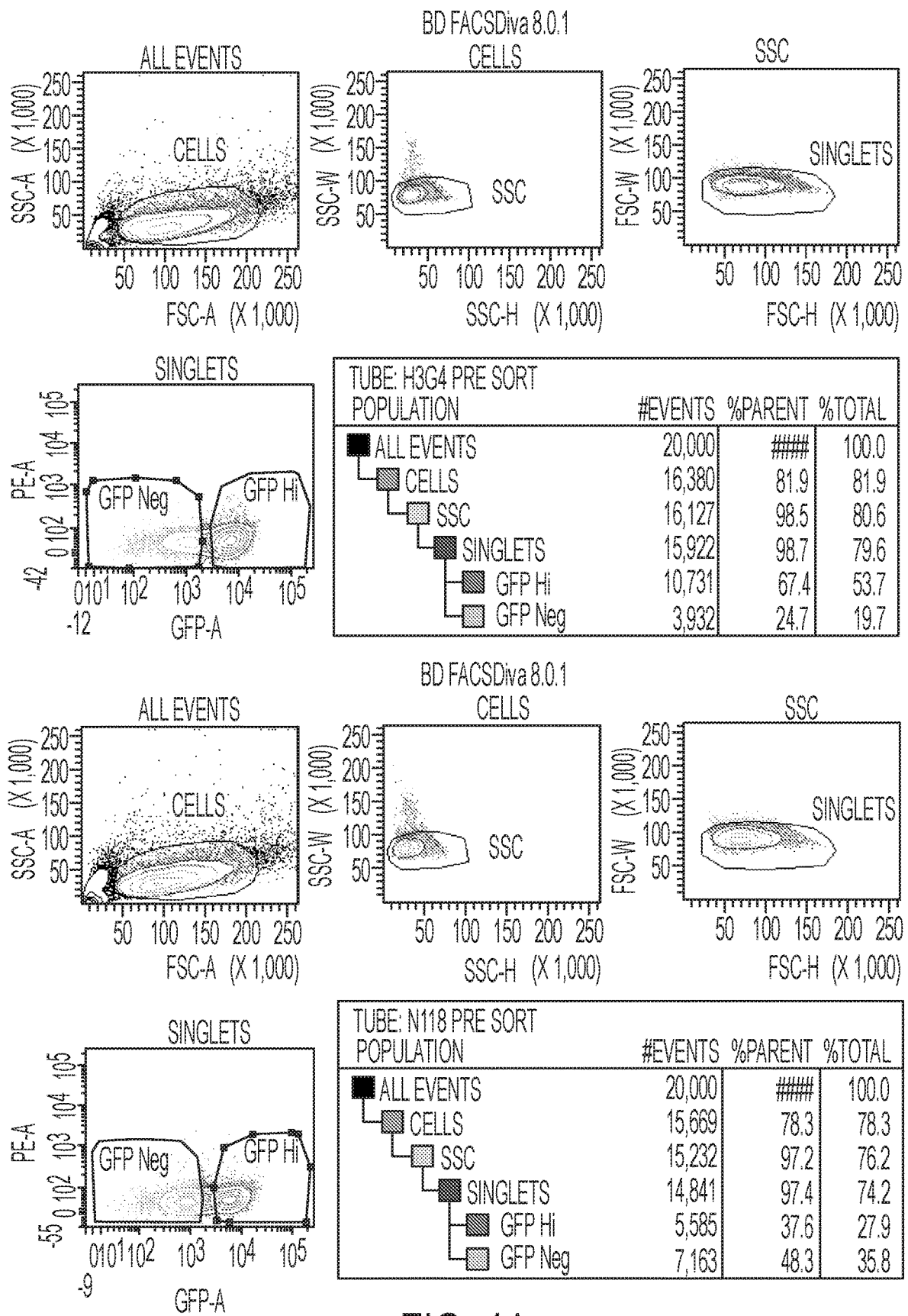
Figure 4C:
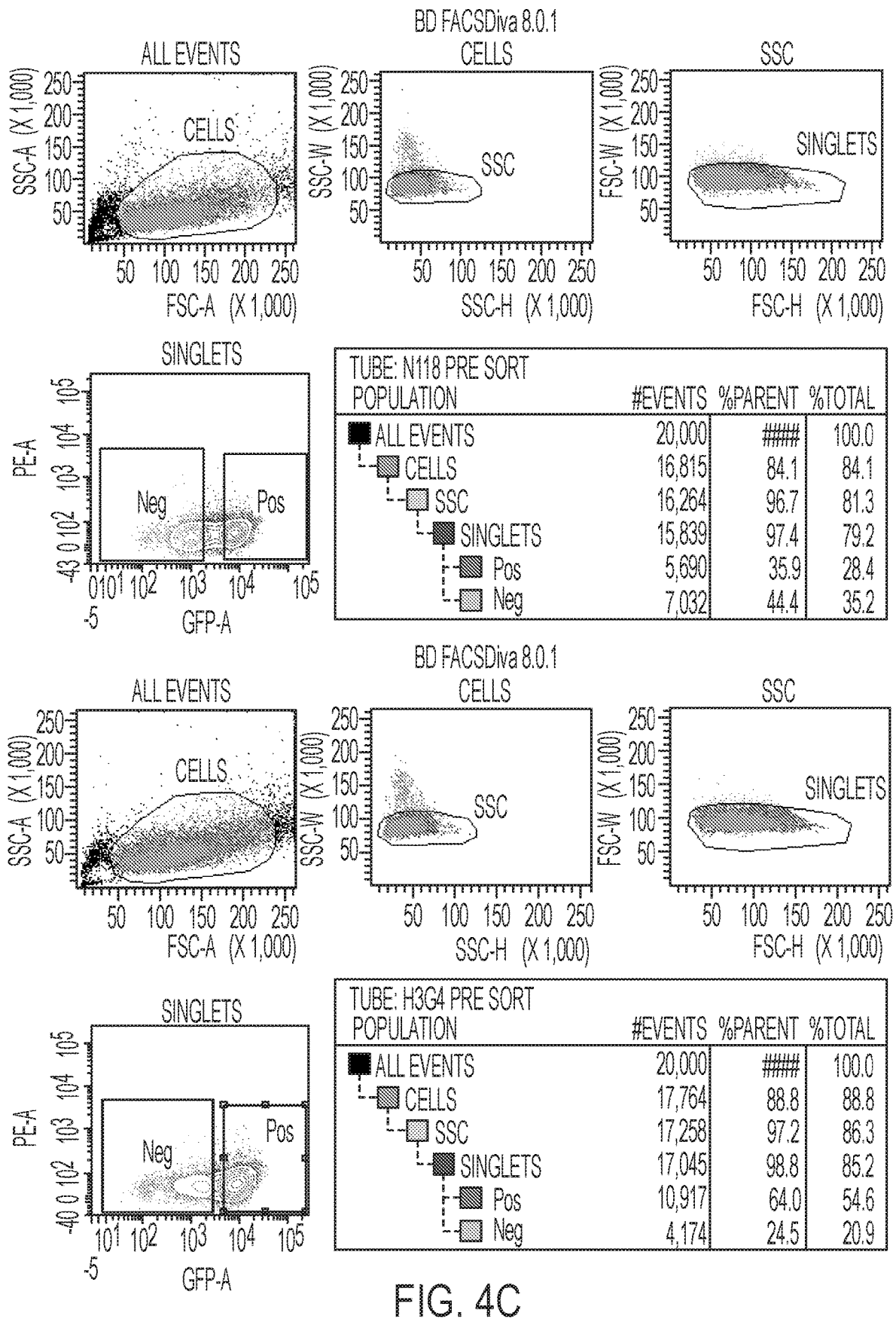

To demonstrate the stability and reversibility of CEM23 effects, CEM23-treated cells were sorted using fluorescence activated cell sorting (FACS) (FIGS. 4A-C). After 48-hours of 100 nM CEM23 treatment, the cells were separated into positive and negative populations. The GFP(−) was plated with or without continuous CEM23 exposure and maintained for evaluation. The negatively sorted cells were assessed with flow cytometry 3 days after FACS. The cells that were not treated with CEM23 regained almost full GFP expression (92.3% GFP+) and 71.8% of the CEM23 treated populated remained GFP(−) (FIG. 2E).

To investigate the ability of the bifunctional CEMs to be washed out and dosed back into the cells, a portion of the negatively sorted cells that were not given post-sort CEM-treatment and had regained GFP-expression were re-exposed. After 48-hours of reintroduction of 100 nM CEM23, 78% of the population repressed GFP (FIG. 2E). These results demonstrate the specificity and reversibility of this system to tune gene expression in a chemically-depend manner through endogenous HDAC recruitment. CEM42, featuring a longer linker region, behaved similarly to CEM23 in the Gal4-FKBP cells. At 100 nM, after 48 hours, CEM42 causing 41.1% of the cells to reside in the GFP(-) state, with no significant effects on transcription for the Gal4 control cells. (FIG. 3B) Knowing that recruitment of HDAC3 was likely to be responsible for gene repression, CEM36, based on a different chemotype reported to be selective for HDAC1/3 (Rai, M. et al. *PLoS One* 5, (2010),) was synthesized (FIG. 1B). CEM36 features a benzamide zinc chelating group that is known to have a very long residence time at the enzyme relative to the hydroxamic acid zinc chelating groups of CEM23 and CEM42, but is less potent. After treatment of FKBP-Gal4 cells with 100 nM CEM36 for 2 days, 17.0% of cells were GFP(-), with no effect in Gal4 control cells. (FIG. 3C).

FIG. 12 shows the median fluorescence value for each cell line and experimental consition.

Construct design. The plasmids expressing the Gal4-DBD control and FKBP-Gal4 were previously constructed and can be found on Addgene (44176 and 44245, respectively). HDAC3-Gal4 was constructed by stitching PCR. The HDAC3 was amplified from mESC cDNA and the Gal4 was amplified from Addgene #44176. Both pieces were stitched into a lentivirus backbone with EF1-α promoter driving HDAC3-Gal4 and a PGK promoter driving a resistance gene.

TABLE 1

Constructs.

| | | | |
|---|---|---|---|
| AC044_H3_F | HDAC3-Gal4 fusion | tgaggatccgc ggccgcgccac catggccaaga ccgtggcg | SEQ ID NO: 1 |
| AC045_H3_MF | HDAC3-Gal4 fusion | cgacaaggaaa gtgatgtggag attatgaagct actgtcttcta tcgaac | SEQ ID NO: 2 |
| AC046_H3_MR | HDAC3-Gal4 fusion | gttcgatagaa gacagtagctt cataatctcca catcactttcc ttgtcg | SEQ ID NO: 3 |
| AC047_H3_R | HDAC3-Gal4 fusion | agagccggcgc ggccgcctacg atacagtcaac tgtctttgacc | SEQ ID NO: 4 |

Example 3: Bifunctional CEM-Mediated Repression of eGFP Occurs in a Variegated and Whole-Colony Fashion mESCs are an adherent, colony-forming cell line, thus it was hypothesized that these characteristics were influencing the ability of cells to uptake the bifunctional CEMs and thereby limited the level of overall gene repression. To characterize the mode of the repression, fluorescent microscopy images of the HDAC3-Gal4 and bifunctional CEM-treated cell line were taken. In an unbiased, blinded manner ~200 mESC colonies for each line were counted and classified into three categories: GFP-Off, GFP-On, and GFP-Variegated. Colonies were labeled as "GFP Off" if all cells within the colony were off or expressing background-level GFP expression. Colonies in which all the observable cells were expressing GFP relatively brightly were categories as "GFP-On". "GFP-Variegated" colonies had cells within the colonies that maintained high GFP expression, in a mostly otherwise GFP(-) colony. Cell lines were grown and counted in duplicate, then averaged (FIG. 6).

Figure 5A:
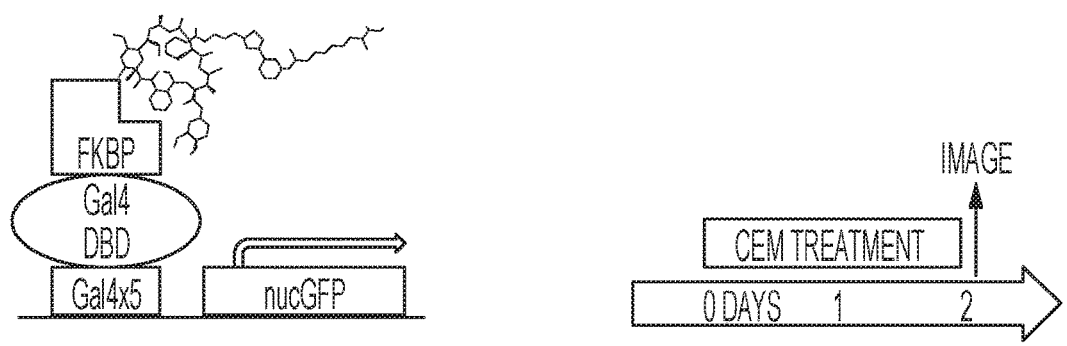
FIGS. 5A-C shows fluorescent microscopy images and colony categorization for CEM-treated cells.
Figure 5B:
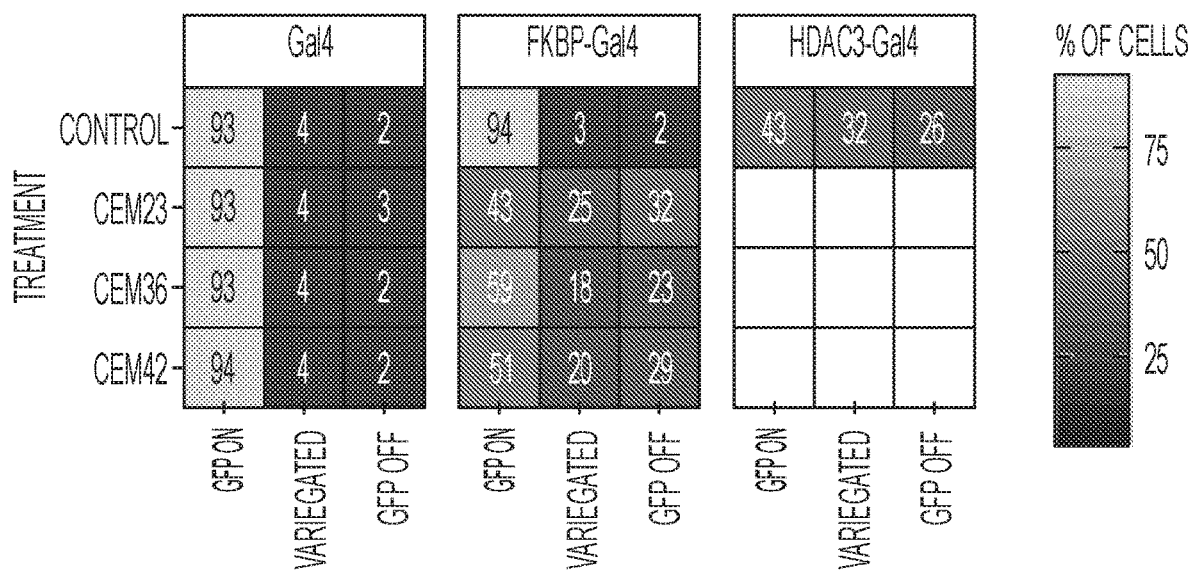
Figure 5C:
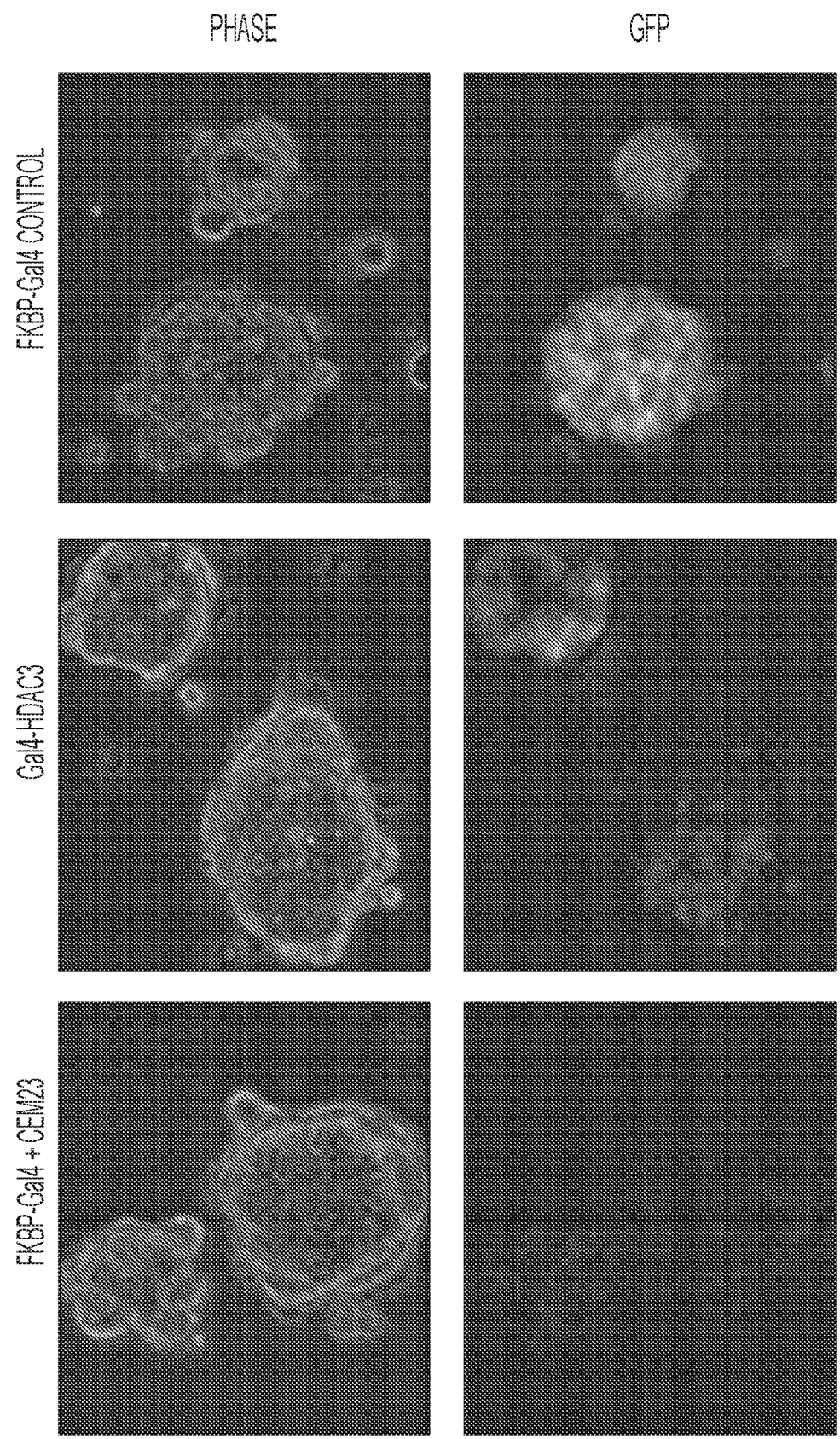

The Gal4-expressing and FKBP-Gal4 expressing cell lines were treated with 100 nM of CEM23, CEM36, or CEM42 for 48 hours. Images were taken throughout areas of the wells using a High Content Fluorescent Microscope (FIGS. 5A, B). HDAC3-Gal4 cell lines served as a positive control for HDAC3-recruitment. In the HDAC3-Gal4 cells, an average of 43% of cells was GFP-On, 25% were GFP Off and 32% were variegated. As expected, the GFP expression of the Gal4-infected colonies was not significantly affected by bifunctional CEM treatment. Of the FKBP-Gal4 cells treated with CEM23, 43% of the colonies were GFP-On, 32% were GFP-Off, and 25% were variegated, similar to the HDAC3-Gal4 cell line. The standard deviation between replicates was low when comparing the percentage of GFP-off colonies, whereas the percentages varied more between GFP-On and GFP-Variegated. This could be due to differences in what was determined to be fully on versus a variegated phenotype. Nevertheless, some colonies are remaining fully on or fully off, which does not support the hypothesis that bifunctional CEM-to-cell accessibility is limited by colony formation, resulting in an incomplete suppression of GFP expression. To validate cell morphology, representative images of the cell lines and treatment condition representative images are shown with a fluorescent microscope, which allowed phase microscopy of the colonies (FIG. 5C).

Flow cytometry and FACS. Flow cytometry analysis and fluorescence activated cell sorting were done with the University of North Carolina Flow Facility. The cells were washed, trypsinized, and plated into a 96 well format (at a density of about 2,000 cells/µL) for analysis in the Intellicyt iQue screener PLUS. UNC Flow Core Staff conducted the FACS with the FACS Aria II. $10^6$ cells were harvested for ChIP immediately after the sorted populations were acquired.

Image acquisition and quantification. The images taken for quantification were taken with the GE IN Cell Analyzer 2200 24 hours and 48 hours after compound exposure. Ten images, randomly dispersed throughout the well were taken per cell line. For each cell line condition, 147-213 colonies were counted and characterized as GFP On, GFP Off, or GFP Variegated. The percentage of each category was determined. This was done in duplicate with freshly infected and selected cell lines. Percentages for each category were averaged. The brightness/contrast of the brightfield images was uniformly adjusted in FIJI. Background artifact in the GPF-fluorescent images was uniformly removed in FIJI with a sliding paraboloid with a rolling ball radius of 10 pixels.

Confirmatory images were taken of the cells 24 and 48 hours after compound exposure with the Leica Olympus IX71. Phase images were not edited. Fluorescent images were edited in FIJI with a sliding parabolioid with a rolling ball radius of 20 pixels. 5 images were taken per replicate per condition, and representative images are shown.

Example 4: H3K27Ac Levels Decrease Upon Bifunctional CEM-Recruitment

Figure 7A:
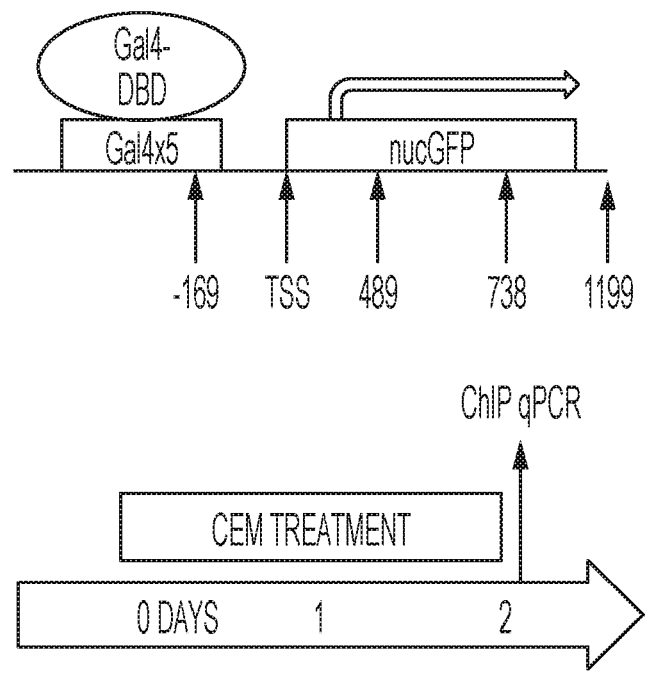
FIGS. 7A-D show H3K27Ac chromatin immunoprecipitation at the Cia:Oct4 locus. qPCR was performed at four sites at the nucGFP locus.

To examine the effects of bifunctional CEM-mediated HDAC recruitment on chromatin environment, ChIP-qPCR was performed. H3K27ac is a histone mark associated with active promoters and is regulated in part by HDAC3 activity (You, S.-H. et al. *Nat. Struct. Mol. Biol.* 20, 182-187 (2013)). Differences in H3K27ac at the Oct4 locus of the HDAC3-Gal4 cell line, the Gal4 cell line, and the FKBP-Gal4 cell line with and without 48 hours of 100 nM CEM23 exposure was tested (FIG. 7A). ChIP was performed using H3K27ac antibodies, and qPCR was done with primer pairs along the Oct4 locus (see, Table 2). H3K27ac enrichment levels were normalized to primers recognizing an intergenic region (IGR).

TABLE 2

Primer sequences used for qPCR in FIG. 7 and FIGS. 8A-C.

| Primer: | Forward: | Reverse: |
|---|---|---|
| −169 | CTAGAGGATCCGAGG ACCAATTG (SEQ ID NO: 5) | ACCTTCAAGGTCCTC TCACC (SEQ ID NO: 6) |
| 489 | CACATGAAGCAGCAC GACTT (SEQ ID NO: 7) | CCTTGAAGAAGATGG TGCGC (SEQ ID NO: 8) |
| 738 | CACATGGTCCTGCTG GAGTT (SEQ ID NO: 9) | ATCTAGAGTCGCGGC CGG (SEQ ID NO: 10) |
| 1199 | GTGATGGGTCAGCAG GGCT (SEQ ID NO: 11) | TCCGATTCCAGGCCC ACCT (SEQ ID NO: 12) |
| IGR | TTACTTCGTGTCTGT CGGGG (SEQ ID NO: 13) | GAGAGTAAAGTCAGA GAGGCCA (SEQ ID NO: 14) |

Figure 7B:
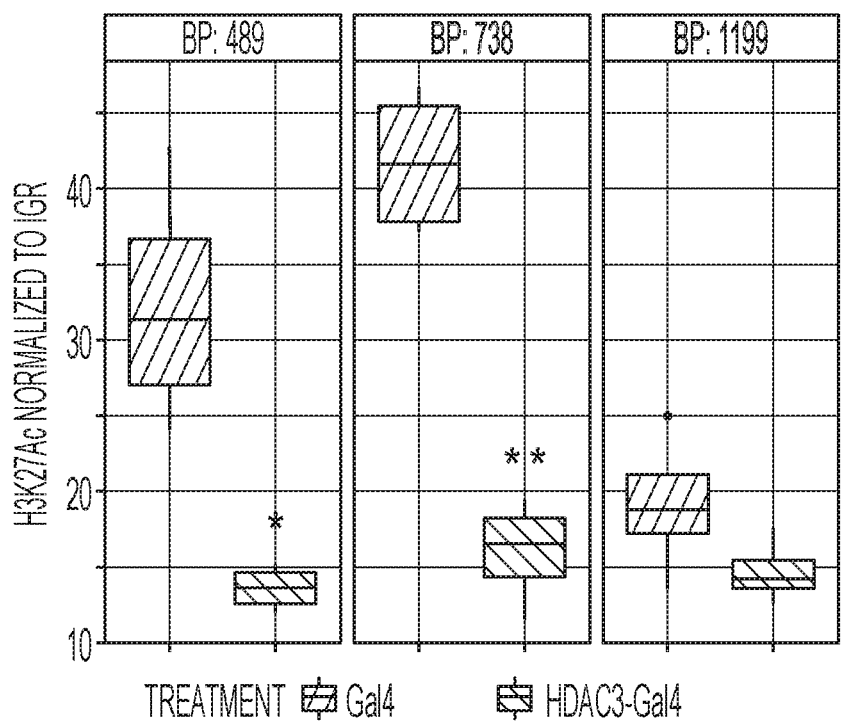
Figure 7C:
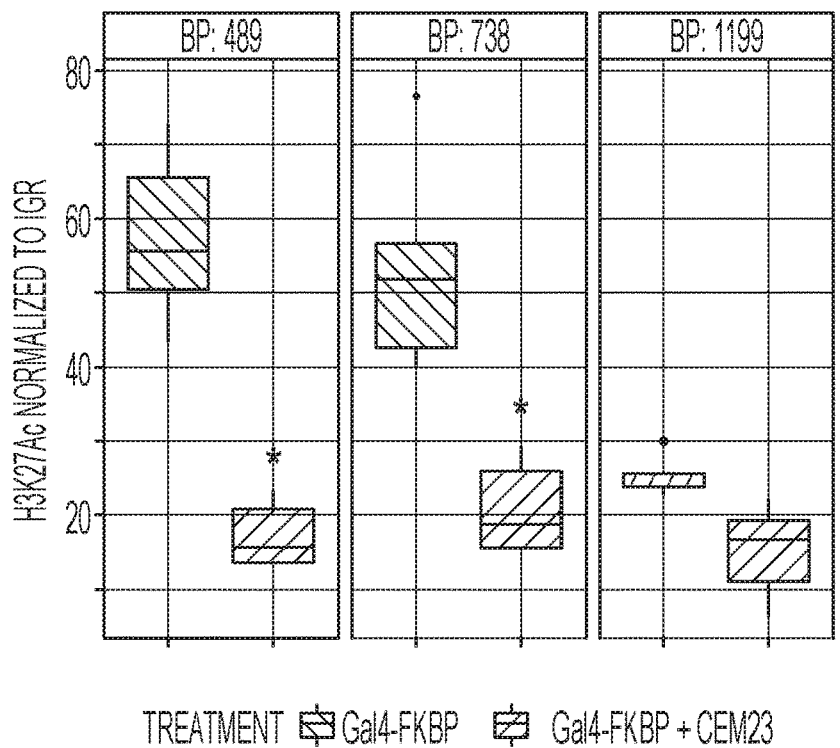
Figure 7D:
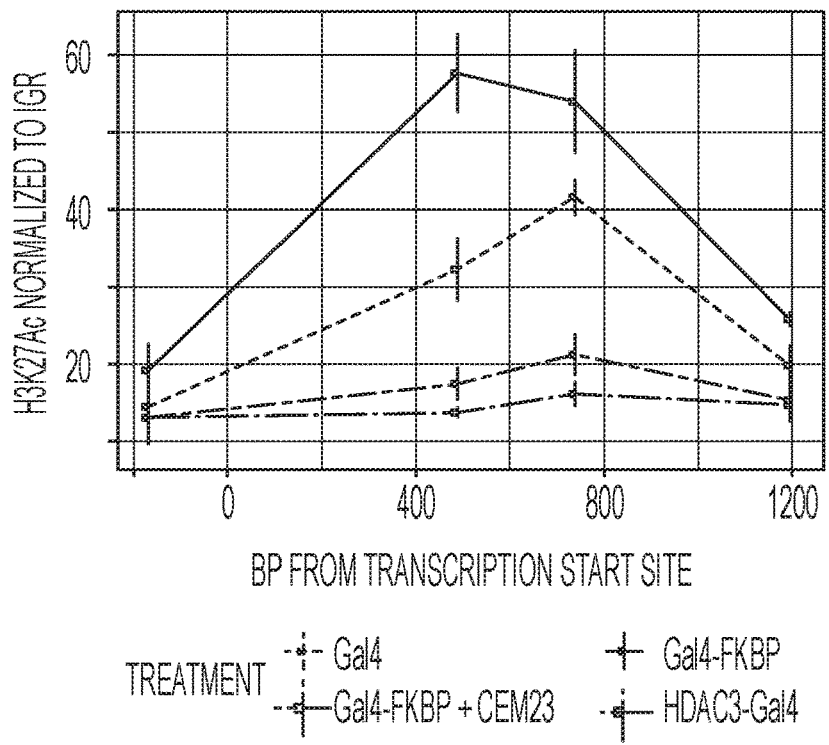
Figure 8A:
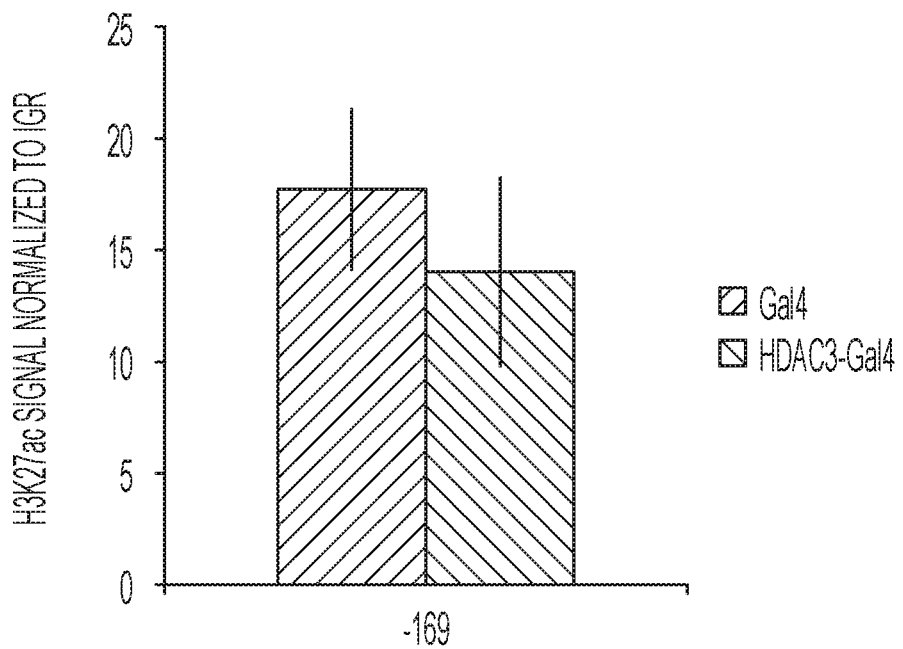
FIGS. 8A-C shows the results of quantitative RT-PCR comparing Gal4 to HDAC3-Gal4 cell lines (FIG. 8A) and Gal4-FKBP cells to Gal4-FKBP with 100 nM CEM23 (FIG. 8B) using an H3K27ac antibody and qPCR primers 169 basepairs upstream of the transcriptional start site. Quantitative RT-PCR compared Gal4-FKBP cells, Gal4-FKBP with 100 nM CEM23, and Gal4-FKBP with 100 nM CEM23 sorted into positive and negative populations, using an H3K27ac antibody and qPCR primers 738 basepairs downstream of the transcriptional start site (FIG. 8C).
Figure 8B:
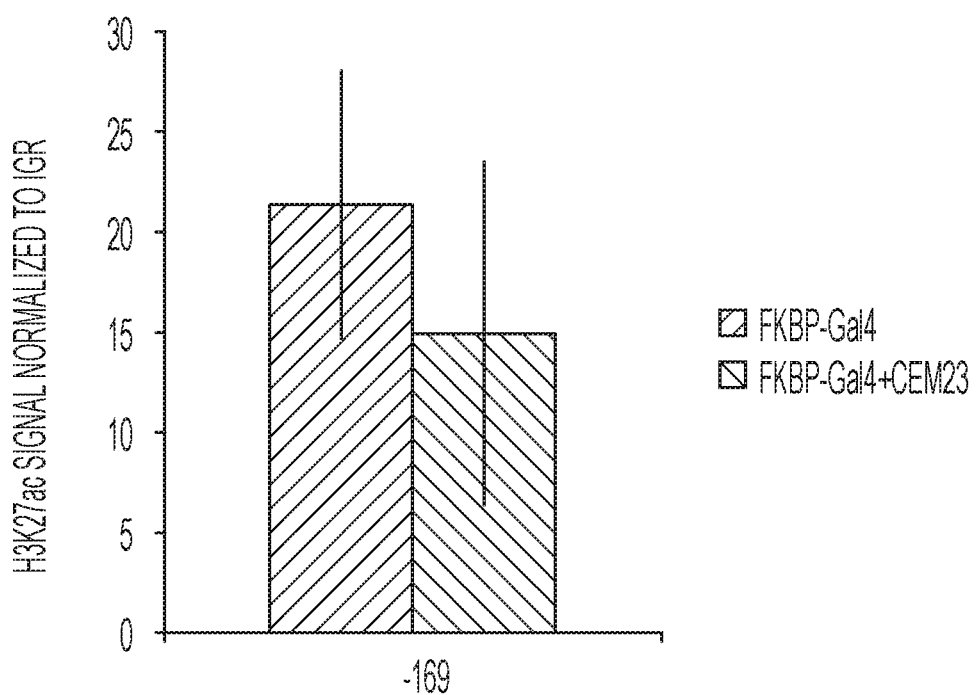

The normalized level of H3K27ac enrichment was significantly higher in the Gal4 cell line compared to the HDAC3-Gal4 cell line when tested at regions 489 base pairs (bp) and 738 bp downstream from the transcriptional start site (TSS) (*=p<0.05, n=4) (FIG. 7B). Next, H3K27ac levels at the same location in the FKBP-Gal4 cell lines with and without CEM23 treatment were tested. The results show that CEM23 decreased H3K27ac levels at 489, 738, and 1199 bp downstream of the TSS (FIG. 7C, *=p<0.05, **=p<0.005, n=5). The primer set at 169 bp upstream of the TSS did not show a significant change between the Gal4 cells and HDAC3-Gal4 cells, nor between the FKBP-Gal4+/−CEM23 cells (FIGS. 8A and 8B). This is not surprising, as regions this close to the TSS are typically largely devoid of nucleosomes. The results of H3K27ac levels in the four cell lines at −169, 489, 738, and 1199 bp from the TSS are summarized in FIG. 7D. These data support the hypothesis that bifunctional CEM-mediated gene repression occurs through endogenous HDAC recruitment.

Figure 8C:
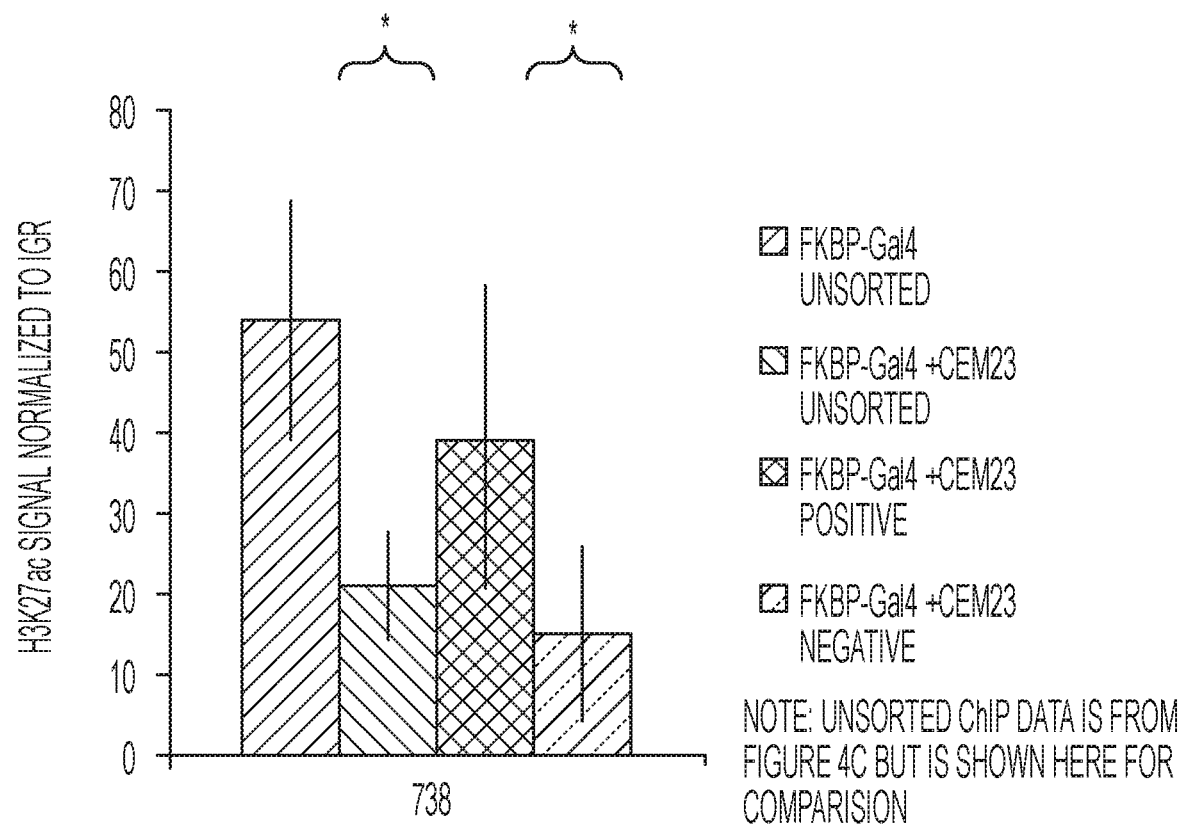

To confirm and further characterize the observed changes in histone tail acetylation, FKBP-Gal4 cells treated with 100 nM of CEM23 for 48 hours were separated into positive and negative populations by FACS. It was expected that the decreased acetylation levels observed in the CEM23-treated cells were contributed by the cells with decreased GFP expression (as observed by flow cytometry and microscopy). The H3K27ac levels in the GFP(+) and GFP(−) population from three separate sorting experiments were measured. The H3K27ac enrichment levels between the GFP(+) and GFP (−) populations were compared. As expected, H3K27ac levels in the GFP(+) population were significantly higher than the GFP-negative population. Additionally, H3K27ac levels in the untreated FKBP-Gal4 cells were not significantly different from the FKBP-Gal4+CEM23 positively sorted cells. And, H3K27ac levels in the FKBP-Gal4 CEM23-treated cells were not significantly different from the FKBP-Gal4+CEM23 negatively sorted cells (FIG. 8C).

It should be expected that the sorted GFP(+) population has acetylation levels similar to the unsorted FKBP-Gal4 control cells, and that the sorted GFP(−) population has acetylation levels similar to the unsorted FKBP-Gal4 CEM23 treated cells. These data show that within the CEM23-treated cells, the GFP(−) cells have lower H3K27ac levels than the GFP(+) cells. Bifunctional CEM compounds cause specific, targeted gene suppression by modifying the local chromatin. The mechanism of action for these compounds is direct recruitment of HDAC-containing corepressor complexes to the Gal4-FKBP transcription factor. Evidence supporting this claim is: the known ability of similar HDAC inhibitors to bind HDAC-containing corepressor complexes, Bantscheff, M. et al. *Nat. Biotechnol.* 29, 255-65 (2011) the reduction of transcription and H3K27 acetylation at the target gene, and the recapitulation of the drug-induced phenotype by a Gal4-HDAC3 fusion protein.

Suberanilohydroxamic acid (SAHA) derivatives like CEM23 and CEM46 are known to bind to multiple corepressor complexes, and have particularly high affinity towards CoREST, Sin3, and the HDAC3-containing nuclear receptor corepressor complex (NCOR) (Bantscheff, M. et al. *Nat. Biotechnol.* 29, 255-65 (2011); Zhang, J., Kalkum, M., Chait, B. T. & Roeder, R. G. *Mol. Cell* 9, 611-623 (2002)). DAC3 does not need to be catalytically active to cause gene repression in cells, and represses transcription independent of direct deacetylation, dependent on association with NCOR (Sun, Z. et al. *Mol. Cell* 52, 769-782 (2013)). Similarly, small molecule inhibition of HDAC3 does not upregulate HDAC3 target genes. So, when a bifunctional CEM recruits HDAC3/NCOR to a gene, HDAC3/NCOR can suppress transcription even while HDAC3's catalytic activity is blocked. HDAC3 is known to reside in the NCOR complex (Urvalek, A. M. & Gudas, L. J. J. Biol. Chem. 289, 19519-19530 (2014)), so it is unclear how deacetylation takes place while the NCOR HDAC3 enzyme is engaged by an inhibitor. It is hypothesized that a cloud of HDACs in the proximity of the gene are able to freely deacetylate.

Less selective, hydroxamic acid-containing HDAC inhibitors like CEM23 were most effective in the assays described herein. Slow dissociating benzamide compounds like CEM36 were not as effective, perhaps because these compounds have less affinity for the enzyme (Becher, I. et al. *ACS Chem. Biol.* 9, 1736-1746 (2014); (Wagner, F. F. et al. *Chem. Sci.* 6, 804-815 (2015)).

The bifunctional CEM compounds could be used in other cell lines that contain Gal4 binding arrays at a gene of interest, or could be adapted for use with other genetic engineering systems. dCas9-CRISPR is currently the most programmable system for epigenome editing.

ChIP-qPCR. For each sample, cells were trypsinized for 8-10 minutes, trypsin was quenched with 10 mL of ES media, and $10^6$ cells were obtained. Cells were spun down, washed with 10 mL PBS, fixed for 12 minutes in a mix of formaldehyde (to a final concentration of 1%) and Fix Buffer (50 mM HEPES pH 8.0, 1 mM EDTA, 0.5 mM EGTA, 100 mM NaCl), and then quenched by glycine (final concentration of 0.125M). Cells were incubated on ice, spun down at 1000×g for 5 minutes. Nuclei were prepared by consecutive washes with Rinse 1 Buffer (50 mM HEPES pH 8.0, 140 mM NaCl, 1 mM EDTA, 10% glycerol, 0.5% NP40, 0.25% Triton X100), Rinse 2 Buffer (10 mM Tris pH 8.0, 1 mM EDTA, 0.5 mM EGTA, 200 mM NaCl) and Shearing Buffer (0.1% SDS, 1 mM EDTA, 10 mM Tris HCl pH 8). After a final spin down, cells were resuspended in 100 μL Shearing Buffer and 1× protease inhibitor cocktail (Cabiochem), nanodroplets (generous gift from Samantha Pattenden (Kasoji, S. K. et al. *PLoS One* 10, (2015),) and sonicated in an E110 Covaris Sonicator for 4 minutes or until DNA was sheared to between 70-500 bp (as confirmed by agarose gel).

After sonication, the rest of the protocol was performed with a ChIP-IT High Sensitivity Kit (Active Motif, 53040) and an H3K27ac antibody was used for the pull down (Abcam, ab4729).

Example 5: Synthetic Methods for Bifunctional CEM Compounds

Chemistry general procedures. FK506 was purchased from Selleck. All other chemicals were purchased from Sigma-Aldrich or Fisher Scientific. HPLC spectra for all compounds were acquired using an Agilent 1200 Series system with DAD detector. Analytical HPLC chromatography was performed on a 2.1×150 mm Zorbax 300SB-C18 5 μm column with water containing 0.1% formic acid as solvent A and acetonitrile containing 0.1% formic acid as solvent B at a flow rate of 0.4 mL/min. The gradient program was as follows: 1% B (0-1 min), 1-99% B (1-4 min), and 99% B (4-8 min). High resolution mass spectra (HRMS) data were acquired in positive ion mode using an Agilent G1969A API-TOF with an electrospray ionization (ESI) source. Flash column chromatography was performed on a Teledyne ISCO CombiFlash Rf system equipped with a variable wavelength UV detector and a fraction collector using RediSep Rf normal phase silica columns. Microwave reactions were performed using a Discover SP CEM. Nuclear Magnetic Resonance (NMR) spectra were acquired on a Bruker DRX-600 spectrometer with 600 MHz for proton (1H NMR) and 150 MHz for carbon (13C NMR); chemical shifts are reported in ppm (δ). Preparative HPLC was performed on Agilent Prep 1200 series with UV detector set to 254 nm. Samples were injected onto a Phenomenex Luna 75×30 mm, 5 μm, C18 column at room temperature. The flow rate was 30 mL/min. A linear gradient was used with 10% (or 50%) of MeOH (A) in H2O (with 0.1% TFA) (B) to 100% of MeOH (A). HPLC was used to establish the purity of target compounds. All final compounds had >95% purity using the HPLC methods described herein.

Figure 13:
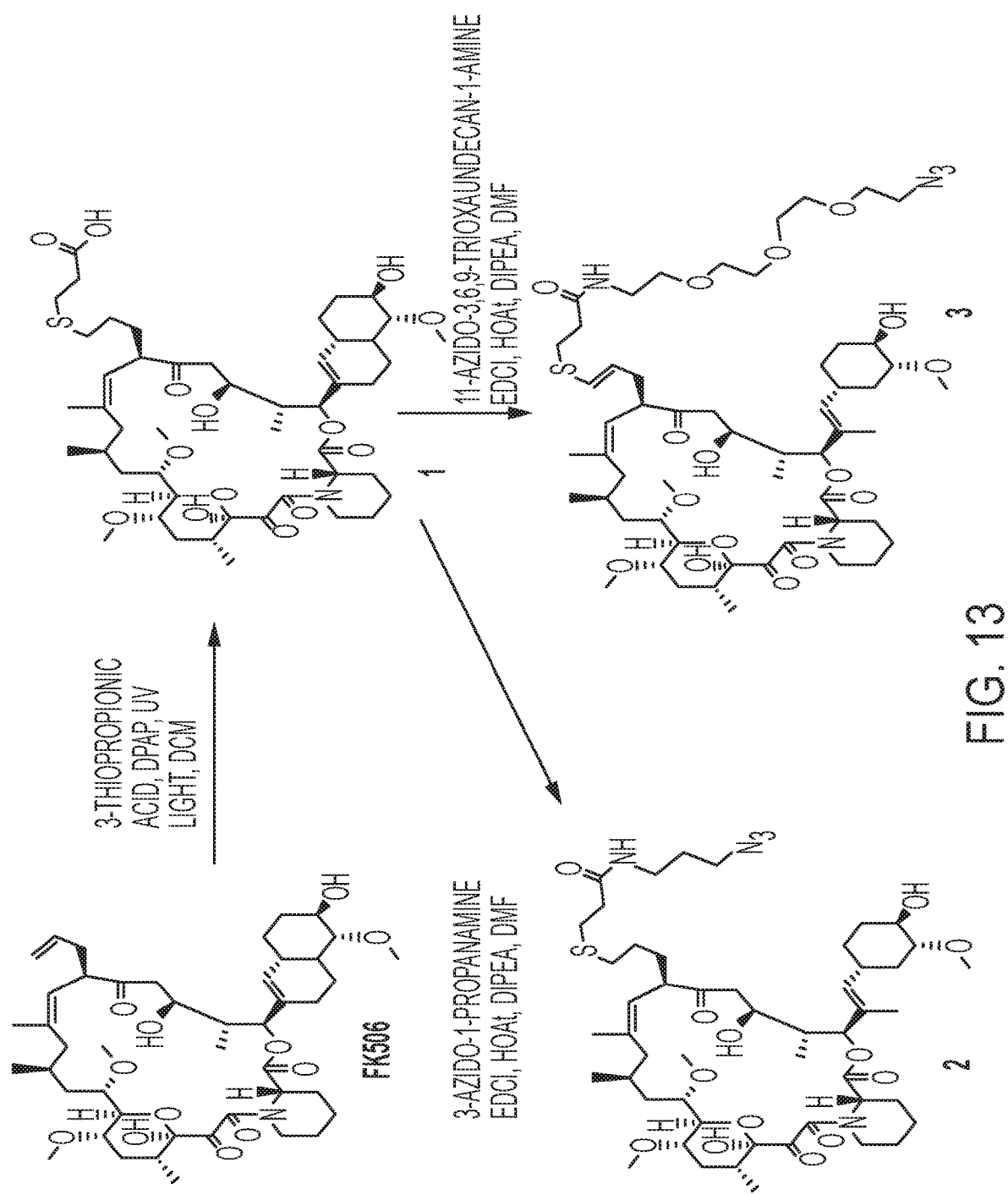
FIG. 13 shows the synthesis of compounds 1-3.

FIG. 13 shows the synthesis of compounds 1-3. (2) FK506-mercaptopropanamide propylazide: FK506-mercaptopropionic acid (Compound 1) was prepared as described.[1] Compound 1 (182 mg, 0.2 mmol) in DMF (1 ml) was treated sequentially with EDCI-HCl (25 mg, 0.25 mmol), HOAT (41 mg, 0.3 mmol), 3-Azido-1-propanamine (25 mg, 0.25 mmol), and DIPEA (70 μl, 0.4 mmol). This was stirred for 24 h and purified by HPLC. Yield: 82 mg, 41%. TOF-HRMS (m/z) found (calcd.) for $[C_{50}H_{81}N_5O_{13}S+H]^+$: 992.5634 (992.5630). $^1$H NMR (600 MHz, Chloroform-d) δ 6.09 (s, 1H), 5.37 (s, 1H), 5.14-4.95 (m, 2H), 4.63 (m, 1H), 4.44 (d, J=13.7 Hz, 1H), 3.94 (d, J=10.3 Hz, 1H), 3.70 (d, J=9.6 Hz, 1H), 3.65-3.54 (m, 1H), 3.46-3.25 (m, 17H), 3.07-2.97 (m, 2H), 2.86-2.73 (m, 3H), 2.54 (dt, J=12.5, 7.0 Hz, 3H), 2.49-2.22 (m, 7H), 2.22-1.85 (m, 11H), 1.85-1.74 (m, 6H), 1.74-1.23 (m, 20H), 1.16-0.81 (m, 13H). (3) Compound 1 (200 mg, 0.27 mmol), 11-Azido-3,6,9-trioxaundecan-1-amine (51 μl, 0.26 mmol), EDCI-HCl (53 mg, 0.28 mmol), DIPEA (0.094 ml, 0.54 mmol), and HOAT (51 mg, 0.33 mmol) were stirred in 2 ml DCM for 24 h. The product was purified by HPLC. Yield: 143 mg, 48%. TOF-HRMS (m/z) found (calcd.) for $[C_{55}H_{91}N_5O_{16}S+H]^+$: 1110.6260 (1110.6260). $^1$H NMR (600 MHz, Chloroform-d) δ 6.43 (d, J=15.8 Hz, 1H), 5.36 (s, 1H), 5.26-4.91 (m, 3H), 4.61 (s, 1H), 4.44 (d, J=13.8 Hz, 1H), 4.04-3.84 (m, 1H), 3.71-3.57 (m, 12H), 3.48-3.29 (m, 14H), 3.02 (d, J=11.7 Hz, 2H), 2.81 (t, J=7.3 Hz, 2H), 2.75 (d, J=15.9 Hz, 1H), 2.54 (s, 2H), 2.47 (t, J=7.4 Hz, 2H), 2.31 (s, 2H), 2.19-1.26 (m, 47H), 1.11-0.82 (m, 13H).

Figure 14:
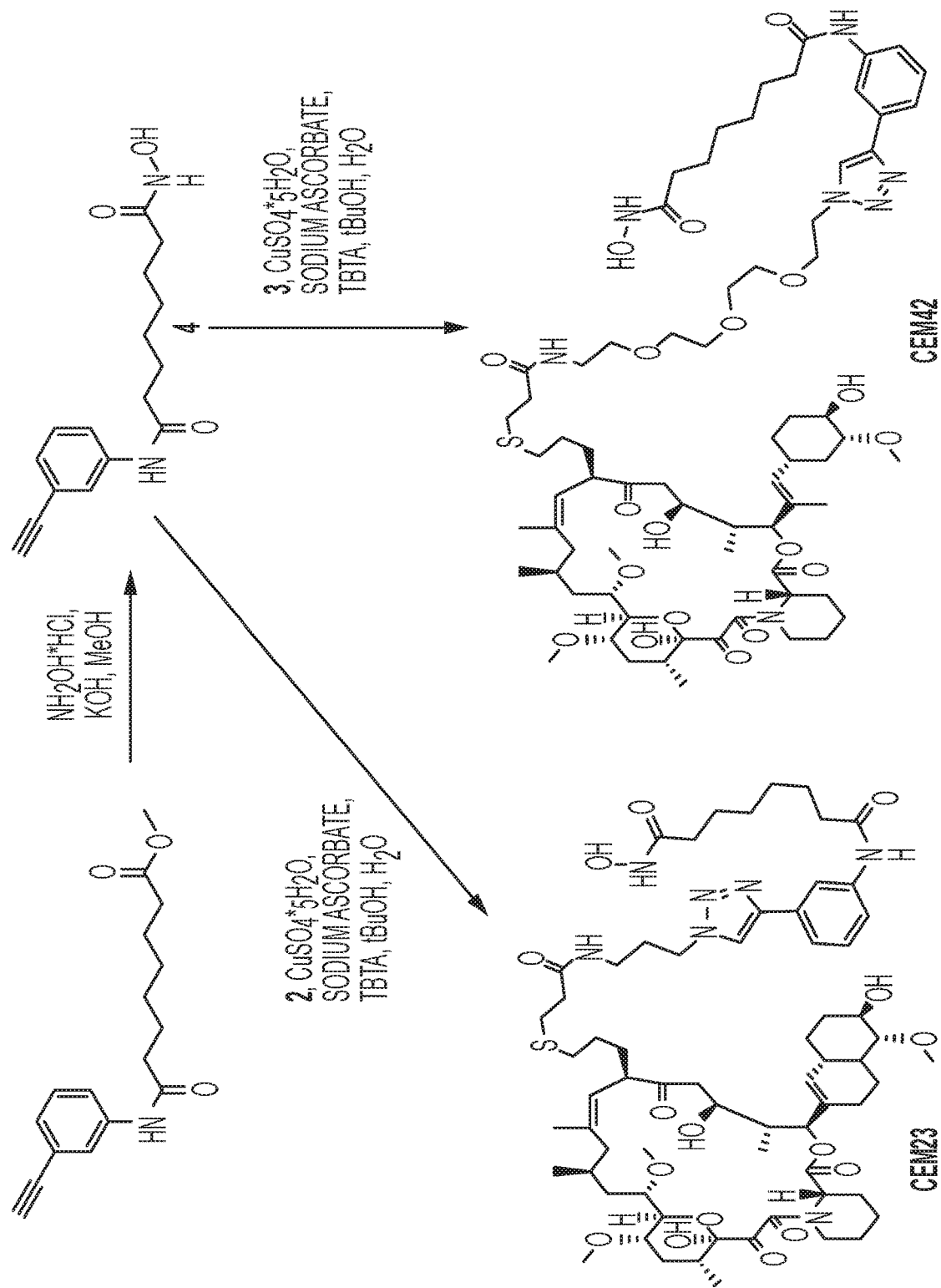
FIG. 14 shows the synthesis of compound 4, and bifunctional CEMS (e.g., CEM23 and CEM42).

FIG. 14 shows the synthesis of compound 4, and bifunctional CEMS (e.g., CEM23 and CEM42). (4) N1-(3-Ethynylphenyl)-N8-hydroxyoctanediamide: Methyl 8-((3-ethynylphenyl)amino)-8-oxooctanoate2 (250 mg, 0.87 mmol) was dissolved in 3 ml of MeOH and 3 ml of THF, then treated with KOH (97 mg, 1.74 mmol, dissolved in a minimal amount of water) and NH2OH (50% aqueous solution, 0.57 ml, 8.7 mmol), and stirred 24 h. The reaction was neutralized with 1M HCl and the product was extracted with DCM. Purification by HPLC gave the product Yield: 43 mg, 17%. TOF-HRMS (m/z) found (calcd.) for $[C_{16}H_{20}N_2O_3+H]^+$: 289.1655 (289.1552). $^1$H NMR (600 MHz, DMSO-d6) δ 10.34 (s, 1H), 9.98 (s, 1H), 8.67 (s, 1H), 7.79 (s, 1H), 7.55 (d, J=8.2 Hz, 1H), 7.30 (t, J=7.9 Hz, 1H), 7.13 (d, J=7.6 Hz, 1H), 4.17 (s, 1H), 2.29 (t, J=7.5 Hz, 2H), 1.94 (t, J=7.4 Hz, 2H), 1.57 (t, J=7.4 Hz, 2H), 1.52-1.45 (m, 2H), 1.27 (s, 4H). 13C NMR (151 MHz, DMSO-d6) δ 171.93, 169.49, 139.92, 129.56, 126.58, 122.34, 122.20, 119.97, 83.84, 80.89, 40.44, 36.78, 32.64, 28.80, 25.43, 25.33.

Figure 16:
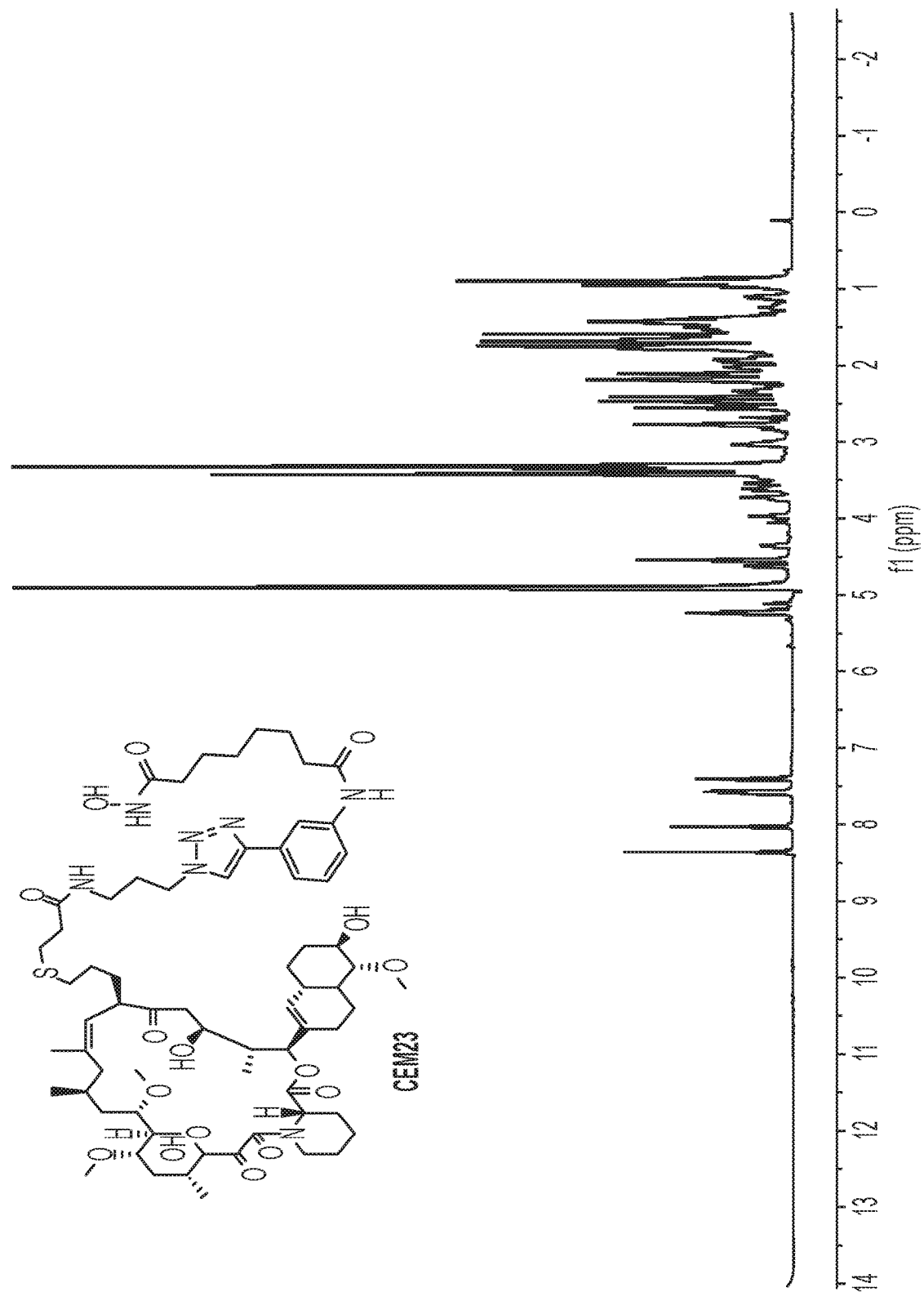
FIG. 16 shows the $^1$NMR spectra of CEM23.
Figure 17:
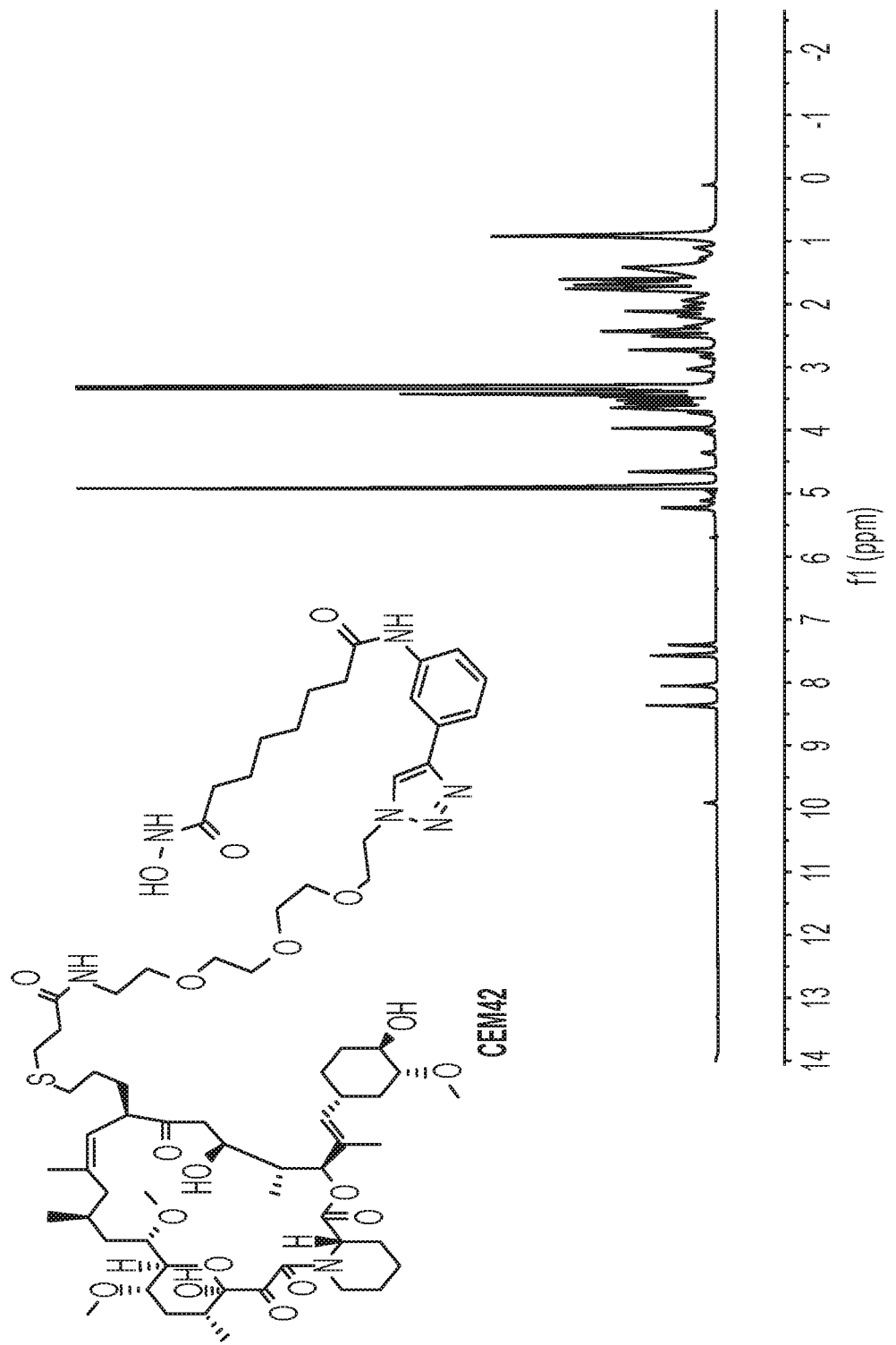
FIG. 17 shows the $^1$NMR spectra of CEM42.

General procedure for click reactions with FK506-azides: The azide (1 equiv, 0.02 mmol) and the alkyne (1 equiv) were dissolved in 1 ml tBuOH. This was treated sequentially with TBTA (2 mg), copper sulfate pentahydrate (0.05 equiv of a 0.1M solution in water), and sodium ascorbate (0.2 equiv of a 0.1M solution in water). The reaction was stirred for 24 h then purified by HPLC. CEM23: The product was prepared from 10 and 3 by the general procedure for click reactions. Yield: 13 mg, 56%. TOF-HRMS (m/z) found (calcd.) for $[C_{66}H_{101}N_7O_{16}S+H]^+$: 1280.7011 (1280.7104). $^1$H NMR (600 MHz, Methanol-d4) δ 8.36 (s, 1H), 8.03 (s, 1H), 7.58 (dd, J=16.2, 7.9 Hz, 2H), 7.40 (t, J=7.9 Hz, 1H), 5.29-5.09 (m, 2H), 4.54 (m, 2H), 4.36 (d, J=13.5 Hz, 1H), 3.97 (m, 1H), 3.79-3.68 (m, 1H), 3.63 (m, 3H), 3.50-3.39 (m, 6H), 3.36 (m, 3H), 3.02 (m, 2H), 2.89-2.65 (m, 4H), 2.55 (m, 2H), 2.52-2.25 (m, 7H), 2.25-1.98 (m, 10H), 1.94 (m, 3H), 1.88-1.71 (m, 9H), 1.71-1.18 (m, 23H), 1.18-1.06 (m, 1H), 1.06-0.80 (m, 10H). HPLC Purity: >95%, tR=4.78 min. CEM42: The product was prepared from 4 and 3 by the general procedure for click reactions. Yield: 13 mg, 56%. TOF-HRMS (m/z) found (calcd.) for $[C_{71}H_{111}N_7O_{19}S+H]^+$: 1398.7731 (1398.7734). $^1$H NMR (600 MHz, Methanol-d4) δ 8.37 (s, 1H), 8.06 (s, 1H), 7.57 (d, J=7.8 Hz, 2H), 7.41 (t, J=7.9 Hz, 1H), 5.27-5.19 (m, 2H), 4.69-4.61 (m, 2H), 3.97 (t, J=5.0 Hz, 2H), 3.78-3.71 (m, 1H), 3.69-3.51 (m, 9H), 3.49-3.39 (m, 7H), 3.39-3.34 (m, overlaps with solvent), 3.04 (s, 1H), 2.73 (t, J=7.2 Hz, 2H), 2.55-2.25 (m, 9H), 2.23-1.86 (m, 10H), 1.82-1.03 (m, 31H), 1.02-0.80 (m, 10H). HPLC Purity: >95%, tR=5.08 min. FIG. 16 shows the $^1$NMR spectra of CEM23. FIG. 17 shows the $^1$NMR spectra of CEM42.

Figure 15:
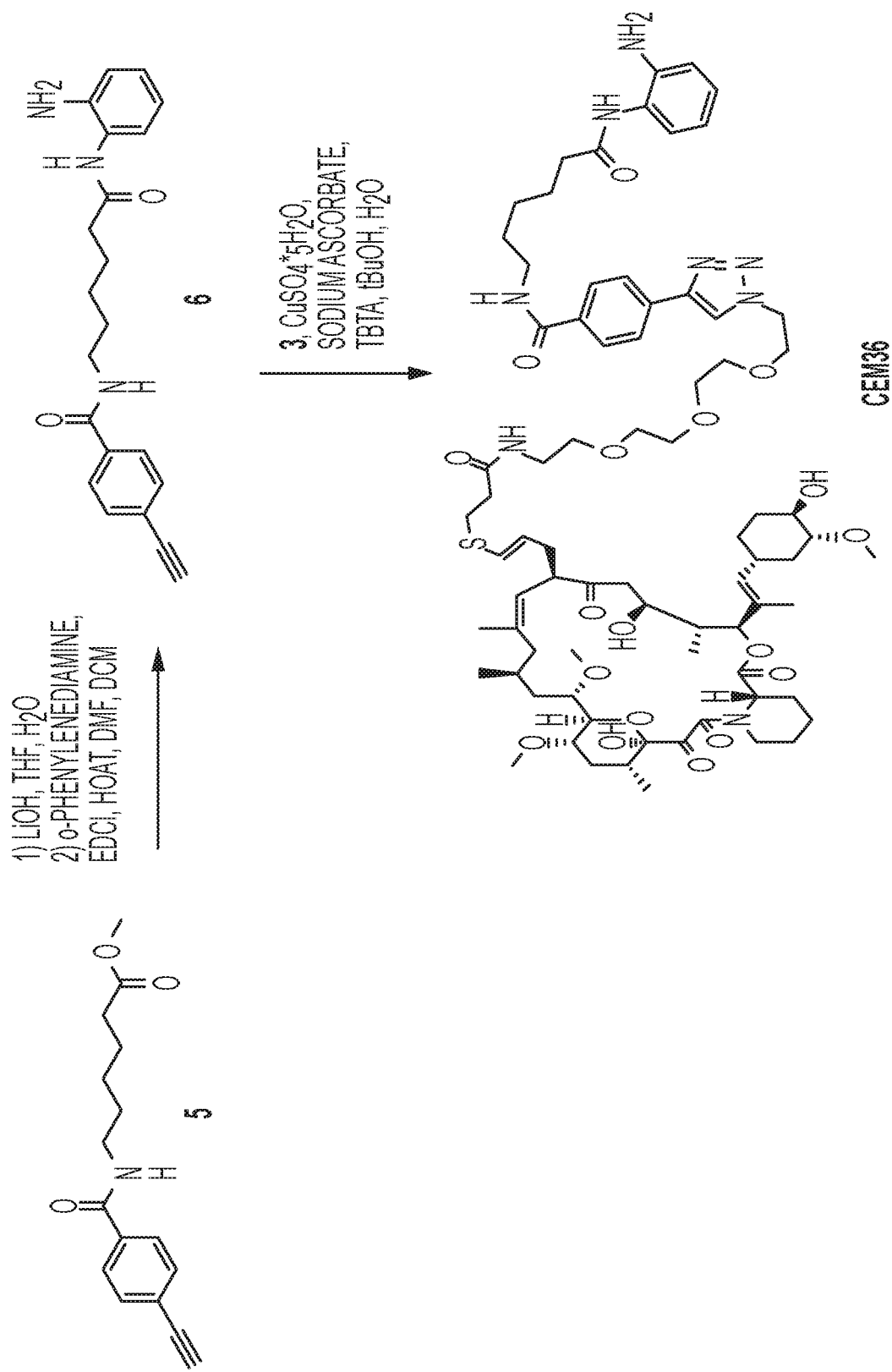
FIG. 15 shows the synthesis of compounds 5 and 6, and bifunctional CEM36.
Figure 18:
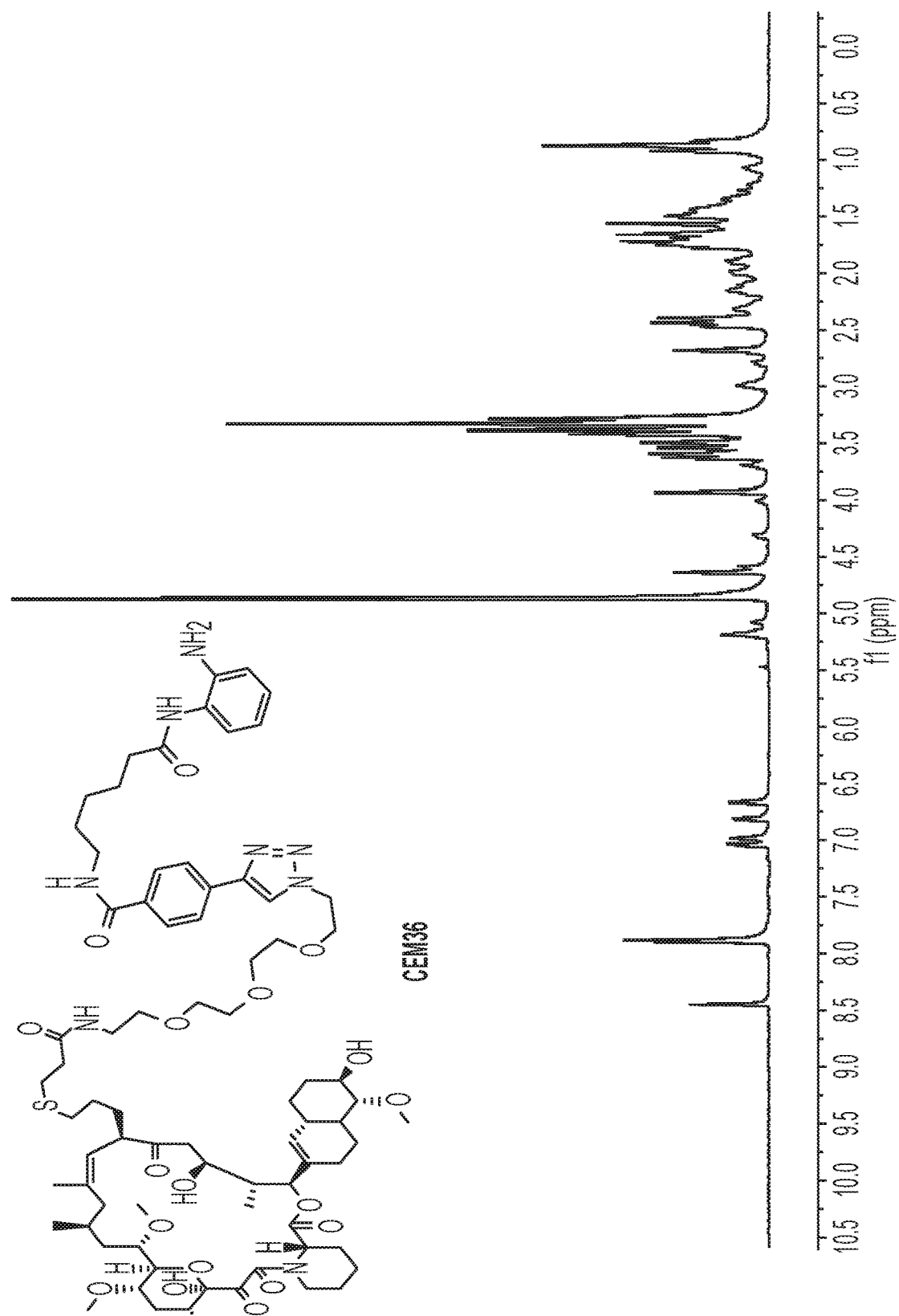
FIG. 18 shows the $^1$NMR spectra of CEM36.

FIG. 15 shows the synthesis of compounds 5 and 6, and bifunctional CEM36. (5) Methyl 6-(4-ethynylbenzamido)hexanoate: 4-Ethynylbenzoic acid (500 mg, 3.42 mmol), methyl 6-aminohexanoate HCl salt (743 mg, 4.11 mmol), EDCI-HCl (795 mg, 5.13 mmol), HOAT (697 mg, 5.13 mmol), and DIPEA (1.49 ml, 8.55 mmol) were stirred in 12 ml of a 1:3 mixture of DMF: DCM. Aqueous workup followed by silica gel purification (20 to 100% gradient of EtOAc in hexane) gave the product. Yield: 487 mg, 52%. TOF-HRMS (m/z) found (calcd.) for $[C_{16}H_{19}NO_3+H]^+$: 274.2439 (274.1443). $^1$H NMR (600 MHz, Chloroform-d) S 7.75 (d, J=8.0 Hz, 2H), 7.57 (d, J=8.0 Hz, 2H), 6.24 (s, 1H), 3.69 (s, 3H), 3.49 (q, J=6.7 Hz, 2H), 3.21 (s, 1H), 2.36 (t, J=7.3 Hz, 2H), 1.71-1.65 (m, 4H), 1.44 (t, J=7.8 Hz, 2H). (6)N-(6-((2-Aminophenyl)amino)-6-oxohexyl)-4-ethynylbenzamide: Compound 4 (340 mg, 1.25 mmol) was dissolved in THF (20 ml). To this was added aqueous LiOH (355 mg LiOH dissolved in 20 ml H2O), and the mixture was stirred 24 h. The mixture was acidified with 2N HCl and the product was extracted with EtOAc. The EtOAc extracts were concentrated to give 6-(4-ethynylbenzamido)hexanoic acid. Yield: 93%, 301 mg. TOF-HRMS (m/z) found (calcd.) for $C_{15}H_{17}NO_3$ (M): [M+H]+, 260.1286 (260.1287). 6-(4-ethynylbenzamido)hexanoic acid (100 mg, 0.38 mmol), o-phenylenediamine (206 mg, 1.90 mmol), EDCI (66 mg, 0.42 mmol), and HOAT (58 mg, 0.42 mmol) were stirred in 8 ml of a 1:3 mixture of DMF:DCM for 24 h. The reaction was taken up in sat. aq. NaHCO$_3$ and the product was extracted with EtOAc. The product was purified by silica gel chromatography (eluting first with a gradient of 50 to 100% EtOAc in hexane, followed by 0 to 20% MeOH in DCM). Yield: 50 mg, 38% for final step. TOF-HRMS (m/z) found (calcd.) for $[C_{21}H_{23}N_3O_2+H]^+$: 350.1954 (350.1869). $^1$H NMR (600 MHz, Chloroform-d) δ 7.74 (d, J=8.4, 2H), 7.47 (m, 2H), 7.21 (d, 1H), 7.04 (q, J=8.0 Hz, 1H), 6.88-6.77 (m, 2H), 3.50-3.44 (m, 2H), 3.20 (s, 1H), 2.45 (t, J=7.1 Hz, 2H), 1.78 (p, J=7.2 Hz, 2H), 1.66 (m, 2H), 1.48 (m, J=7.8 Hz, 2H). $^{13}$C NMR (151 MHz, DMSO-d6) δ 171.49, 165.64, 142.31, 135.15, 132.01, 127.84, 126.10, 125.71, 124.62, 123.94, 116.55, 116.27, 83.33, 83.13, 40.45, 36.12, 29.30, 26.59, 25.49. CEM36: The product was prepared from 2 and 5 by the general procedure for click reactions, except that the product was purified by silica gel chromatography (gradient of 0 to 20% MeOH in DCM) rather than by HPLC. Exposure to acid used in HPLC buffer causes the product to decompose. Yield: 41 mg, 78%. TOF-HRMS (m/z) found (calcd.) for $[C_{76}H_{114}N_8O_{18}S+H]^+$: 1459.8060 (1459.8050). HPLC Purity: >95%, tR=4.88 min. $^1$H NMR (600 MHz, Methanol-d4) δ 8.51-8.46 (m, 1H), 7.93 (q, J=8.0 Hz, 4H), 7.11-7.06 (m, 1H), 7.05-7.00 (m, 1H), 6.85 (s, 1H), 6.73-6.67 (m, 1H), 5.22 (s, 2H), 4.65 (dd, J=26.9, 5.5 Hz, 3H), 4.36 (d, J=13.7 Hz, 1H), 4.00-3.94 (m, 3H), 3.68-3.50 (m, 13H), 3.48-3.28 (m, 30H, integration overlaps with Methanol-d4), 3.02 (d, J=17.0 Hz, 2H), 2.72 (t, J=7.2 Hz, 3H), 2.47 (ddd, J=28.7, 14.1, 6.8 Hz, 7H), 2.41-1.89 (m, 13H), 1.82-1.37 (m, 31H), 0.98-0.85 (m, 11H). FIG. 18 shows the $^1$NMR spectra of CEM36.

Example 6: Design and Validation of New Molecular and Chemical Tools for Specific Allele Regulation These experiments will improve the dCas9-based gene repression method. Three areas will be improved: protein engineering of dCas9-FKBP constructs, medicinal chemistry techniques to improve bifunctional CEM recruitment of epigenetic enzymes, and exploration of the best region of the promoter to target with sgRNA using model system reporters.

Figure 9B:
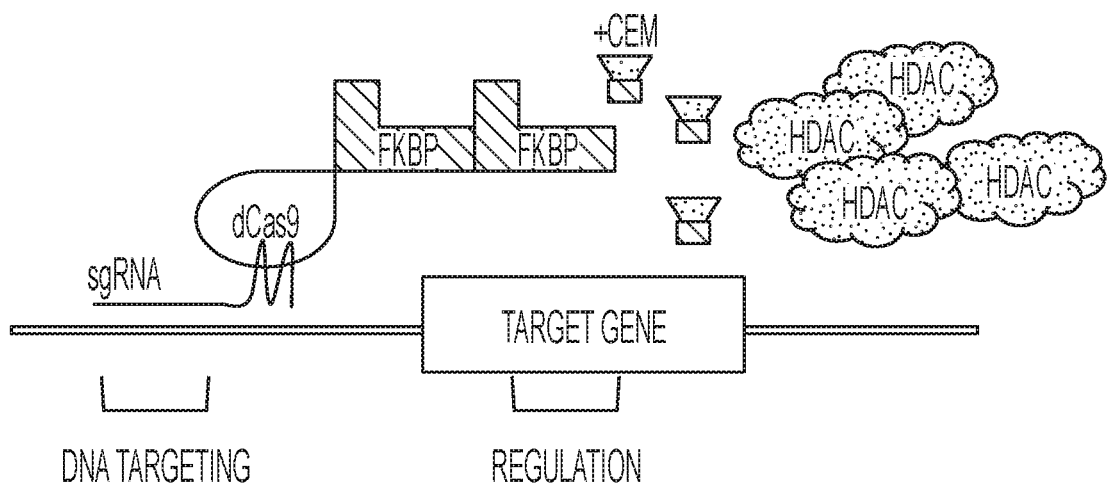

Development of dCas9 based epigenetic regulators. The development and validation of the first generation of the dCas9-FKBP recruitment tool will be carried out. With this approach, the dCas9-FKBP will be used to recruit via CIP-rapamycin, which recruits desired effector proteins by CIP addition causing gene repression (Hathaway, N. A. et al. Cell 149, 1447-1460 (2012)). The original dCas9-FKBP can be used to recruit bi-functional CEMs (FIG. 9) to direct endogenous epigenetic repression machinery such as HDAC enzymes to any desired loci causing gene repression. Protein engineering will be used to increase the density of HDAC protein recruitment to the target promoter by adapting two effective techniques to work with the FKBP based recruitment system. The first is an inclusion of RNA structural element, called a MS2 hairpin, into the sgRNA, which would then be bound by a fusion protein between an FKBP and a MCP element (which binds the MS2 hairpin and has been used by others with a dCas9 to recruit both gene repressors (Mali, P. et al. Nat. Biotechnol. 31, 833-838 (2013); (Zalatan, J. G. et al. Cell 160, 339-350 (2014)). This strategy will allow the FKBP concentration at the target site to be tripled and increase the HDAC activity recruited by this method. A second approach to increasing HDAC density will be making SunTag variants of dCas9 to string a series of FKBP proteins. These function by making a long string of peptides that can be recognized by a small antibody fragment fused to the desired recruitment protein (e.g., FKBP). This strategy can recruit up to 24 protein fusions from a single string (Tanenbaum, M. E., Gilbert, L. A., Qi, L. S., Weissman, J. S. & Vale, R. D. Cell 159, 635-646 (2014); (Chavez, A. et al. Nat. Methods 13, 563-567 (2016)). Next, strategies to increase FKBP density at the target site will be performed. This will yield more rapid and complete gene repression by either CIP or CEM technologies. All dCas9 epigenetic regulation systems will be evaluated using a mouse ES cell assay systems.

Development of bifunctional chemical epigenetic modulators. Another important component of the platform described herein is the effective chemical engagement of endogenous chromatin modifying enzymes with the bifunctional CEM strategy. While CEM23 effectively engages HDAC activity and markedly reduces gene expression (see, FIG. 10), there are many medicinal chemistry strategies that will be improved. To date, over a dozen different epigenetic inhibitors have been and can be attached to the bifunctional FK506 and the ability of each compound either to enhance or suppress transcriptional activity in a mouse ES cell reporter evaluated. Two areas for improvement include linker chemistry and inhibitor class. A moderately short polyethylene glycol (PEG) can be used and has been demonstrated to be superior compared to a longer linker. Medicinal chemistry analysis for the optimal linking group for each bifunctional CEM generation will be performed, as different binding modes will likely require different linking group properties. Next, other epigenetic inhibitors will be examined to recruit chromatin modifying enzymes. Other studies will focus on linking to chemical probes that bind chromobox-containing proteins that will recruit either HP1, polycomb, or other chromatin regulatory proteins. It is expected that some compounds will be more effective than HDAC recruitment in the current generation of bifunctional CEMs. The ES cell assay systems and models will be used as a benchmark for successful design of next generation bifunctional CEMs.

Application of dCas9 based bifunctional CEMs in mouse embryonic stem cells. Experiments will be performed to improve bifunctional CEMs in CiA ES cells. This approach has the advantage of being rapid, capable of being visualized in real-time due to the GFP reporter, and quantitative. The tethering of GAL4-FKBP (via the inserted GAL4 array in the promoter) will be compared to dCas9-FKBP at the Oct4 promoter and reporter gene. These experiments will be used to identify the best region of the promoter to target sgRNA. Multiple tiled sgRNAs, will be used, which have been demonstrated to increase density of dCas9, thus allowing recruitment of more chromatin regulatory enzymes to the promoter of the target gene (Chen, B. et al. Cell 155, 1479-1491 (2013)). The development of CiA reporter lines at other genomic regions including identical DNA binding arrays and GFP reporters will be carried out. To date, two reported lines have been developed: one at a lowly-expressed region in the f-globin locus and the other in a highly-expressed region of the Rosa26 locus. With these lines, the function of the dCas9-bifunctional CEM approach will be tested at three different genomic regions to examine if the findings at the Oct4 loci are generalizable to other chromatin regions. These data will guide the development of the dCas9 protein engineering techniques and the medicinal chemistry experiments to make even more active bifunctional CEMs.

Example 7: Application of dCas9-FKBP Constructs and Bifunctional Chromatin Epigenetic Modifiers (CEMs) in Models of Prostate Cancer by Targeting the Androgen Receptor Signaling Axis The dCas9-FKBP constructs and bifunctional CEMs to recruit epigenetic machinery will be applied to in vitro and in vivo models of mPC. These experiments will serve as a first step towards the development of a dCas9-based mPC therapeutic (FIG. 11). The AR gene will be the focal point for these experiments, due to the central role of AR axis signaling in mPC, development of mCRPC, and secondary resistance to AR-targeting drugs (abiraterone and enzalutamide). dCas9-FKBP and bifunctional CEMs will also be used to repress additional genes associated with mPC: genes associated with androgen-independent AR activation and/or secondary resistance (e.g., the RAS oncogene and/or NRC31 that codes the glucocorticoid receptor) (Watson, P. A., Arora, V. K. & Sawyers, C. L. *Nat. Publ. Gr.* 15, 701-711 (2015); (Mills, I. G. *Nat. Publ. Gr.* 14, 187-198 (2014)); genes associated with DNA repair/cell cycle (e.g., BRCA2. PARP1 and/or TOP2β) (Watson, P. A., Arora, V. K. & Sawyers, C. L. *Nat. Publ. Gr.* 15, 701-711 (2015); (Mills, I. G. *Nat. Publ. Gr.* 14, 187-198 (2014); (Robinson, D. et al. *Cell* 161, 1215-1228 (2015); and genes that code epigenetic regulators of AR binding to chromatin e.g., FOXA1, GATA2, and/or BRD4) (Mills, I. G. *Nat. Publ. Gr.* 14, 187-198 (2014)).

Application of dCas9-FKBP constructs and bifunctional CEMs to in vitro models of mPC. First, the clinical potential of dCas9-FKBP constructs and bifunctional CEMs that target AR (and additional nodes) through a series of in vitro studies will be evaluated. Four prostate cancer lines will be used; each with distinct disease phenotypic features. LNCaP cells, derived from lymph node metastases, have high AR expression, low tumorigenicity, and are androgen sensitive (AS). DU-145 cells, derived from CNS metastases, have moderate AR expression and tumorigenicity, behave as osteolytic bone metastases, and are androgen insensitive (AI). PC-3 cells, derived from lumbar metastases, express low levels of AR, have high tumorigenicity, behave as osteolytic bone metastases, and are AL. C4-2B cells, a bone metastasis model developed from LNCaPs, have high AR expression and tumorigenicity, behave as osteoblastic bone metastases, and are AS. The dCas9-FKBP constructs will be formulated with a GFP backbone and the delivery efficiency will be evaluated by flow cytometry and immunocytochemistry (ICC). Epigenetic modulation of target genes (e.g., AR) will be assessed by mRNA expression via RT-PCR and flow cytometry, protein expression via WB, ELISA and ICC, and protein interactions with DNA will be assessed via chromatin immunoprecipitation sequencing (ChIP-seq). Cell viability and proliferation will be evaluated using the Cell-Titer-Glo assay (Promega). Molecular assays designed to assess the effects of the dCas9-FKBP constructs/bifunctional CEMs on cell cycle, and apoptosis (i.e., mitochondrial cytochrome C release and caspase-3 cleavage) will be conducted. For experiments involving bifunctional CEMs in combination with abiraterone and/or enzalutamide, drug dosing will be based on reported $IC_{50}$ concentrations from their New Drug Application (NDA).

Application of dCas9-FKBP constructs and bifunctional CEMs to a patient derived xenograft (PDX) mouse model of mPC. For these experiments, the clinical potential of the dCas9-FKBP constructs and bifunctional CEMs will be evaluated using a PDX mouse model. Prior to patient-derived xenograft implantation, dCas9-FKBP construct transfection will be optimized via electroporation or lentiviral delivery. NOD.CB17-Prkdc$^{scid}$/J mice (Jax Labs, Bar Harbor, Me.) will be implanted SQ with PC cells ($2 \times 10^6$) to the suprascapular region. When tumors reach 100 mm$^3$ (~20 days), bifunctional CEMs (or control vehicle) will be administered via tail vein IV. The dCas9-FKBP constructs will be developed with a luciferase backbone to estimate tumor distribution (% tumor vol.). Distribution will be assessed using the IVIS-100 system at the UNC Small Animal Imaging Center (Marsico Hall Vivarium) on days 1-5 post-injection. Changes in tumor size and body weight will be assessed every 2-3 days, and the extent of tumor necrosis will be evaluated via repeat ultrasounds (Vevo2100 at Marsico Hall). Epigenetic modulation assessments for each target gene (e.g., AR) will be conducted: mRNA expression via RT-PCR/flow cytometry, protein expression via WB/ELISA and immunohistochemistry (IHC), and histone pull downs via ChIP-seq. Molecular assays designed to assess dCas9-FKBP constructs/bifunctional CEMs effects on cell cycle, and apoptosis will be conducted. For experiments with bifunctional CEMs in combination with abiraterone and/or enzalutamide, drug dosing will be consistent with preclinical studies described in their respective NDAs.

Application of dCas9-FKBP constructs and bifunctional CEMs to a genetically engineered mouse (GEM) model of mPC. The next step towards the development of the dCas9-FKBP/CEM therapeutic for mPC will be to screen them in an in vivo genetically engineered mouse (GEM) model. First, a knock-in mouse will be prepared to incorporate dCas9-FKBP constructs at the Rosa26 locus (C57BL (Rosa26$^{dCas9-FKBP}$)/6J), and then bifunctional CEMs will be administered IV over a dose range to determine optimal bifunctional CEM concentration. A PTEN knockout GEM model will be used in these experiments, which will be developed by breeding a Tg(Pbsn-cre)4Prb/J mouse with a C57BL(Ptenn$^{flox}$)/6J mouse (Jax Labs). The first strain expresses Cre recombinase under the control of the rat Pbsn (probasin, gene promoter) in prostate epithelium, while the second strain possesses loxP sites flanking exon 5 of PTEN. This cross strain after 3 generations will be useful as a prostate cancer GEM model. Then the GEM will be bred with the C57BL(Rosa26$^{dCas9-FKBP}$)/6J. Mice will be aged until the tumors are visible via PET-CT (GE eXplore Vista at Marsico Hall). Upon tumor confirmation, bifunctional CEMs (or sham) will be administered via tail vein. Distribution will be assessed by IVIS-100, and PET-CT at days 1-5 post-injection. Effects of dCas9-FKBP/CEM on the tumor, extent of epigenetic modulation, and experiments in combination with abiraterone and/or enzalutamide will be conducted as described herein.

Example 8: Gene Specific Activation Driven by Small Molecules

Figure 19A:
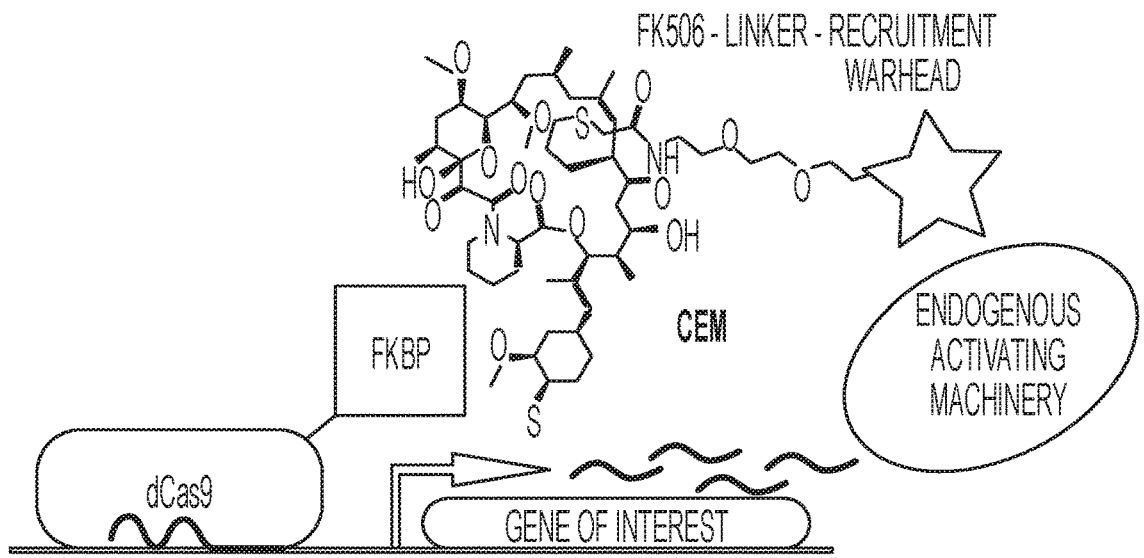
FIGS. 19A-D shows a dCas9 CEMa system that recruits endogenous chromatin modifying machinery to regulate transcriptional activity.
Figure 19B:
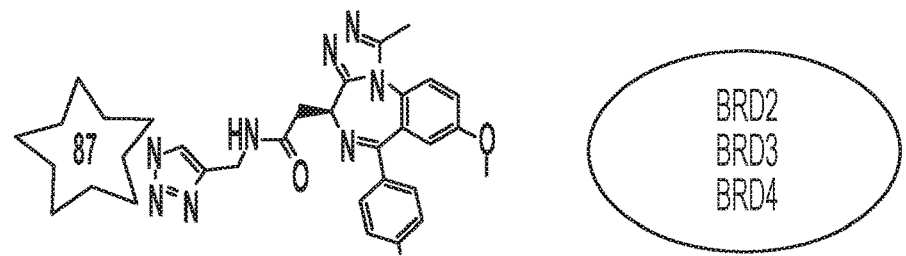
Figure 19C:
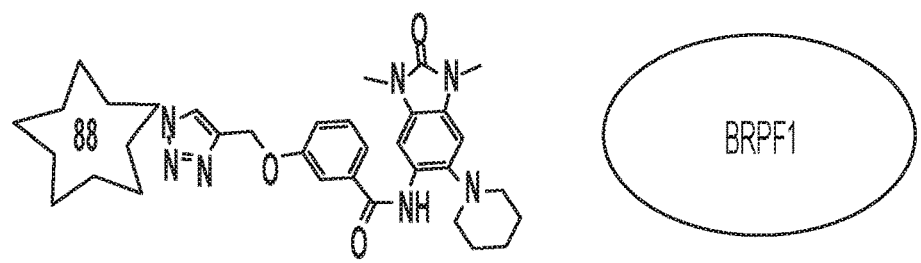
Figure 20B:
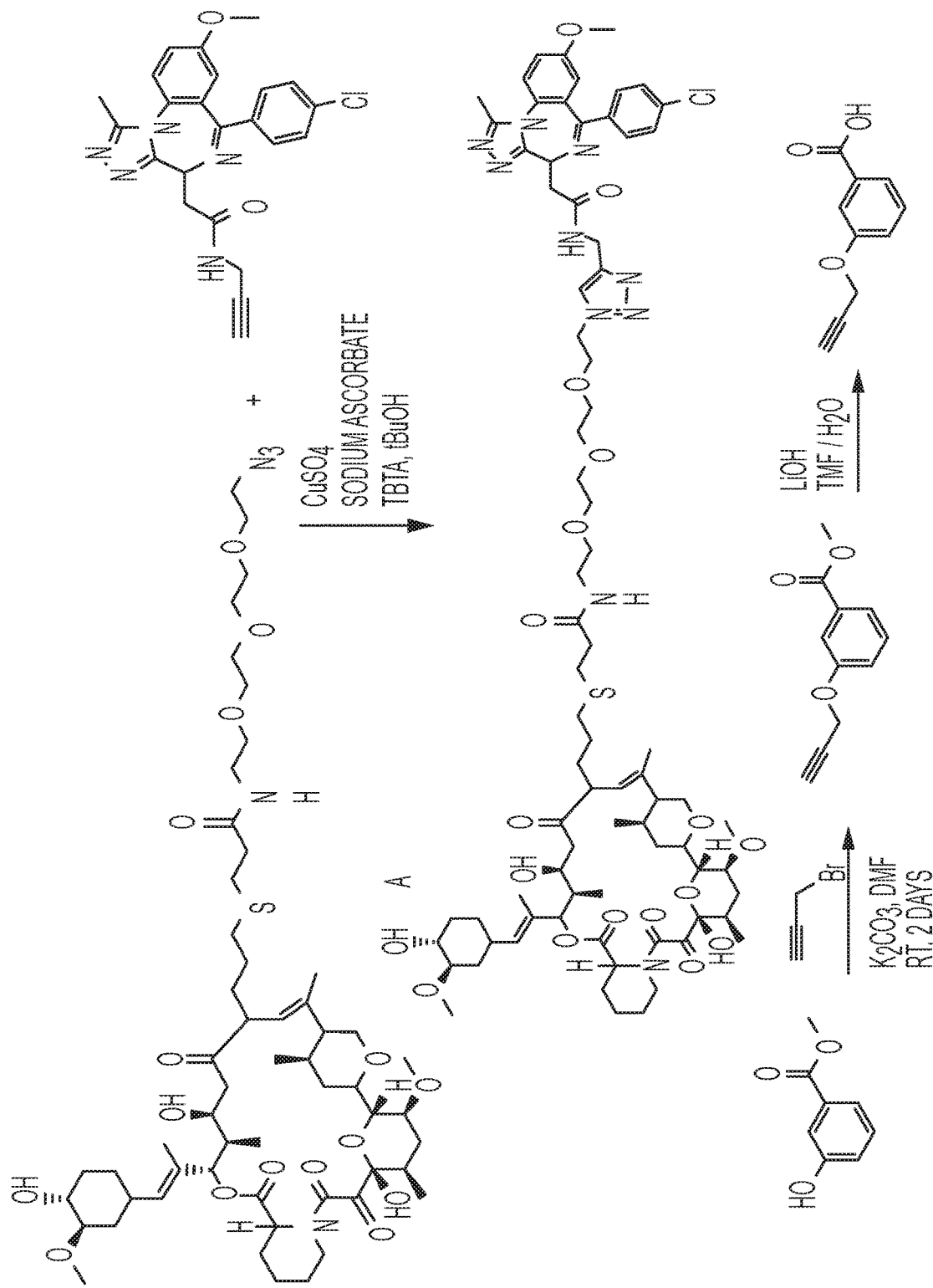
Figure 20C:
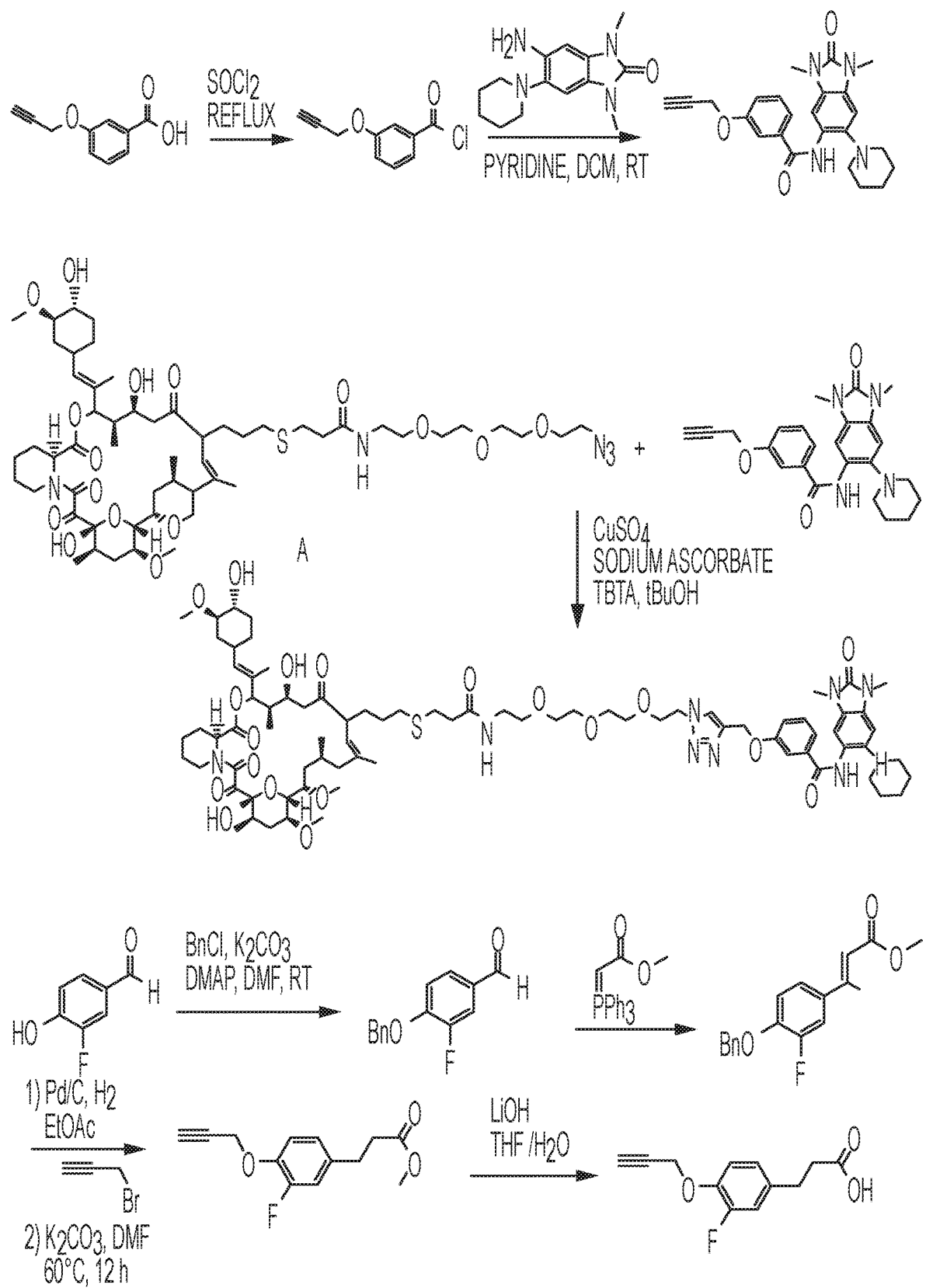
Figure 20D:
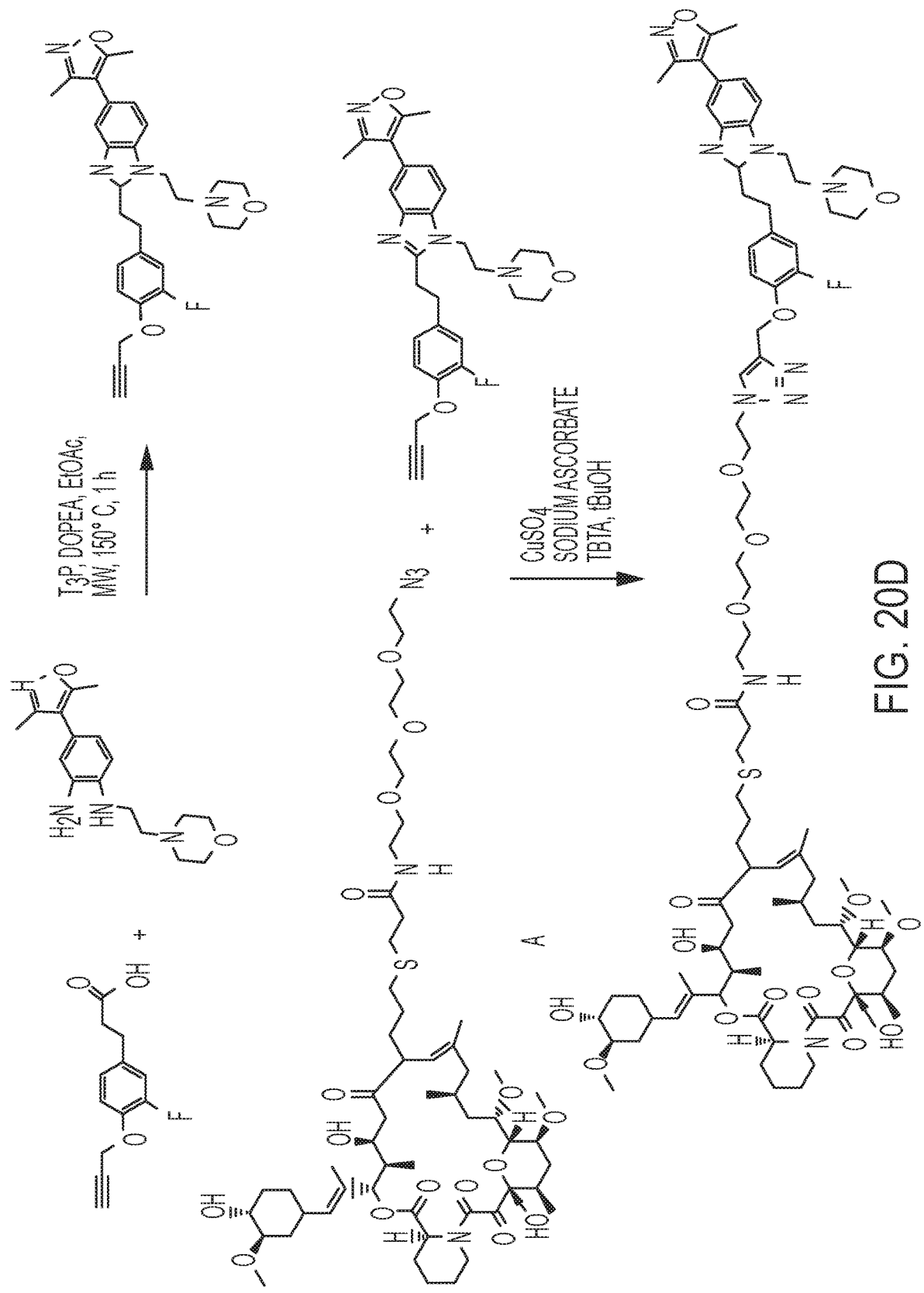

The ability of bifunctional chemical epigenetic modifiers (CEMs) to control the chromatin landscape and repress genes in a specific and reversible manner has been demonstrated (Butler, K. V. et al. *ACS Synth. Biol.* 7, 38-45 (2018)) and is described herein. Also described herein are bifunctional CEMa (CEM activating) molecules which recruit activating chromatin modifying machinery. The bifunctional CEMa family includes CEM87, CEM88, and CEM114 that bind to activating chromatin modifying enzymes with various binding efficiencies. The bifunctional ligand of the bifunctional CEM used to recruit chromatin modifying machinery can include inhibitors of HATs or lysine reader proteins (FIG. 19A). Changes in transcriptional activity are evident by increases in fluorescent protein levels and relative mRNA quantification. dCas9-FKBP is introduced by transfection, or by infection of lentiviral delivery units. The CEMa molecules are brought to the gene-of-interest through interaction of the FK506 moiety with FKBP. Blue lines represent mRNA. CEM87 was created with iBet762, and shown to inhibit BRD2, BRD3, and BRD4 (Chung, C. et al. *J. Med. Chem.* 54, 3827-3838 (2011)) (FIG. 19B, FIG. 20A, B). CEM88 was created with a 1,3-dimethyl benzimidazolone, previously shown to inhibit the BRPF1 bromodomain (FIG. 19C, FIG. 20A, C (Demont, E. H. et al. *ACS Med. Chem. Lett.* 5, 1190-1195 (2014)). Lastly, CEM114 was created with "compound 33", and shown to inhibit CBP (FIG. 1D, FIG. 20A, D) (Hay, D. A. et al. *J Am Chem Soc.* 136, 9308-9319 (2014)).

Chemistry general procedures. FK506 was purchased from Selleckchem. All other chemicals were purchased from SigmaAldrich or Fisher Scientific. HPLC spectra for the compounds were acquired using an Agilent 1200 Series system with DAD detector. Analytical HPLC chromatography was performed on a 2.1×150 mm Zorbax 300SB-C18 5 μm column with water containing 0.1% formic acid as solvent A and acetonitrile containing 0.1% formic acid as solvent B at a flow rate of 0.4 mL/min. The gradient program was as follows: 1% B (0-1 min), 1-99% B (1-4 min), and 99% B (4-8 min). High resolution mass spectra (HRMS) data were acquired in positive ion mode using an Agilent G1969A API-TOF with an electrospray ionization (ESI) source. Flash column chromatography was performed on a Teledyne ISCO CombiFlash Rf system equipped with a variable wavelength UV detector and a fraction collector using RediSep Rf normal phase silica columns. Microwave reactions were performed using a Discover SP CEM. Nuclear Magnetic Resonance (NMR) spectra were acquired on a Bruker DRX-600 spectrometer with 600 MHz for proton ($^1$H NMR) and 150 MHz for carbon (Chung, C. et al. *J. Med. Chem.* 54, 3827-3838 (2011) C NMR); chemical shifts are reported in ppm (δ). Preparative HPLC was performed on Agilent Prep 1200 series with UV detector set to 254 nm. Samples were injected onto a Phenomenex Luna 75×30 mm, 5 μm, C18 column at room temperature. The flow rate was 30 mL/min. A linear gradient was used with 10% (or 50%) of MeOH (A) in H2O (with 0.1% TFA) (B) to 100% of MeOH (A). HPLC was used to establish the purity of target compounds. All final compounds had >95% purity using the HPLC methods described herein.

3-(prop-2-yn-1-yloxy)benzoic acid: To the solution of methyl 3-hydroxybenzoate (760 mg, 5 mmol) in DMF (10 mL) was added $K_2CO_3$ (1.38 g, 10 mmol). Then, 3-bromoprop-1-yne (1.49 mL, 10 mmol) was added, and the reaction was stirred at room temperature for 2 days. Water and ethyl acetate (EtOAc) were added, and the aqueous phase was extracted with EtOAc (3×20 mL). The combined organic layers were washed with water, brine, and dried over Na2SO4. The solvent was removed and dried under vacuum. The crude product (950 mg, 5 mmol), which was used for next step without further purification, was dissolved in THF/H2O (25 mL/25 mL). Then, LiOH (1.0 g, 43 mmol) was added, and the reaction was stirred at room temperature overnight. The reaction mixture was then treated with 4 N HCl until pH=1, and extracted with EtOAc (3×30 mL), dried over $Na_2SO_4$. The solvent was removed under reduced pressure to obtained the title compound (801 mg, yield 91% over two steps). $^1$H NMR (600 MHz, Chloroform-d) δ 7.79 (dt, J=7.7, 1.2 Hz, 1H), 7.73 (dd, J=2.9, 1.5 Hz, 1H), 7.44 (t, J=7.9 Hz, 1H), 7.30-7.20 (m, 1H), 4.78 (d, J=2.4 Hz, 2H), 2.58 (t, J=2.3 Hz, 1H).

N-(1,3-dimethyl-2-oxo-6-(piperidin-1-yl)-2,3-dihydro-1H-benzo[d]imidazol-5-yl)-3-(prop-2-yn-1-yloxy)benzamide: 3-(prop-2-yn-1-yloxy)benzoic acid (200 mg, 1.13 mmol) was dissolved in excess $SOCl_2$, and the reaction was heated to reflux for 2 h. Then, the mixture was cooled and concentrated to generate 3-(prop-2-yn-1-yloxy)benzoyl chloride for the next step without purification. To a solution of 5-amino-1,3-dimethyl-6-(piperidin-1-yl)-1H-benzo[d]imidazole-2(3H)-one (synthesized as previously described MacDonald, I. A. & Hathaway, N. A. *Immunol. Cell Biol.* 93, 261-70 (2015) (323 mg, 1.24 mmol) in $CH_2Cl_2$ (10 mL) was added pyridine (0.114 mL, 1.41 mmol) at room temperature. Then, 3-(prop-2-yn-1-yloxy)benzoyl chloride (220 mg, 1.13 mmol) was added and the reaction mixture was stirred for 1 h at this temperature. The reaction was diluted with DCM and washed by saturated $NaHCO_3$ solution, and the aqueous phase was extracted with DCM. The combined organics were washed with water, dried over $Na_2SO_4$. The solvent was removed under reduced pressure and the residue was purified by flash chromatography on silica gel (50%-100% of EtOAc in Hexanes), and to obtain the product as white solid (294 mg, yield 62%). $^1$H NMR (600 MHz, Methanol-d4) δ 8.19 (s, 1H), 7.57-7.45 (m, 3H), 7.29-7.22 (m, 1H), 7.16 (s, 1H), 4.84 (d, J=2.4 Hz, 2H), 3.41 (d, J=4.8 Hz, 6H), 3.01 (t, J=2.4 Hz, 1H), 2.88 (t, J=5.2 Hz, 4H), 1.79 (p, J=5.7 Hz, 4H), 1.65 (brs, 2H). HRMS (m/z) [M+H]+ for $C_{24}H_{27}N_4O_3+$ calculated 419.2078, found 419.2155.

CEM88: Compound A[1] (39 mg, 0.035 mmol) and N(1,3-dimethyl-2-oxo-6-(piperidin-1-yl)-2,3-dihydro-1H-benzo[d]imidazol-5-yl)-3-(prop-2-yn-1-yloxy)benzamide (15 mg, 0.035 mmol) were dissolved in tertButanol (1 mL). TBTA (2 mg, 10 mol %), copper sulfate pentahydrate (0.035 mL, 10 mol %, 0.1 M), and sodium ascorbate (0.17 mL, 0.2 equiv.) were added, and the reaction was stirred at room temperature for 24 h. The reaction mixture was purified by preparative HPLC (10%-100% methanol/0.1% TFA in H2O) to afford CEM88 as white solid in TFA salt form (38 mg, yield 71%). $^1$H NMR (600 MHz, Methanol-d4) δ 8.19 (s, 1H), 7.83-7.57 (m, 2H), 7.55-7.44 (m, 2H), 7.36-7.30 (m, 2H), 5.30 (s, 2H), 5.24-5.08 (m, 2H), 4.63-4.58 (m, 3H), 4.33 (d, J=13.6 Hz, 1H), 4.06-3.87 (m, 3H), 3.74-3.67 (m, 1H), 3.63-3.53 (m, 11H), 3.55-3.36 (m, 19H), 3.07-2.92 (m, 2H), 2.79 (dd, J=14.4, 5.8 Hz, 1H), 2.68 (t, J=7.2 Hz, 2H), 2.46 (s, 2H), 2.40 (t, J=7.3 Hz, 2H), 2.37-2.23 (m, 2H), 2.21-2.07 (m, 3H), 2.06-1.68 (m, 18H), 1.67-1.56 (m, 8H), 1.56-1.26 (m, 10H), 1.25-1.16 (m, 1H), 1.09 (q, J=12.9, 12.4 Hz, 1H), 0.99-0.79 (m, 11H). HRMS (m/z) [M+H]+ for $C_{79}H_{118}N_9O_{19}S^+$ calculated 1528.8259, found 1528.8327. HPLC tR=4.76 min.

3-(3-fluoro-4-(prop-2-yn-1-yloxy)phenyl)propanoic acid: To a solution of 3-fluoro-4-hydroxybenzaldehyde (1.40 g, 10 mmol) in dimethyl formamide (DMF) (20 mL) was added benzylchloride (1.39 mL, 12 mmol), $K_2CO_3$ (2.04 g, 15 mmol), and DMAP (10 mg). The reaction was stirred overnight at room temperature. Water and EtOAc were added, and the aqueous phase was extracted with EtOAc (3×20 mL). The combined organic layers were washed with water, brine, and dried over $Na_2SO_4$. The solvent was removed under reduced pressure, and the residue was purified by flash chromatography on silica gel (0%-10% of EtOAc in Hexane). The product 4-(benzyloxy)-3-fluorobenzaldehyde was obtained as white solid (1.33 g, yield 58%). 4-(benzyloxy)-3-fluorobenzaldehyde (1.33 g, 5.8 mmol) and methyl (triphenylphosphoranylidene) acetate (2.12 g, 6.4 mmol) were dissolved in DCM (20 mL). The resulting mixture was stirred at room temperature for 3 days. The solvent was removed and purified by flash chromatography on silica gel (0%-25% of EtOAc in Hexane). Methyl 3-(4-(benzyloxy)-3-fluorophenyl) acrylate was obtained as white solid (1.55 g, yield 93%) and dissolved in EtOAc (50 mL). Pd/C (200 mg) was added and the reaction was stirred under H2 for 18 h. The Pd/C was filtered through Celite, and the filtrate was concentrated. The crude product was dissolved in DMF (20 mL). Then, 3-bromoprop-1-yne (0.72 mL, 6.5 mmol) and $K_2CO_3$ (1.1 g, 8.1 mmol) were added. The reaction was stirred at 60° C. overnight. Water and EtOAc were added, and the aqueous phase was extracted with EtOAc (3×20 mL). The combined organic layers were washed with water, brine, and dried over $Na_2SO_4$. The solvent was removed and purified by flash chromatography on silica gel (0%-50% of EtOAc in Hexane). Methyl 3-(3-fluoro4-(prop-2-yn-1-yloxy)phenyl)propanoate was obtained as white solid (892 mg, yield 70%). Methyl 3-(3-fluoro-4-(prop-2-yn-1-yloxy)phenyl)propanoate (850 mg, 3.6 mmol) was dissolved in THF/$H_2O$ (8 mL/8 mL). LiOH (432 mg, 18 mmol) was added, and the reaction was stirred at room temperature overnight. The reaction was treated with 2 N HCl until pH=1, extracted with EtOAc (3×30 mL), dried over Na2SO4. The solvent was removed to get the title product (754 mg, yield 94%). $^1$H NMR (600 MHz, Methanol-d4) δ 7.10 (t, J=8.5 Hz, 1H), 7.00 (dd, J=25.3, 10.2 Hz, 2H), 4.77 (q, J=3.5 Hz, 2H), 3.02-2.92 (m, 1H), 2.87 (d, J=7.4 Hz, 2H), 2.64-2.54 (m, 2H). 4-(2-(5-(3,5-dimethylisoxazol-4-yl)-2-(3-fluoro-4-(prop-2-yn-1-yloxy)phenethyl)-1H-benzo[d]imidazol-1-yl)ethyl)morpholine: 3-(3-fluoro-4-(prop-2-yn-1-yloxy)phenyl)propanoic acid (53 mg, 0.24 mmol) and 4-(3,5-dimethylisoxazol-4-yl)-N1-(2-morpholinoethyl)benzene-1,2-diamine (synthesized as previously described[3]) (63 mg, 0.2 mmol) were dissolved in EtOAc (0.7 mL). T3P (0.578 mL, 1 mmol) and DIPEA (0.041 mL, 0.24 mmol) were added, then, the reaction was heated to 150° C. for 10 minutes in microwave reactor (MW). Water was added to quench the reaction, and the aqueous phase was extracted with EtOAc (3×5 mL), dried over $Na_2SO_4$. Solvent was removed and the resulting mixture was purified by preparative HPLC (10%-100% methanol/0.1% TFA in $H_2O$) to afford title compound as white solid in TFA salt form (41 mg, yield 41%). $^1$H NMR (600 MHz, Methanol-d4) δ 8.04 (d, J=8.6 Hz, 1H), 7.74 (d, J=1.4 Hz, 1H), 7.60 (dd, J=8.6, 1.5 Hz, 1H), 7.19-7.11 (m, 2H), 7.03 (d, J=8.3 Hz, 1H), 4.78 (d, J=2.4 Hz, 2H), 3.94 (s, 4H), 3.58 (t, J=7.8 Hz, 2H), 3.54-3.48 (m, 2H), 3.35 (d, J=9.1 Hz, 4H), 3.31 (p, J=1.6 Hz, 4H), 2.98 (t, J=2.5 Hz, 1H), 2.44 (s, 3H), 2.27 (s, 3H). HRMS (m/z) $[M+H]^+$ for $C_{29}H_{32}FN_4O_3+$ calculated 503.2453, found 503.2442. CEM114: CEM114 was synthesized following the standard procedures for preparing CEM88 from Compound $A^1$ (36 mg, 0.032 mmol) and 4-(2-(5-(3,5-dimethylisoxazol-4-yl)-2-(3-fluoro-4-(prop-2-yn-1-yloxy)phenethyl)-1H-benzo[d]imidazol-1-yl) ethyl)morpholine (20 mg, 0.032 mmol), TBTA (1 mg, 10 mol %), copper sulfate pentahydrate (0.032 mL, 10 mol %, 0.1 M), and sodium ascorbate (0.16 mL, 0.2 equiv) in tert-Butanol (1 mL). The reaction mixture was purified by preparative HPLC (10%-100% methanol/0.1% TFA in $H_2O$) to afford CEM114 as white solid in TFA salt form (23 mg, yield 45%). $^1$H NMR (600 MHz, Methanol-d4) δ 8.16 (d, J=2.8 Hz, 1H), 7.98 (dd, J=8.6, 3.2 Hz, 1H), 7.72 (s, 1H), 7.58 (dd, J=8.6, 1.5 Hz, 1H), 7.19 (td, J=8.5, 5.3 Hz, 1H), 7.15-7.10 (m, 1H), 7.01 (t, J=8.6 Hz, 1H), 5.24-5.12 (m, 4H), 4.66-4.57 (m, 3H), 4.28 (d, J=13.4 Hz, 1H), 4.06-3.94 (m, 1H), 3.89 (dd, J=12.9, 7.8 Hz, 7H), 3.75-3.66 (m, 1H), 3.63-3.51 (m, 13H), 3.48 (t, J=5.5 Hz, 3H), 3.43-3.36 (m, 8H), 3.26-3.11 (m, 7H), 3.01 (ddd, J=15.0, 9.6, 4.1 Hz, 1H), 2.92 (t, J=12.4 Hz, 1H), 2.80 (dd, J=14.3, 5.3 Hz, 1H), 2.70 (t, J=7.2 Hz, 2H), 2.51-2.40 (m, 8H), 2.28 (s, 5H), 2.23-1.97 (m, 6H), 1.95-1.68 (m, 9H), 1.68-1.30 (m, 17H), 1.24-1.14 (m, 1H), 1.13-1.04 (m, 1H), 1.00-0.77 (m, 11H). HRMS (m/z) $[M+H]^+$ for $C_{84}H_{123}N_9O_{19}S^+$ calculated 1612.8634, found 1612.8475. HPLC tR=4.27 min.

The FKBP-interacting moiety (FK506) and the peg-linker were used as they functioned successfully with other synthesized bifunctional CEMs. As also described herein the coupling of this synthetic technique is compatible with dCas9-FKBP-based systems allowing bifunctional CEMs to be directed to virtually any gene of interest. By recruiting endogenous cellular machinery associated with euchromatin and increased gene expression, it was tested whether the bifunctional CEMs would increase transcriptional activity in a dose- and chemically-dependent manner.

Figure 21A:
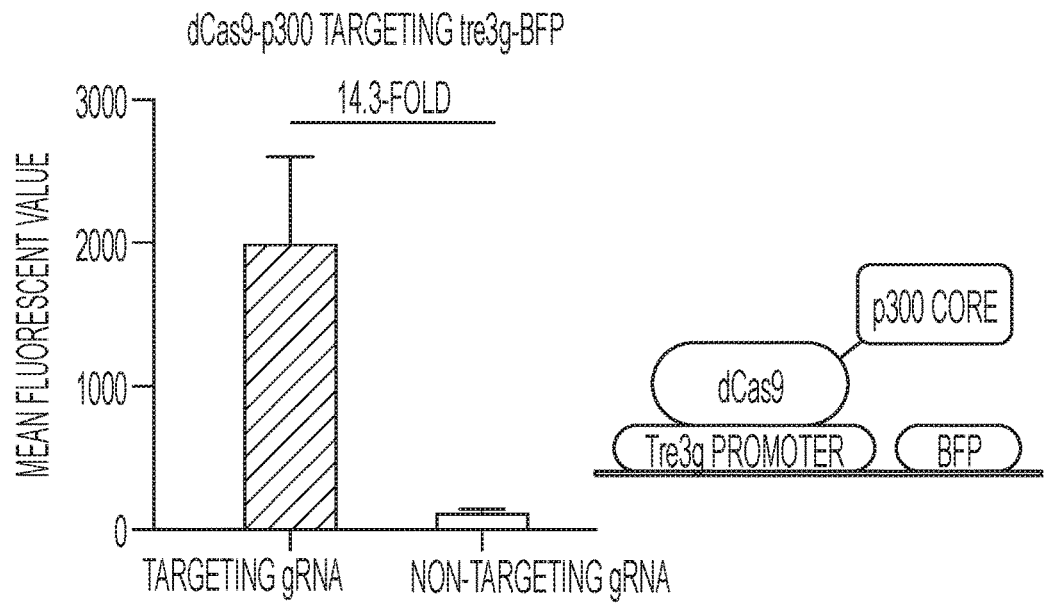
FIGS. 21A-D show protein engineering and synthetic chemistry used to improve the dCas9-CEMa system. HEK 293T cells were transfected with a reporter plasmid that carried a BFP gene (driven by a Tre3G promoter that has low expression) along with a sgRNA targeting the Tre3G promoter and the dCas9. The samples were measured by flow cytometry 48-hrs after treatment.
Figure 21B:
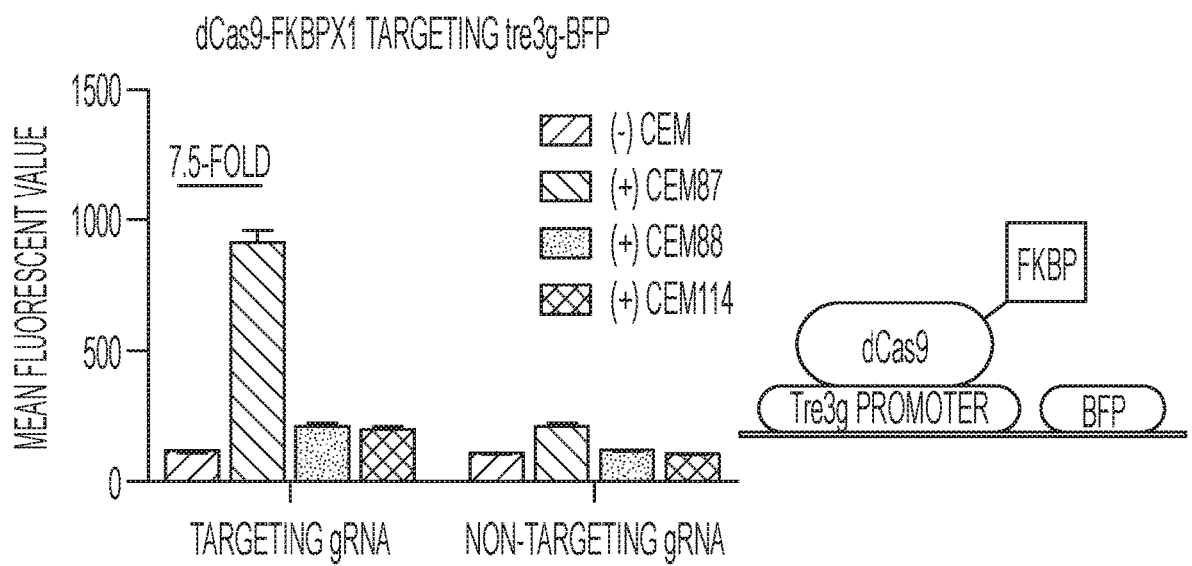

To test for changes in gene expression, human embryonic kidney (HEK) 293T cells were transfected with a BFP reporter gene downstream of a tre3g promoter and performed flow cytometry on at least 100,000 cells after co-expressing the gRNA and dCas9 machinery(Ma, D. et al. Nat. Commun. 7, 13056 (2016)). As a benchmark control for gene activation, a dCas9-p300 fusion protein known to increase expression was used (Hilton, I. B. et al., Nat. Biotechnol. 33, 510-517 (2015)). Using a gRNA that targets the tre3g promoter at six interspaced sites, the dCas9-p300 increased BFP expression 14-fold compared to the non-targeting (NT) control gRNA (FIG. 21A, $p<0.05$). Next, activating the reporter gene with a plasmid expressing dCas9 (N-terminus)-FKBPx2 (C-terminus) was tested using three predicted activating bifunctional CEMs. After 48 hours of exposure to 200 nM of CEM87, CEM88 and CEM114, BFP expression significantly increased 7.5, 1.8, 1.6-fold, respectively, compared to untreated cells (FIG. 21B, $p<0.005$, 0.000001, 0.05, respectively).

Figure 22:
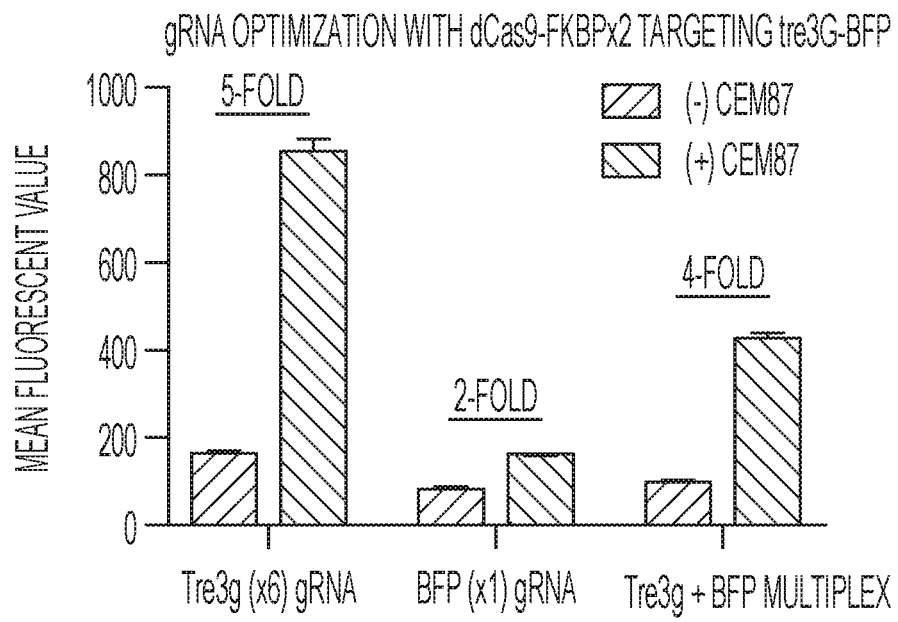
FIG. 22 shows dCas9-CEMa gRNA improvement. HEK 293T cells were transfected with dCas9-FKBPx2, a BFP reporter, and one of 3 gRNAs sets as indicated.
Figure 23:
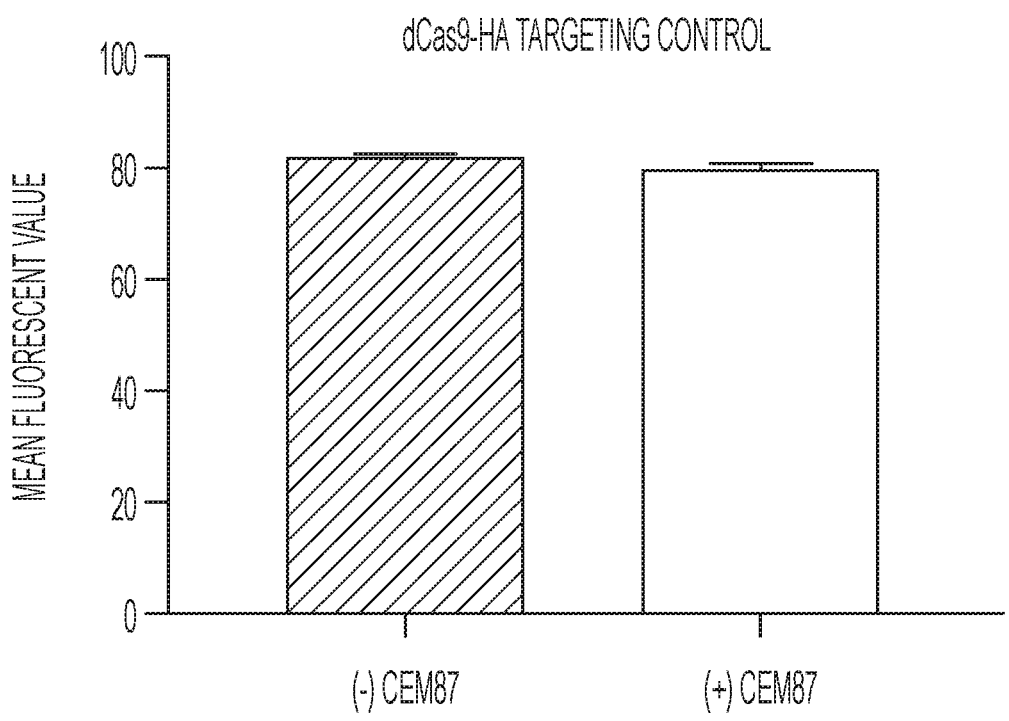
FIG. 23 shows dCas9-HA control.

Improvement of the dCas9-CEMa system was done by testing gRNAs targeted to areas along the span of the promoter and increasing the density of recruitment, as this has been previously shown to have a great impact on dCas9 efficiency (Radzisheuskaya, A. et al. Nucleic Acids Res. 44, e141 (2016); (Lawhorn, I. E. B. et al. PLoS One 9, e113232 (2014); (Braun, C. J. et al. Proc. Natl. Acad. Sci. U.S.A 113, E3892-900 (2016)). Cells were transfected with plasmids expressing the BFP reporter, one or multiple gRNA, and dCas9, and were either treated with 200 nM of CEM87 for 48 hours or given regular media. Compared to the untreated control cells, the bifunctional CEM-treated cells expressing the 6×-tre3g gRNA showed a 5-fold increase in BFP expression (FIG. 22, $p<0.0005$). The cells expressing a gRNA designed at a single site, further into the gene body, showed a 2-fold increase (FIG. 22, $p<0.00000005$). A multiplexing gRNA plasmid, whereby the cells would express the 6×-tre3g gRNA and the single site gRNA (Sakuma, T. et al. Sci. Rep. 4, 4-9 (2014)), was also tested. This multiplex gRNA led to an activation of 4-fold (FIG. 22, $p<0.0005$). It is possible that the less-effective single-site gRNA led the chromatin modifying machinery away from the promoter and drove down the overall effectiveness of the system. For additional experiments, the 6×-tre3g gRNA plasmid was used. To serve as a positive control for CEMa exposure upon dCas9 and gRNA recruitment, HEK 293T cells were also transfected with dCas9-HA (with no FKBP recruitment site) and the targeting 6×-tre3g gRNA. Treated cells were exposed to 200 nM of CEM87 for 48 hours. As expected, the addition of CEM87 at 200 nM did not significantly affect the BFP expression; flow cytometry showed no significant changes in gene expression as measured by BFP ($p>0.05$). (FIG. 23).

Figure 21C:
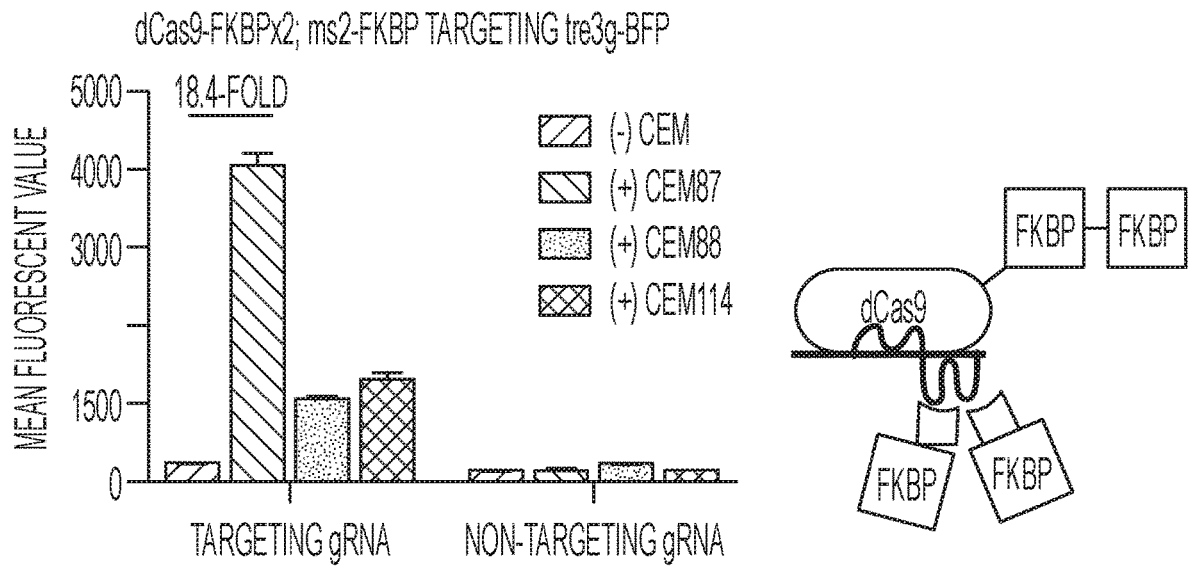
Figure 21D:
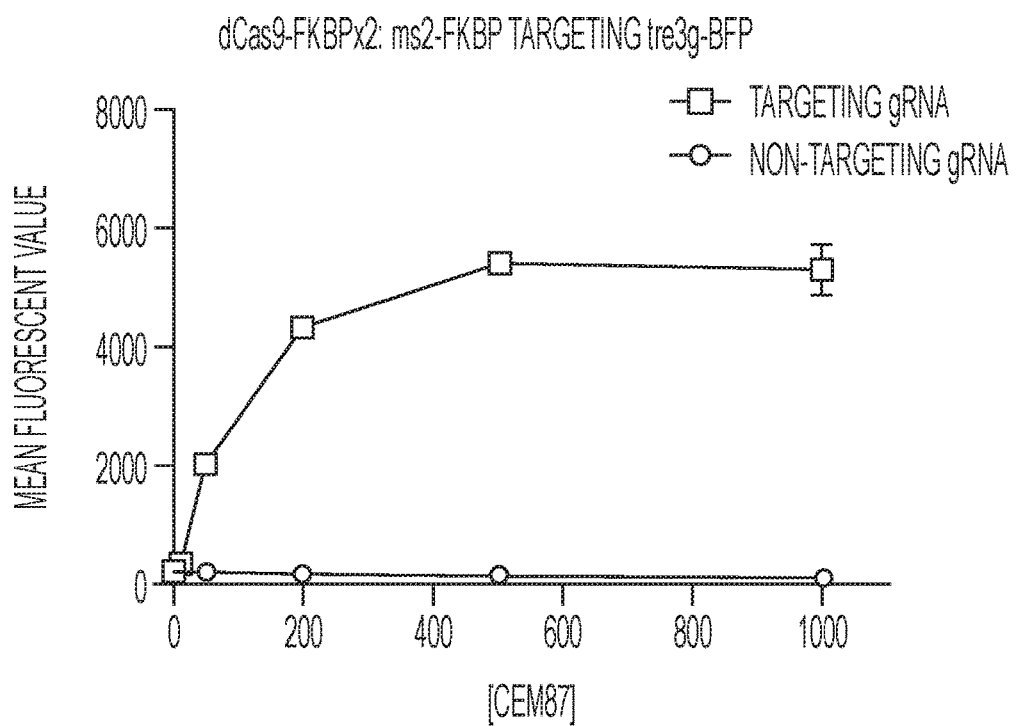
Figure 24:
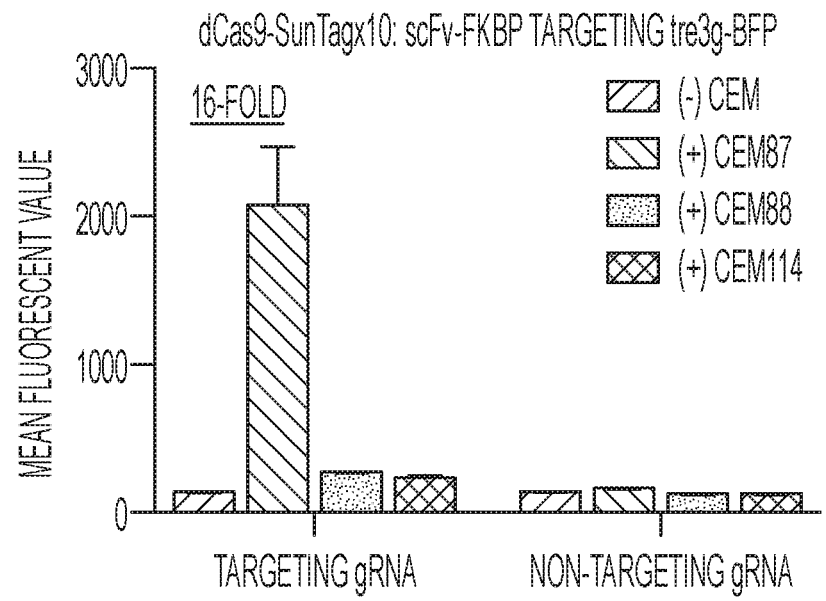
FIG. 24 shows a dCas9-SunTag approach adapted to the dCas9-CEMa system.

Next, it was tested whether increasing bifunctional CEM-recruitment would yield a more effective and highly doseable system and increase the number of FKBP molecules being recruited to the gene of interest. The dCas9 "SunTag" system was adapted to be compatible with the bifunctional CEMa technology(Tanenbaum, M. E. et al. Cell 159, 635-646 (2014); (Chavez, A. et al. Nat. Methods 13, 563-567 (2016)). Using the improved dCas9-CEMa system (dCas9-FKBPx2, ms2-FKBP, tre3g ×6 gRNA, BFP reporter), the effects of a global epigenetic inhibitor in combination with a gene-specific approach was tested. After the cells were transfected, they were treated with 200 nM of CEM87 and 2.5 µM of Entinostat. BFP expression increased 34-fold compared to unreated cells as measured by flow cytometry. More specifically, A dCas9-SunTagx10 plasmid was used that expresses an array of 10 yeast-specific GCN4 (gene control protein 4) peptides from the C-terminus of the dCas9, and co-transfected with a single chain variable fragment (scFv), (made to be GCN4-specific) fused to FKBP. Theoretically, as many as 10 FKBP molecules per dCas9 would be recruited to the gene of interest, increasing the bifunctional CEMa recruitment power. With the adapted SunTag method and the tre3g ×6 gRNA, 48 hours of 200 nM CEM87 exposure increased expression 16-fold compared to untreated cells (FIG. 24, $p<0.001$). Equimolar CEM88 and CEM114 increased expression 2-fold (FIG. 24, $p<0.005$ and $p<0.05$, respectively). Another protein-engineering approach that was used to optimize the dCas9-CEMa system was incorporating ms2-compatible gRNAs. The ms2-gRNAs have a modified stem-loop, capable of recruiting both a dCas9-fusion as well as a bacteriophage MS2 coat protein (MCP)-fusion (Braun, S. M. G. et al. Nat. Commun. 8, (2017); (Konermann, S. et al. Nature 517, 583-588 (2015)). By using an MCP-FKBP fusion, the number of FKBPs was increased by 2-fold (as two MCP fusions can bind one stem loop) and the proximity of recruited bifunctional CEMa was physically increased to the chromatin. Compared to the untreated cells, CEM87 increased BFP expression 18-fold ($p<0.0000005$). With a system described herein (e.g., comprising the dCas9-FKBPx2; ms2-FKBP; and the tre3g ×6 gRNA), the other bifunctional CEMa compounds were retested to determine whether their activating efficiency also improved. Equivalent concentrations of CEM88 increased expression 5-fold ($p<0.0005$), and CEM114 increased expression 6-fold ($p<0.001$) compared to cells expressing the NT gRNA (FIG. 21C). With the improved dCas9 system and the most efficient bifunctional CEMa, CEM87, a dose-curve was performed and the ideal concentration for maximum expression was determined to be 200 nM (FIG. 21D). Since activity is governed by amount of small molecule ligand added, with this technique gene expression can be intricately controlled obtaining 2-fold activation at 10 nM, $p<0.05$ and 8-fold activation at 50 nM, $p<0.001$. At concentrations of 500 nM and above, the cells appeared less healthy as assessed by cell density and morphology (data not shown). Thus, dCas9-CEMa platform has control of gene activity and by varying compound dose between 0 and 200 nM the level of gene expression can be differentially modulated. These data demonstrate that transcriptional activity, as measured by mean fluorescence, can be tightly controlled with CEMa concentration, see, FIG. 21D). This could be useful for target validation studies, which is an area of the drug development pipeline in desperate need of new tools if clinical success rates are to be improved (Begley, C. G. & Ellis, L. M., Nature 483, 531-533 (2012); (Hay, M. et al. Nat. Biotechnol. 32, 40-51 (2014)).

Figure 25:
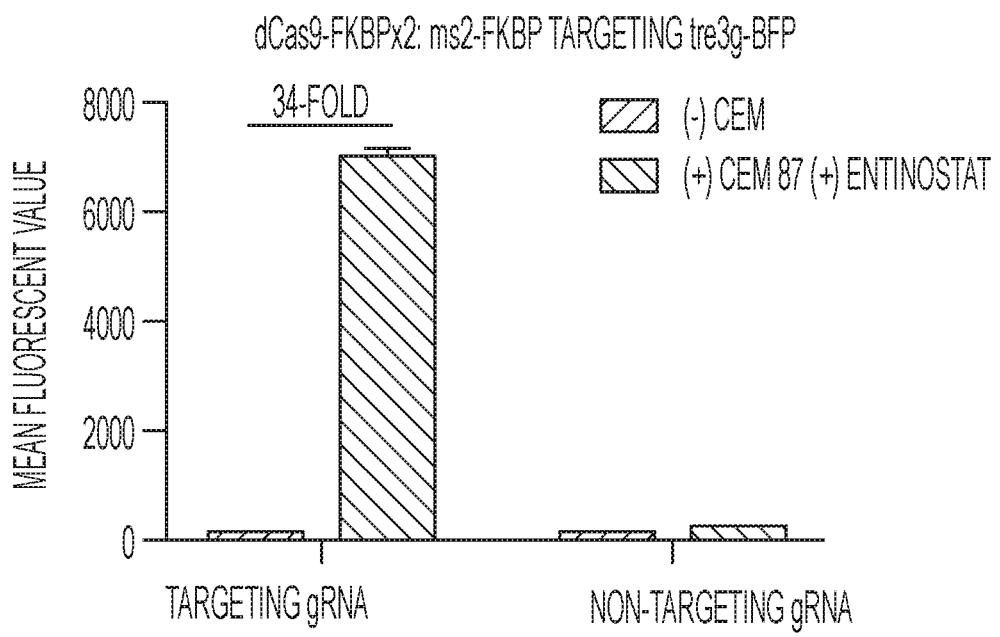
FIG. 25 shows CEMa in combination with an HDACi.

Another question asked was what would happen with a dual compound exposure of (1) the gene-specific system of activation with CEM87 and (2) a globally effective HDACi. Upon treatment of 2.5 µM of entinostat, a previously characterized HDAC inhibitor, and 200 nM of CEM87 with the dCas9-FKBPx2, ms2-FKBP recruitment system, a 34-fold gene activation was observed compared to untreated cells (FIG. 25, $p<0.0005$) (Saito, A. et al. Med. Sci. 96, 4592-4597 (1999)). While the purpose of the bifunctional CEMs system is to target transcriptional activity at a gene-specific level, these data suggest a synergistic effect with complimentary chromatin-regulatory pathways.

Figure 26:
FIG. 26 shows the dCas9-p300 time course at MYOD1.
Figure 27A:
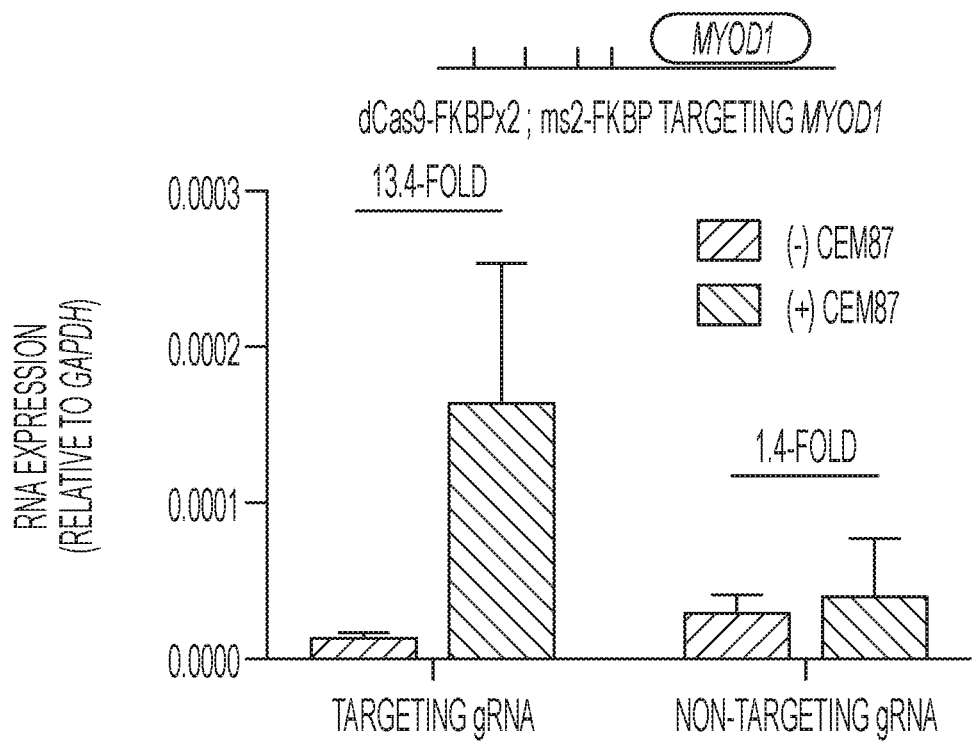
FIGS. 27A-C show the improved dCas9-CEMa effectively reactivates three diverse mammalian genes.

Next, the plasmid-optimized dCas9-CEMa system was adapted to target endogenous mammalian genes. Because an endogenous gene was being targeted rather than hundreds of transiently expressing reporter plasmids, the dCas9 machinery (dCas9-p300, dCas9-FKBPx2 and/or MCP-FKBP) was chosen to transfect HEK 293T cells. After the cells were stably selected for integration of the dCas9- and MCP-expressing plasmids, the gRNAs that were designed to target endogenous genes were transfected. To determine the time point at which to observe more efficient dCas9 regulation by this method, cells expressing dCas9-p300 were transfected with gRNAs for myogenic differentiation (MYOD1), the RNA was extracted and qRT-PCR was performed after 24, 48 and 72 hours post transfection. RNA extraction and qRT-PCR was performed on HEK 293T cells infected with dCas9-p300, and transfected MYOD1-targeting or control gRNA as indicated (see, FIG. 26) MYOD1 served as an initial target for this question because it has been previously shown to be capable of modulation by transiently expressed dCas9-p300 (Hilton, I. B. et al. Nat. Biotechnol. 33, 510-517 (2015)). With dCas9-p300 infected and the gRNAs transfected, it was found that dCas9-mediated gene regulation was most efficient after 48 hours (FIG. 26). FIG. 26 shows that Compared to the NT-gRNA cells, dCas9-p300 increased MYOD1 expression 15-fold 24 hours after transfection ($p<0.01$), 52-fold 48 hours after transfection ($p<0.05$), and 44-fold 72 hours after transfection ($p<0.01$). To test the ability of CEM87 to activate endogenous genes. Overall improved strategy in HEK 293T cell lines with stably expressing dCas9-FKBPx2 and ms2-FKBP machinery was tested. Cells expressing dCas9-FKBPx2 and ms2-FKBP were transfected with gRNA plasmids targeting MYOD1 (or NT gRNA for the control). After 48 hours of CEM87 (200 nM) exposure, RNA was extracted, qRT-qPCR was performed and results were normalized to Gapdh. The results show that mRNA levels increased 13-fold compared to untreated cells (FIG. 27A, $p<0.01$), whereas the cells expressing the NT gRNAs showed no significant changes in expression upon bifunctional CEM treatment (FIG. 27A, $p>0.05$).

Figure 27B:
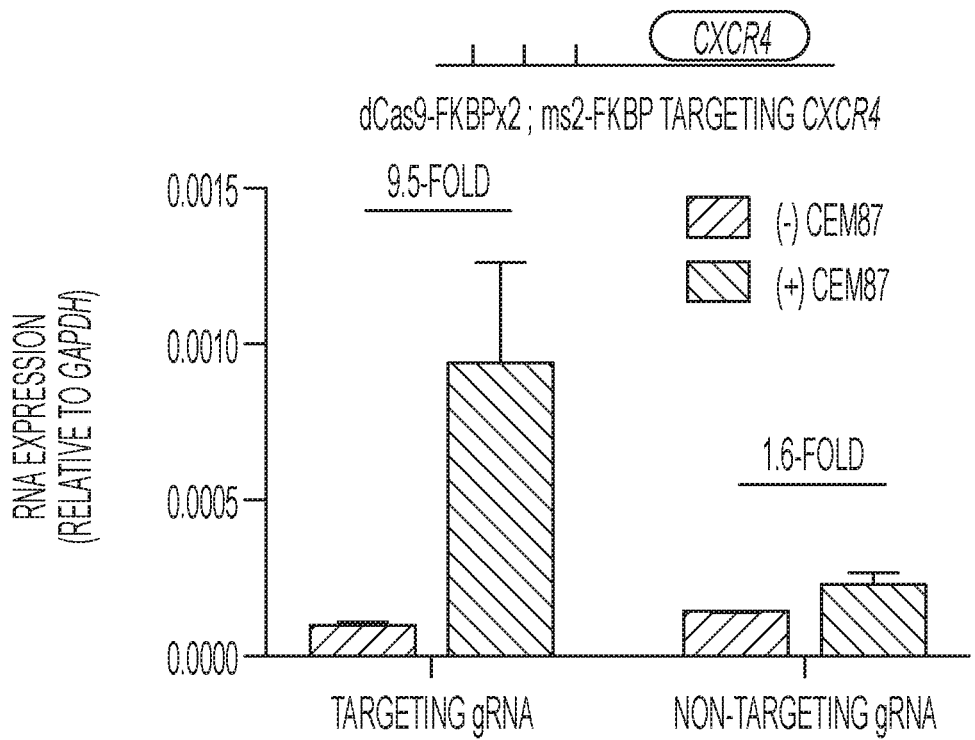
Figure 27C:
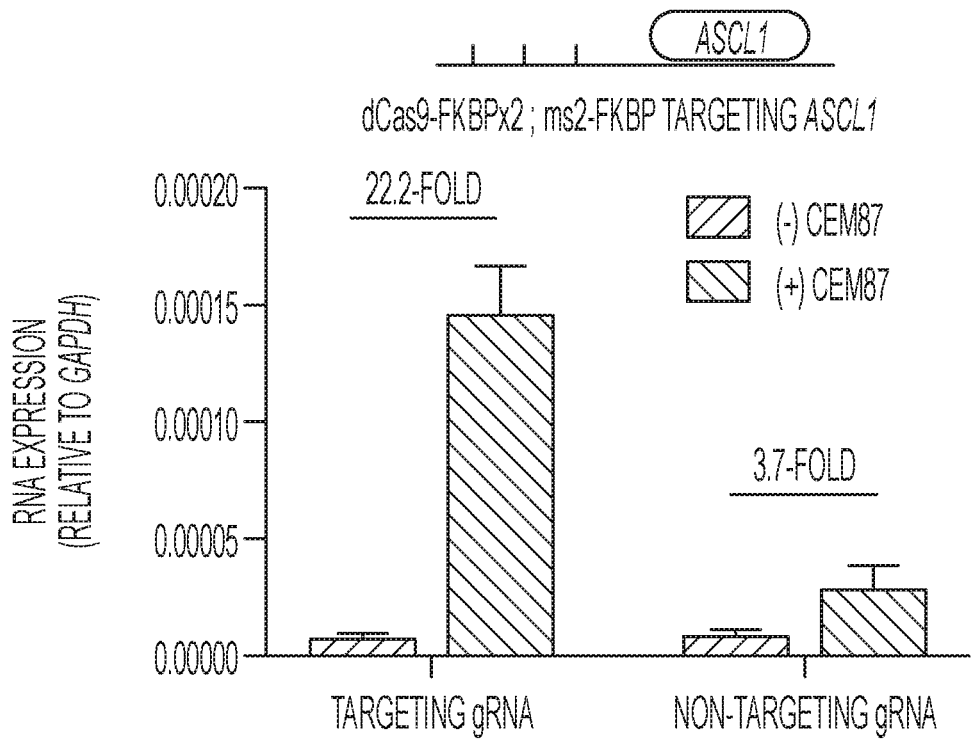

To determine the versatility of the dCas9-CEMa system, a second endogenous gene, C-X-C chemokine receptor type 4 (CXCR4), was tested. After 48 hours of CEM87 exposure, expression increased 10-fold compared to untreated cells (FIG. 27B, $p<0.005$), where-as the cells expressing the NT gRNA had a less than 2-fold change in CXCR4 expression (FIG. 27B, p<0.05). Lastly, endogenous Achaete-Scute family BHLH Transcription factor 1 (ASCL1) was targeted with previously tested and optimized gRNAs (Braun, S. M. G. et al. *Nat. Commun.* 8, (2017); (Chavez, A. et al. *Nat. Methods* 13, 563-567 (2016); (Konermann, S. et al. *Nature* 517, 583-588 (2015)). Upon 48 hours of CEM87-treatment, mRNA levels of ASCL1 increased 22-fold compared to untreated cells (FIG. 27C, p<0.00005), compared to a less than 4-fold increase observed in the NT samples (FIG. 27C, p<0.05).

In summary, the use of bifunctional CEMs capable of robustly activating endogenous genes in a dose-dependent, gene-specific manner were designed, synthesized, developed and improved. By adapting the bifunctional CEMa technology to dCas9 targeting constructs, any gene in the genome can be targeted by strategic gRNA designing. The ability to control the chromatin landscape and induce changes in the expression of endogenous mammalian genes in a direct, biologically-relevant manner has been demonstrated. This dCas9-CEMa technology paves the way for the targeting of disease relevant genes to ask specific, targeted questions about disease mechanisms of action. Since the gene activation platform described herein is chemically activated in a dose dependent manner, it will be useful in target validation work for visualization of trends between phenotype and gene dosage over a wide range of target gene concentrations. Additionally, the dCas9-CEMa platform can be developed as a novel therapeutic approach to changing gene expression levels driving human disease.

Methods:

Chemical Synthesis: See FIGS. 20A-D. Bifunctional CEMa compounds were diluted in DMSO (Sigma D2650) and kept dry at −20° C.

Plasmid design: To construct dCas9-FKBPx1 and -FKBPx2, Addgene #61425 was digested at the BamHI and BsrG1 sites. To insert the FKBPx1 (from Addgene #44245) and FKBPx2 (from N160) fusion, In-Fusion (#639650) was used with the following primers:

```
FKBPx1-Forward
                                      (SEQ ID NO: 15)
(5' GGCGGCCGCTGGATCCGGCGTGCAGGTGGAGACTAT), Reverse
                                      (SEQ ID NO: 16)
(5' CTCCACTGCCTGTACATTCCAGTTTTAGAAGCTCCACATC);

FKBPx2-Forward
                                      (SEQ ID NO: 17)
(5' CTCCACTGCCTGTACATTCCAGTTTTAGAAGCTCCACATC), Reverse
                                      (SEQ ID NO: 18)
(5' GGCGGCCGCTGGATCCGGGGTCCAAGTTGAAACCATTA).
```

To create a dCas9-SunTagx10 construct with a BFP fusion, Addgene #60903 was used and digested with Not1 and Sbf1 restriction enzymes, and re-inserted the WPRE and NLS domains from the original plasmid using In-Fusion and primers: Forward (5' GGTCCGATGGATCTA-CAGCGGCCGGGTGGAGGTCCAAAAAAGAAAAGG) (SEQ ID NO: 19), Reverse (5' CAGTGATC-GATCCCTGCAGGGCGGGGAGGCGGCCCAA) (SEQ ID NO: 20). To create a multiplex parent plasmid capable of expression the tre3g x6 gRNA and the BFP x1 gRNA from a single plasmid, Addgene #52963 was used and digested with Not1 and PspX1 restriction enzymes. The backbone (NEB, M0290S) was CIP treated and PNK annealed (NEB, M0201S) the following oligos (oligo 1: 5' GGC-CACTAGTCTCTGGAGACGAAACGTCTCTCTAGCCC) (SEQ ID NO: 21); and oligo 2: 5' TCGAGGGCTAGAGA-GACGTITCGTCTCCAGAGACTAGT) (SEQ ID NO: 22). After cleaning the reactions, the annealed insert and the CIP-treated backbone were ligated (NEB, M020S). For the multiplexing system, the insert plasmids were created and digested as previously described (Sakuma, T. et al. *Sci. Rep.* 4, 4-9 (2014) and the multiplex parent 23 plasmid was digested with BsmB1, CIP treated, then ligated together.

Cell culture: Low passage (p30-40) HEK 293T cells were cultured with high-glucose DMEM (Corning, 10-013-CV) supplemented with 10% FBS serum (Atlantic Biologicals, S11550), 10 mM HEPES (Corning, 25-060-C1), NEAA (Gibco, 11140-050), Pen/Strep, and 55 µM 2-Mercaptoethanol. Cells were passaged every 2-5 days and maintained at 10-90% confluency in an incubator at 37° C. and 5% $CO_2$.

Figure 19D:
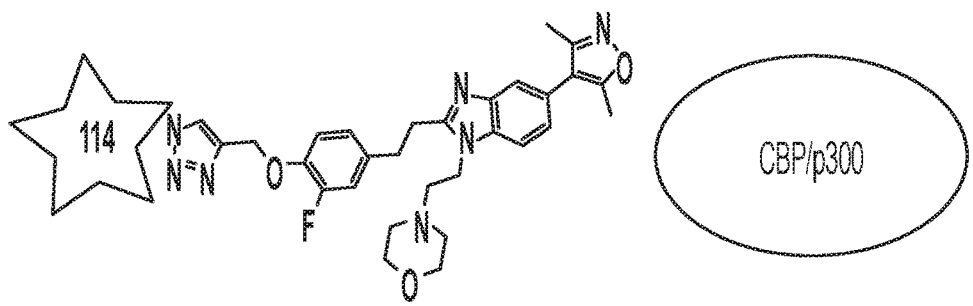

Cell Transfection: For FIG. 21, HEK 293T cells were split into 12-well plates with 100,000 cells per well. The next day, PEI (polyethlenimine, Polysciences #23966-1) transfection was done with 1 µg of DNA, 3 µL of PEI, and 100 µL of Optimem (Gibco, 31985070). For FIGS. 21A, 21B, 22, and 23 we transfected with 0.1 µg BFP reporter; 0.7 µg dCas9-X; 0.2 µg gRNA. For FIG. 19C, FIG. 19D, FIG. 24, and FIG. 24 we transfected with 0.1 µg BFP reporter; 0.5 µg dCas9-X; 0.2 µg scFv-FKBP or ms2-FKBP; 0.2 µg gRNA. Media was change 16 hours after transfection with fresh media, with or without bifunctional CEMa addition. After 48 hours of bifunctional CEMa exposure, cells were isolated for flow cytometry analysis. For FIG. 23, HEK 293T cells were split into 6-well plates with 200,000 cells per well. The next day, PIE transfection was done with 3 µg of DNA, 9 µL of PEI, and 200 µL of Optimem. For FIGS. 23A-C and 26, 3 µg of gRNA was added in equal ratio (if applicable). Media was change 16 hours after transfection with fresh media, with or without bifunctional CEMa addition. After 48 hours of bifunctional CEMa exposure, cells were isolate for RNA extraction.

Flow cytometry: Flow cytometry was performed with the Attune Nxt as previously described (Chiarella, A. M. et al. *Biochemistry* 57, 2756-2761 (2018)). The data presented represents three separate transfections and significance was determined with the student's t-test.

Lentiviral infection: Lentivirus production for HEK 293T infection was done using LentiX 293T cells (Clontech). Low passage cells (8-20) were plated onto 15 cm cells such that they were 70% confluent 24 hours later. Each plate was transfected with 18 µg of the plasmid of interest (dCas9-X), 13.5 µg of the Gag-Pol expressing plasmid (Addgene #12260), and 4.5 µg of the VSV-G envelope expressing plasmid (Addgene #12259). PEI transfection was done and 60 hours after transfection, the virus was spun down at 20,000 rpm for 2½ hours at 4° C. and then added to the HEK 293 Ts in combination with 10 µg/mL Polybrene (Santa Cruz, sc-134220). The selection of lentiviral constructs was done with either hygromycin (200 µg/mL) or blasticidin (12 µg/mL).

RNA extraction: For FIGS. 23 and 26, cells from the 6-well plates were isolated. Cells were washed with 1×PBS, disassociated with 0.05% trypsin, quenched with media, centrifuged and washed with 1×PBS. RNA extraction was performed with an RNeasy Plus Mini Kit (Qiagen, 74134) and the relative enrichment of mRNA was quantified with the RNA-to-$C_T$r 1-step kit (Thermo Fisher Scientific, 4389986). Three biological replicates were performed for RNA extraction. The qRT-PCR results represent two technical replicates for each of the three biological replicates.

Quartile analysis was done to exclude outliers and significance was determined with the student's t-test.

TABLE 3

Primers for qRT-PCR and source.

| Target: | Forward (5'-3') | Reverse (5'-3') | Source |
|---|---|---|---|
| Myod1 | CTCTCTGCTCCTTTGCCACA (SEQ ID NO: 23) | GTGCTCTTCGGGTTTCAGGA (SEQ ID NO: 24) | doi:10.1038/nmeth.2600 |
| CXCR4 | ACTACACCGAGGAAATGGGCT (SEQ ID NO: 25) | CCCACAATGCCAGTTAAGAAGA (SEQ ID NO: 26) | doi:10.1038/s41467-017-00644-y |
| ASCL1 | CGCGGCCAACAAGAAGATG (SEQ ID NO: 27) | CGACGAGTAGGATGAGACCG (SEQ ID NO: 28) | doi:10.1038/s41467-017-00644-y |
| Gapdh | CAATGACCCCTTCATTGACC (SEQ ID NO: 29) | TTGATTTTGGAGGGATCTCG (SEQ ID NO: 30) | doi:10.1038/nmeth.2600 |

TABLE 4

Protospacer Sequences (5'-3') of the gRNAs and source.

| Target: | Protospacer Sequence (5'-3') of the gRNA | Source |
|---|---|---|
| Tre3g x6 | TACGTTCTCTATCACTGATA (SEQ ID NO: 31) | doi:10.1038/nmeth.4042 |
| BFP x1 | TACAAACTTGGGTCGAATT (SEQ ID NO: 32) | Example 8 |
| Myod1 gRNA #1 | CCTGGGCTCCGGGCGTTT (SEQ ID NO: 33) | doi:10.1038/nmeth.2600 |
| Myod1 gRNA #2 | GGCCCCTGCGGCCACCCCG (SEQ ID NO: 34) | doi:10.1038/nmeth.2600 |
| Myod1 gRNA #3 | CTCCCTCCCTGCCCGGTAG (SEQ ID NO: 35) | doi:10.1038/nmeth.2600 |
| Myod1 gRNA #4 | AGGTTTGGAAAGGGCGTGC (SEQ ID NO: 36) | doi:10.1038/nmeth.2600 |
| CXCR4 gRNA #1 | GCAGACGCGAGGAAGAGGGCGC (SEQ ID NO: 37) | doi:10.1038/s41467-017-00644-y |
| CXCR4 gRNA #2 | CCGACCACCCGCAAACAGCA (SEQ ID NO: 38) | doi:10.1038/s41467-017-00644-y |
| CXCR4 gRNA #3 | GCCTCTGGGAGGTCCTGTCCGGCTC (SEQ ID NO: 39) | doi:10.1038/s41467-017-00644-y |
| ASCL1 gRNA #1 | CGGGAGAAAGGAACGGGAGG (SEQ ID NO: 40) | doi:10.1038/s41467-017-00644-y |
| ASCL1 gRNA #2 | TCCAATTTCTAGGGTCACCG (SEQ ID NO: 41) | doi:10.1038/s41467-017-00644-y |
| ASCL1 gRNA #3 | AAGAACTTGAAGCAAAGCGC (SEQ ID NO: 42) | doi:10.1038/s41467-017-00644-y |

Example 9: Bifunctional CEM Repressor (CEMr) Activation on Two Endogenous Mammalian Genes FIGS. 28A-C demonstrate a tool to target and repress specific mammalian genes through the redirecting of endogenous chromatin modifying machinery. Using the dCas9 technology as a DNA-targeting machinery, a gRNA is designed to target a gene of interest. By incorporating FKBP, CEMr is brought to the locus. CEM23 is an example of a bifunctional CEMr and the data show that it is capable of recruiting endogenous, repressive, chromatin-modifying machinery.

For these experiments, HEK293T cells were infected to express dCas9-FKBP and ms2-FKBP. The cells were transfected with six gRNAs targeting Myc1 (or one non-targeting control gRNA). A subset of cells were exposed to 100 nM of CEM23 for 48 hours. RNA was extracted and qRT-PCR was performed. Upon bifunctional CEMr-treatment, Myc1 expression decreased 2.1-fold (normalized to the non-targeting control). The same infected line was transfected with four gRNAs targeting Cxcr4 (or one non-targeting control gRNA). A subset of cells were exposed to 100 nM of CEM23 for 48 hours. RNA was extracted and qRT-PCR was performed. Upon bifunctional CEMr-treatment, Cxcr4 expression decreased 2.5-fold (normalized to the non-targeting control).

Example 11: Bifunctional Molecule System Redirects Chromatin Machinery to a Specific Gene Locus The data show that the bifunctional molecule system can regulate gene expression in a reversible and dose-dependent matter. The data also show that this system can be utilized to target disease-relevant genes in a relevant cancer model system.

Methods: Mouse embryonic stem cells express the DNA anchor (FKBP-Gal4) through lentiviral infection. PEI transfection is used for all 293/HEK and HCT116 experiments. The bifunctional chemical epigenetic modifiers (CEMs) are synthesized and resuspended in DMSO. In most cases they are added to the cells for 48 hours. To analyze gene expression, flow cytometry, fluorescent microscopy, ChIP-qPCR and qRT-PCR were used.

Summary: A platform was created that uses novel bifunctional molecule sets to use endogenous cellular machinery to either activate or repress gene activity. Disclosed herein is a new way to reversibly use dCas9 based targeting to activate (or repress) any gene. Epigenetic sculpting with CEMs is dose dependent and reversible. The evidence shown in FIGS. 30-31 demonstrates that this approach has the ability to target endogenous p53 which leads to apoptosis of targeted cancer cells.

What is claimed is:

1. A bifunctional chemical epigenetic modifier (CEM) comprising a molecule of FK506 or derivative thereof, a linker and a histone deacetylase inhibitor, wherein the histone deacetylase inhibitor is suberanilohydroxamic acid, depsipeptide or a derivative thereof.

2. The bifunctional CEM of claim 1, wherein the linker couples the FK506 or derivative thereof to the histone deacetylase inhibitor.

3. The bifunctional CEM of claim 1, wherein the linker is a homofunctional linker or a heterofunctional linker, wherein the homofunctional linker is a homobifunctional, homotrifunctional, or homotetrafunctional linker comprising two, three, or four reactive groups, respectively, that react with a primary amine, a thiol group, a hydroxyl group, or a carbohydrate, and the heterofunctional linker is a heterobifunctional, heterotrifunctional, or heterotetrafunctional linker comprising at least one reactive group that reacts with a primary amine, a thiol group, a hydroxyl group, or a carbohydrate.

4. A pharmaceutical composition comprising the composition of claim 1 and a pharmaceutically acceptable carrier.

5. A method of treating a patient with cancer or an autoimmune disorder, the method comprising:
   (a) identifying a patient in need of treatment; and
   (b) administering to the patient a therapeutically effective amount of the pharmaceutical composition of claim 4.

6. The method of claim 5, further comprising administering an effective amount of exogenous FK506 binding protein.

7. The method of claim 5, wherein the cancer is prostate cancer, castrate-resistant prostate cancer, triple negative breast cancer or urothelial carcinoma.

8. The method of claim 5, wherein the autoimmune disorder is selected from the group consisting of non-Hodgkin's lymphoma, rheumatoid arthritis, chronic lymphocytic leukemia, multiple sclerosis, systemic lupus erythematosus, autoimmune hemolytic anemia, pure red cell aplasia, idiopathic thrombocytopenic purpura, Evans syndrome, vasculitis, bullous skin disorders, type 1 diabetes mellitus, Sjogren's syndrome, Devic's disease, and Graves' disease ophthalmopathy.

* * * * *